(12) United States Patent
Brown et al.

(10) Patent No.: US 11,351,265 B2
(45) Date of Patent: Jun. 7, 2022

(54) PROCESS FOR FORMULATING AN ANIONIC AGENT

(71) Applicant: Dicerna Pharmaceuticals, Inc., Lexington, MA (US)

(72) Inventors: Bob Dale Brown, Millington, NJ (US); Bo Ying, Waltham, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 621 days.

(21) Appl. No.: 16/165,760

(22) Filed: Oct. 19, 2018

(65) Prior Publication Data

US 2019/0151461 A1    May 23, 2019

Related U.S. Application Data

(60) Division of application No. 14/852,481, filed on Sep. 11, 2015, now Pat. No. 10,137,201, which is a continuation of application No. PCT/US2014/029372, filed on Mar. 14, 2014.

(60) Provisional application No. 61/784,810, filed on Mar. 14, 2013.

(51) Int. Cl.
| | |
|---|---|
| *A61K 47/60* | (2017.01) |
| *A61K 47/54* | (2017.01) |
| *A61K 9/127* | (2006.01) |
| *C12N 15/11* | (2006.01) |

(52) U.S. Cl.
CPC ............ *A61K 47/60* (2017.08); *A61K 9/1271* (2013.01); *A61K 9/1272* (2013.01); *A61K 9/1277* (2013.01); *A61K 47/543* (2017.08); *C12N 15/111* (2013.01); *C12N 2310/11* (2013.01); *C12N 2310/14* (2013.01); *C12N 2320/32* (2013.01)

(58) Field of Classification Search
CPC ............ A61K 47/48215; A61K 47/543; A61K 47/60; A61K 9/1271; A61K 9/1272; A61K 9/1277; C12N 15/111; C12N 2310/11; C12N 2310/14; C12N 2320/32
USPC ................. 424/450, 489; 536/24.5
See application file for complete search history.

(56) References Cited

U.S. PATENT DOCUMENTS

| | | | |
|---|---|---|---|
| 2003/0118636 A1 | 6/2003 | Friesen et al. | |
| 2011/0250262 A1* | 10/2011 | Shimizu | A61K 8/34 424/450 |
| 2012/0015026 A1 | 1/2012 | Francese et al. | |
| 2012/0149894 A1* | 6/2012 | Cameron | A61K 9/1272 540/113 |

FOREIGN PATENT DOCUMENTS

| | | |
|---|---|---|
| CN | 102137713 A | 7/2011 |
| CN | 101616677 B | 7/2015 |
| KR | 20110110086 A | 10/2011 |
| WO | 2010/108934 A1 | 9/2010 |
| WO | 2012/099755 A1 | 7/2012 |

OTHER PUBLICATIONS

Boukhnikachvili et al. FEBS Lett. Jun. 9, 1997, vol. 409, pp. 188-194. entire document (Year: 1997).*
Yamauchi et al. Biochim Biophys Acta. Feb. 2, 2006, vol. 175, pp. 90-97. (Year: 2006).*
Schulze et al. Bioconjugate Chem., Apr. 21, 1999, vol. 10, pp. 548-552. (Year: 1999).*
Japanese Office Action dated Dec. 4, 2017 for Japanese Patent Application No. 2016-503077, 7 pages including English translation.
Chinese Office Action dated Feb. 4, 2017 for Chinese Application No. 201480021240.8, 27 pages (including English translation).
Semple et al., "Rational design of cationic lipids for siRNA delivery", Nature Biotechnology, vol. 28, Issue 2, pp. 172-176 and Online Methods, Jan. 17, 2010.
Boukhnikachvili et al., "Structure of In-Serum Transfecting DNA-Cationic Lipid Complexes," FEBS Lett., Jun. 9, 1997, vol. 409, pp. 188-194.
Schulze et al., "Synthesis of Novel Cationic Poly (Ethylene Glycol) Containing Lipids," Bioconjugate Chem., Apr. 21, 1999, vol. 10, pp. 548-552.
Xu et al., "Cholesterol Domains in Cationic Lipid/DNA Complexes Improve Transfection," Biochim. Biophys. Acta., Apr. 30, 2008, vol. 1778, Iss. 10, pp. 2177-2181.
Yamauchi et al., "Development of Wrapped Liposomes: Novel Liposomes Comprised of Polyanion Drug and Cationic Lipid Complexes Wrapped with Neutral Lipids," Biochim. Biophys. Acta., Feb. 2, 2006, vol. 175, pp. 90-97.
Notification of Transmittal of the International Search Report and the Written Opinion of the International Searching Authority, or the Declaration, PCT/US2014/029372 (Authorized Officer, Copenheaver, Blaine R.), 4 pages, dated Aug. 19, 2014.
Korean Office Action dated Feb. 14, 2021 for Korean Patent Application No. 10-2021-7001139, 13 pages including English translation.

\* cited by examiner

*Primary Examiner* — Janet L Epps-Smith
(74) *Attorney, Agent, or Firm* — Byron V. Olsen; MH2 Technology Law Group, LLP

(57) ABSTRACT

Formulations comprising anionic agents such as nucleic acids within a lipid-containing particle methods of formulating a lipid-containing particle comprising an anionic agent such as a nucleic acid, methods for preparing a lipid-containing particle comprising an anionic agent such as a nucleic acid, methods for therapeutic delivery of an anionic agent to a patient in need thereof, where the anionic agent is formulated in a lipid-containing particle as described herein.

20 Claims, 9 Drawing Sheets
Specification includes a Sequence Listing.

SEQUENCE LISTING

<160> NUMBER OF SEQ ID NOS: 8

<210> SEQ ID NO 1
<211> LENGTH: 25
<212> TYPE: DNA
<213> ORGANISM: artificial
<220> FEATURE:
<223> OTHER INFORMATION: synthetic oligonucleotide

<400> SEQUENCE: 1
gccagacuuu guuggauuug aaatt                25

<210> SEQ ID NO 2
<211> LENGTH: 27
<212> TYPE: DNA
<213> ORGANISM: artificial
<220> FEATURE:
<223> OTHER INFORMATION: synthetic oligonucleotide

<400> SEQUENCE: 2
aauuucaaau ccaacaaagu cuggcuu              27

```
<210> SEQ ID NO 3
<211> LENGTH: 25
<212> TYPE: DNA
<213> ORGANISM: artificial
<220> FEATURE:
<223> OTHER INFORMATION: synthetic oligonucleotide

<400> SEQUENCE: 3
aggaacuaug accucgacua cgact                                              25

<210> SEQ ID NO 4
<211> LENGTH: 27
<212> TYPE: DNA
<213> ORGANISM: artificial
<220> FEATURE:
<223> OTHER INFORMATION: synthetic oligonucleotide

<400> SEQUENCE: 4
agucguaguc gaggucauag uuccugu                                            27

<210> SEQ ID NO 5
<211> LENGTH: 25
<212> TYPE: DNA
<213> ORGANISM: artificial
<220> FEATURE:
<223> OTHER INFORMATION: synthetic oligonucleotide

<400> SEQUENCE: 5
agcuuuuuug cccugcguga ccaga                                              25

<210> SEQ ID NO 6
<211> LENGTH: 27
<212> TYPE: DNA
<213> ORGANISM: artificial
<220> FEATURE:
<223> OTHER INFORMATION: synthetic oligonucleotide

<400> SEQUENCE: 6
ucuggucacg cagggcaaaa aagcucc                                            27

<210> SEQ ID NO 7
<211> LENGTH: 25
<212> TYPE: DNA
<213> ORGANISM: artificial
<220> FEATURE:
<223> OTHER INFORMATION: synthetic oligonucleotide

<400> SEQUENCE: 7
auauuuuccc aucuguauua uuutt                                              25

<210> SEQ ID NO 8
<211> LENGTH: 27
<212> TYPE: DNA
<213> ORGANISM: artificial
<220> FEATURE:
<223> OTHER INFORMATION: synthetic oligonucleotide

<400> SEQUENCE: 8
guuauaaaag gguagacaua auaaaaa                                            27
```

PROCESS FOR FORMULATING AN ANIONIC AGENT

CROSS-REFERENCE

This application is a divisional of U.S. application Ser. No. 14/852,481 (Allowed), filed 11 Sep. 2015, which is a continuation of PCT International Application Serial Number PCT/US14/29372, filed Mar. 14, 2014, designating the United States, claiming priority from U.S. Provisional Application No. 61/784,810 entitled "Process for Formulating an Anionic Agent" and filed Mar. 14, 2013, incorporated herein in its entirety.

SEQUENCE LISTING

The instant application contains a Sequence Listing which has been submitted electronically in ASCII format and is hereby incorporated by reference in its entirety. Said ASCII copy, created on 12 Oct. 2018, is named 0243.0023-01_Sequence_Listing.txt and is 2 Kilobytes in size.

BACKGROUND OF THE INVENTION

Nucleic acid molecules cannot easily cross cell membranes because of their size and hydrophilicity. Delivery has therefore been one of the major challenges for nucleic acid therapeutics, e.g., antisense payloads and RNAi technology. To trigger RNase H activity or RNAi activity following systemic administration, a formulation containing nucleic acid molecules not only must (1) protect the payload from enzymatic and non-enzymatic degradation and (2) provide appropriate biodistribution of the formulation, but also (3) allow cellular uptake or internalization of the formulation and (4) facilitate delivery of the nucleic acid payload to the cytoplasm of the cell. Many formulations that excel in criteria 1 and 2 above are deficient in criteria 3 and 4, and many nucleic acid formulations therefore show excellent biodistribution but fail to knock down the target gene due to lack of systemic delivery and local delivery.

While a number of lipid-based formulations have recently been demonstrated to effect intracellular delivery of nucleic acid payloads to at least certain types of mammalian cells (e.g., mammalian liver cells), the precise proportions and methods of combining lipids, payloads and other components of such formulations can greatly influence the extent to which successful delivery of nucleic acid payloads is achieved. Accordingly, modest changes in the processes employed to obtain such lipid-based formulations have the potential to produce dramatic and surprising differences in delivery efficacy. As such, there is a need to optimize the process by which lipid-based formulations of nucleic acid payloads (and, by extension, anionic agents more generally) are obtained, thereby enhancing the delivery of such therapeutic anionic agents to cells.

SUMMARY OF THE INVENTION

The invention relates, at least in part, to methods of formulating anionic agents, e.g., anionic therapeutic agents such as nucleic acids. In particular aspects of the invention, a process for preparing a lipid-containing particle comprising an anionic agent (e.g., a nucleic acid payload) has been identified, which involves combining a lipid complex with the anionic agent under conditions in which, due to the order of addition of such components, the total lipid solvent concentration of the mixed solution increases or is held stable over time, rather than declines, resulting in a formulated particle that possesses improved structural homogeneity and improved efficacy of intracellular delivery of the anionic agent. (While not wishing to be bound by theory, improved structural homogeneity appears to result from a reduction in lipidic complex dissolution during the mixing process, as compared to processes that produce a decline in lipid solvent concentration during the process of mixing the lipid complex and the anionic agent.) Without wishing to be bound by theory, at least one advantage of the methods of the instant invention is that they are more scalable than other processes, allowing for improved particle formation/formulation in amounts sufficient for, e.g., performance of clinical trials and/or commercial sale.

In other aspects of the invention, processes are provided which are based upon the surprising observation that a relatively low solubility limit possessed by an individual lipid or sterol in a solvent (e.g., ethanol or alcohol or organic solution or mixture thereof) can be effectively raised at room temperature by mixing other lipid(s) and/or sterol(s) together in a solvent (or, optionally, simply in a neat lipid oil or mixture of lipid oils) before adding this mixture of other lipid(s) and/or sterol(s) in oil or solvent to the relatively low solubility lipid or sterol, optionally further mixing such lipid and/or sterol suspension into the solvent. For example, while the solubility limit of cholesterol in ethanol at room temperature was observed to be about 10-11 mg/ml in the absence of other lipids and/or sterols, it was unexpectedly discovered that a pre-mixing of additional lipids as described herein in ethanol before addition of such a lipid suspension in ethanol to cholesterol (as a powder) at room temperature allowed for cholesterol levels of 20 mg/ml or higher to be achieved in the solution, while the total lipid content of such solutions could also be raised to 37 mg/ml, 74 mg/ml, or even higher levels. Thus, a process is provided for raising the amount of an original lipid, sterol and/or blend of lipid(s) and/or sterol(s) that may be solubilized in a solvent (e.g., an alcoholic solvent, e.g., ethanol) by pre-mixing other lipid(s), sterol(s) and/or blend of lipid(s) and/or sterol(s), as oils, powders and/or in solvent(s), before adding such a pre-mixture to the original solubility-limited lipid, sterol and/or blend of lipid(s), thereby effectively raising the solubility limit of the original lipid in the solvent. In certain related embodiments, the invention provides a process for making a particle that involves pre-mixing elevated concentrations of lipid and/or sterol components as oils, powders and/or in solvent (e.g., ethanol), adding this mixture to a lipid and/or sterol that possesses relatively low solubility in the solvent in the absence of such pre-mixed lipid(s) and/or sterol(s), and combining this mixture with anionic agent-containing aqueous solutions or suspensions (optionally, such anionic agents are complexed with lipid prior to such addition of solvent-suspended lipids). Without wishing to be bound by theory, it is believed that the newly discovered ability to provide high concentration solutions of lipids/sterols at such elevated concentrations enhances the homogeneity of a lipid-anionic agent particle population, as compared to the concentrations at which such lipids/sterols are routinely used within the particle formulation process.

In one aspect, the invention provides a method of producing a particle harboring an anionic agent that involves combining a modified lipid which prevents particle aggregation during lipid-anionic agent particle formation with a cationic lipid in an acidic aqueous solution, in an amount sufficient for a complex to form; combining this complex with an anionic agent; combining the complex-anionic agent with a neutral aqueous solution to form a complex-anionic agent aqueous suspension; forming a solution or suspension that includes at least one structural lipid, sterol, cationic lipid or modified lipid which prevents particle aggregation during lipid-anionic agent particle formation; and combining this solution or suspension with the complex-anionic agent aqueous solution of the previous step by a method that either involves adding the solution or suspension to the complex-anionic agent aqueous suspension or in-line mixing the solution or suspension and the complex-anionic agent aqueous solution.

In certain embodiments, the acidic aqueous solution includes HCl. Optionally, the acidic aqueous solution possesses a pH of less than 4, in certain embodiments, 2.3. In related embodiments, the acidic aqueous solution is about 60 mM HCl.

In one embodiment, the cationic lipid that is present in acidic aqueous solution possesses a protonatable group. Optionally, this cationic lipid has a pKa of 4 to 11. In certain embodiments, this cationic lipid is DODMA, DOTMA, or a cationic lipid of Table 1.

In certain embodiments, the modified lipid which prevents particle aggregation during lipid-anionic agent particle formation is a PEG-lipid, optionally DMPE-PEG, DSPE-PEG or DSG-PEG. In related embodiments, the PEG is PEG2k.

In some embodiments, the modified lipid-cationic lipid complex is between 60 and 75 nM in diameter.

In certain embodiments, the anionic agent is a polyanionic agent. In related embodiments, the anionic agent is a nucleic acid. Optionally, the nucleic acid is an antisense oligonucleotide or a double-stranded nucleic acid. In certain embodiments, the double-stranded nucleic acid is a small hairpin RNA (shRNA) or a siRNA. In a related embodiment, the double-stranded nucleic acid is a substrate for human Dicer and is optionally a DsiRNA.

In some embodiments, the neutral aqueous solution is water.

In certain embodiments, forming a solution or suspension that includes at least one structural lipid, sterol, cationic lipid or modified lipid which prevents particle aggregation during lipid-anionic agent particle formation involves dissolving in ethanol the at least one lipid. Optionally, this forming of a solution or suspension involves dissolving the lipid or sterol in 100% ethanol. In related embodiments the structural lipid is DSPC, DPPC or DOPC. In certain embodiments, the sterol is cholesterol. Optionally, the cationic lipid is selected from Table 1.

In certain embodiments, the particle harboring an anionic agent is between 90 and 110 nm in diameter.

In one embodiment, the particle harboring an anionic agent is made at a scale of 10 mg or more of anionic agent, 50 mg or more of anionic agent, 100 mg or more of anionic agent, 250 mg or more of anionic agent, 500 mg or more of anionic agent, 1 g or more of anionic agent, 2 g or more of anionic agent, 3 g or more of anionic agent, 4 g or more of anionic agent, 5 g or more of anionic agent, 7.5 g or more of anionic agent, 10 g or more of anionic agent, 20 g or more of anionic agent, 40 g or more of anionic agent, 50 g or more of anionic agent, 100 g or more of anionic agent, 200 g or more or anionic agent, 300 g or more of anionic agent, 400 g or more of anionic agent, 500 g or more of anionic agent, 1 kg or more of anionic agent, 2 kg or more of anionic agent, 3 kg or more of anionic agent, 4 kg or more of anionic agent, 5 kg or more of anionic agent or 10 kg or more of anionic agent.

In another embodiment, the particle harboring an anionic agent possesses one or more of the following properties: improved size and/or PDI, improved efficacy in a subject administered the particle or improved tolerability in a subject administered the particle, as compared to an appropriate control particle formed by an appropriate control process that involves adding the complex-anionic agent aqueous suspension to the solvent-based solution or suspension.

In an additional embodiment, the method further involves combining the particle harboring an anionic agent with a volume of water sufficient to reduce the concentration of ethanol within the combined solution to 10% or less.

In another embodiment, the method also involves performing one of the following processes: tangential flow filtration (TFF) or dialysis upon the combined solution. Optionally, the combined solution is dialyzed against PBS.

Another aspect of the invention provides a method of producing a particle harboring an anionic agent which involves combining in an acidic aqueous solution a modified lipid which prevents particle aggregation during lipid-anionic agent particle formation with a cationic lipid, in an amount sufficient for a complex to form; combining this complex with an anionic agent; combining this complex-anionic agent with a neutral aqueous solution to form a complex-anionic agent aqueous suspension; forming a solution or suspension having at least one of a structural lipid, a sterol, a cationic lipid or a modified lipid which prevents particle aggregation during lipid-anionic agent particle formation; and adding this solution or suspension to the complex-anionic agent aqueous suspension.

An additional aspect of the invention provides a method for increasing the solubility of a first lipid or sterol in a solvent which involves combining a second lipid or sterol with the solvent to form a second lipid or sterol solution in the solvent, where the solvent is free of the first lipid; and combining the second lipid or sterol solution in the solvent with the first lipid or sterol to form a solution of the second lipid or sterol and the first lipid or sterol, where the solubility of the first lipid or sterol in the solvent in the presence of the second lipid or sterol is higher than the solubility of the first lipid or sterol in the solvent in the absence of the second lipid or sterol.

A further aspect of the invention provides a method for increasing the solubility of a first lipid or sterol in a solvent which involves combining a second lipid or sterol with the first lipid or sterol in the absence of a solvent, where the solubility of the first lipid or sterol in the solvent in the presence of the second lipid or sterol is higher than the solubility of the first lipid or sterol in the solvent in the absence of the second lipid or sterol.

In one embodiment, the first lipid or sterol is a sterol, optionally cholesterol, cholestanone, cholestenone, coprostanol, 3β-[-(N—(N',N'-dimethylaminoethane)-carbamoyl] cholesterol (DC-cholesterol) or bis-guanidium-tren-cholesterol (BGTC).

In another embodiment, the first lipid or sterol is present at a concentration of 10 mg/ml or more, 11 mg/ml or more, 12 mg/ml or more, 15 mg/ml or more, 20 mg/ml or more, 25 mg/ml or more, 30 mg/ml or more, 35 mg/ml or more, 37 mg/ml or more, 40 mg/ml or more, 45 mg/ml or more, 50 mg/ml or more, 55 mg/ml or more, 60 mg/ml or more, 65 mg/ml or more, 70 mg/ml or more, 74 mg/ml or more, 75 mg/ml or more, 80 mg/ml or more, 85 mg/ml or more, 90 mg/ml or more, 95 mg/ml or more, 100 mg/ml or more, 150 mg/ml or more, 200 mg/ml or more, 250 mg/ml or more, 500 mg/ml or more or 1 g/ml or more within the solution of the second lipid or sterol and the first lipid or sterol.

In one embodiment, the total lipid content of the solution of the second lipid or sterol and the first lipid or sterol is 12 mg/ml or more, 15 mg/ml or more, 20 mg/ml or more, 25 mg/ml or more, 30 mg/ml or more, 35 mg/ml or more, 37 mg/ml or more, 40 mg/ml or more, 45 mg/ml or more, 50 mg/ml or more, 55 mg/ml or more, 60 mg/ml or more, 65 mg/ml or more, 70 mg/ml or more, 74 mg/ml or more, 75 mg/ml or more, 80 mg/ml or more, 85 mg/ml or more, 90 mg/ml or more, 95 mg/ml or more, 100 mg/ml or more, 150 mg/ml or more, 200 mg/ml or more, 250 mg/ml or more, 500 mg/ml or more or 1 g/ml or more.

In one embodiment, the second lipid or sterol solution in the solvent includes one or more additional lipids of Tables 1-4.

In another embodiment, the solution of the second lipid or sterol and the first lipid or sterol includes at least one of a structural lipid, a sterol, a cationic lipid or a modified lipid which prevents particle aggregation during lipid-anionic agent particle formation.

Another aspect of the invention provides a method of producing a particle having a first lipid or sterol, a second lipid or sterol and a small molecule, which involves combining a second lipid or sterol with a solvent to form a second lipid or sterol solution in the solvent, where the solvent is free of the first lipid or sterol; and combining the second lipid or sterol solution in the solvent with the first lipid or sterol to form a solution of the second lipid or sterol and the first lipid or sterol, where the solubility of the first lipid or sterol in the solvent in the presence of the second lipid or sterol is higher than the solubility of the first lipid or sterol in the solvent in the absence of the second lipid or sterol, then combining this solution of the second lipid or sterol and the first lipid or sterol with a small molecule.

An additional aspect of the invention provides a method of producing a particle having a first lipid or sterol, a second lipid or sterol and an anionic agent, which involves combining a second lipid or sterol with a solvent to form a second lipid or sterol solution in the solvent, where the solvent is free of the first lipid or sterol; and combining the second lipid or sterol solution in the solvent with the first lipid or sterol to form a solution of the second lipid or sterol and the first lipid or sterol, where the solubility of the first lipid or sterol in the solvent in the presence of the second lipid or sterol is higher than the solubility of the first lipid or sterol in the solvent in the absence of the second lipid or sterol, then combining this solution of the second lipid or sterol and the first lipid or sterol with an anionic agent.

In a further aspect, the invention provides a method of producing a particle having a first lipid or sterol, a second lipid or sterol and an anionic agent, which involves combining in an acidic aqueous solution a modified lipid which prevents particle aggregation during lipid-anionic agent particle formation and a cationic lipid, in an amount sufficient for a complex to form; combining this complex with an anionic agent; combining a neutral aqueous solution with the complex-anionic agent to form a complex-anionic agent aqueous suspension; combining a second lipid or sterol with a solvent to form a second lipid or sterol solution in the solvent, where the solvent is free of the first lipid or sterol; combining the second lipid or sterol solution in the solvent with the first lipid or sterol to form a solution of the second lipid or sterol and the first lipid or sterol; and combining the solution of the second lipid or sterol and the first lipid or sterol with the complex-anionic agent aqueous solution.

In certain embodiments, the solubility of the first lipid or sterol in the solvent in the presence of the second lipid or sterol is higher than the solubility of the first lipid or sterol in the solvent in the absence of the second lipid or sterol.

In one embodiment, the solution of the second lipid or sterol and the first lipid or sterol includes at least one of a structural lipid, a sterol, a cationic lipid or a modified lipid which prevents particle aggregation during lipid-anionic agent particle formation.

In another embodiment, the particle possesses at least one of the following properties: improved size and/or PDI, improved efficacy in a subject administered the particle or improved tolerability and/or reduced toxicity in a subject administered the particle, as compared to an appropriate control particle formed by an appropriate control process that involves exposing the first lipid or sterol to the solvent before the second lipid or sterol is exposed to the solvent.

In certain embodiments, the solution of the second lipid or sterol and the first lipid or sterol is added to the complex-anionic agent aqueous suspension or the solution of the second lipid or sterol and the first lipid or sterol is in-line mixed with the complex-anionic agent aqueous solution.

In certain embodiments, it is also contemplated that the solubility of a first lipid or sterol in a solvent can be effectively raised by initially adding the first lipid or sterol to the solvent at a concentration below the solubility limit of the first lipid or sterol, then adding a second lipid or sterol to the solution, and then adding the first lipid or sterol to the solution, such that the first lipid or sterol is added to achieve a concentration in the second lipid/sterol-containing solution that exceeds the original solubility limit of the first lipid or sterol in the solvent absent such addition of the second lipid or sterol.

In one aspect, the invention features a compound (e.g., lipid or cationic lipid) having the formula:

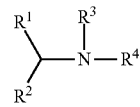

(I), or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl, where the $R^1$ and $R^2$ is not substituted with an oxo on the carbon adjacent to >CHNR$^3$R$^4$; $R^3$ is H or optionally substituted $C_{1-6}$ alkyl; and $R^4$ is unsubstituted $C_{1-6}$ alkyl that is substituted with —NR$^{4a}$R$^{4b}$, substituted $C_{1-6}$ alkyl that is further substituted with —NR$^{4a}$R$^{4b}$, or optionally substituted $C_{3-7}$ heterocyclyl, where each R$^{4a}$ and R$^{4b}$ is, independently, H, C(=NH)NH$_2$, or optionally substituted $C_{1-6}$ alkyl, or where R$^{4a}$ and R$^{4b}$ combine together to form optionally substituted $C_{3-7}$ heterocyclyl; and where $R^3$ and $R^4$ can combine together to form an optionally substituted $C_{3-7}$ heterocyclyl; where $R^3$ and $R^4$ do not combine together to form optionally substituted imidazolyl or optionally substituted benzimidazolyl or optionally substituted succinimidyl; where one, and only one, primary amine can be present on either $R^3$ or $R^4$ or no primary amine is present on either $R^3$ or $R^4$; and where neither $R^3$ nor $R^4$ is an optionally substituted amide; and where when $R^1$ or $R^2$ is saturated $C_{11}$ alkyl or saturated $C_{15}$ alkyl, $R^3$ is not H; where when $R^1$ or $R^2$ is saturated $C_{16}$ alkyl or saturated $C_{17}$ alkyl, $R^1$ and $R^2$ is not substituted with hydroxy; where when $R^1$ or $R^2$ is saturated $C_{17}$ alkyl, $R^3$ or R⁴ is not substituted with hydroxy; and where when R¹ or R² is saturated C₁₈ alkyl, R⁴ is not substituted with optionally substituted imidazolyl.

In some embodiments, R³ is C₁₋₆ alkyl substituted with —NR³ᵃR³ᵇ and where each R³ᵃ and R³ᵇ is, independently, H or optionally substituted C₁₋₆ alkyl. In particular embodiments, each R³ᵃ and R³ᵇ is, independently, H or C₁₋₆ alkyl.

In some embodiments, R⁴ is unsubstituted C₁₋₆ alkyl that is substituted with —NR⁴ᵃR⁴ᵇ. In particular embodiments, R⁴ is substituted C₁₋₆ alkyl (e.g., substituted C₁₋₃ alkyl, substituted C₁₋₂ alkyl, substituted C₁ alkyl, substituted C₂ alkyl, or substituted C₃ alkyl,) or C₁₋₆ aminoalkyl that is further substituted with —NR⁴ᵃR⁴ᵇ. In some embodiments, R⁴ is C₁₋₆ alkyl substituted with an oxo and is further substituted with —NR⁴ᵃR⁴ᵇ. In some embodiments, R⁴ᵃ and R⁴ᵇ combine together to form an optionally substituted C₃₋₇ heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, or optionally substituted pyrazolyl). In some embodiments, each R⁴ᵃ and R⁴ᵇ is, independently, optionally substituted C₁₋₆ alkyl. In some embodiments, R⁴ is unsubstituted C₁₋₆ alkyl that is substituted with optionally substituted C₃₋₇ heterocyclyl (e.g., any described herein). In some embodiments, R⁴ is substituted C₁₋₆ alkyl (e.g., with an oxo) or a C₁₋₆ aminoalkyl that is further substituted with optionally substituted C₃₋₇ heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl).

In some embodiments, R³ and R⁴ combine together to form an optionally substituted C₃₋₇ heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl).

In some embodiments, the compound (e.g., lipid or cationic lipid) has the formula:

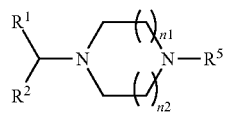

(IIa), or a pharmaceutically acceptable salt thereof, where each R¹ and R² is, independently, optionally substituted C₁₁₋₂₄ alkyl, optionally substituted C₁₁₋₂₄ alkenyl, optionally substituted C₁₁₋₂₄ alkynyl, optionally substituted C₁₁₋₂₄ heteroalkyl, optionally substituted C₁₁₋₂₄ heteroalkenyl, or optionally substituted C₁₁₋₂₄ heteroalkynyl; each n1 and n2 is, independently, an integer from 0 to 2 (e.g., n1 and n2 are both 1 or n1 is 1 and n2 is 2); and R⁵ is selected from the group consisting of H, optionally substituted C₁₋₆ alkyl, and optionally substituted heterocyclyl (e.g., unsubstituted C₁₋₆ alkyl or C₁₋₆ alkyl or C₁₋₆ alkyl substituted with optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl). In some embodiments, the compound is selected from the group consisting of L-2, L-5, L-6, L-22, L-23, L-24, L-25, L-26, L-28, L-29, L-45, and L-48, or a pharmaceutically acceptable salt thereof.

In some embodiments, the compound (e.g., lipid or cationic lipid) has the formula:

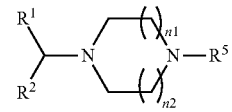

(IIb), or a pharmaceutically acceptable salt thereof, where each R¹ and R² is, optionally substituted C₁₁₋₂₄ alkyl, optionally substituted C₁₁₋₂₄ alkenyl, optionally substituted C₁₁₋₂₄ alkynyl, optionally substituted C₁₁₋₂₄ heteroalkyl, optionally substituted C₁₁₋₂₄ heteroalkenyl, optionally substituted C₁₁₋₂₄ heteroalkynyl; each n1 and n2 is, independently, an integer from 0 to 2 (e.g., n1 and n2 are both 1 or n1 is 1 and n2 is 2); and R⁵ is selected from the group consisting of H, optionally substituted C₁₋₆ alkyl, and optionally substituted heterocyclyl (e.g., unsubstituted C₁₋₆ alkyl or C₁₋₆ alkyl substituted with optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl). In some embodiments, the compound is selected from the group consisting of L-27 and L-47, or a pharmaceutically acceptable salt thereof.

In some embodiments for any formula described herein (e.g., formulas (I), (IIa), and (IIb)), R⁵ is C₁₋₆ alkyl substituted with NR⁵ᵃR⁵ᵇ, where each R⁵ᵃ and R⁵ᵇ is, independently, H, optionally substituted C₁₋₆ alkyl (e.g., optionally substituted C₁₋₆ alkyl), and where R⁵ᵃ and R⁵ᵇ can combine together to form optionally substituted C₃₋₇ heterocyclyl. In some embodiments, R⁵ is optionally substituted heterocyclyl (e.g., optionally substituted pyrrolidinyl, optionally substituted imidazolidinyl, optionally substituted pyrazolidinyl, optionally substituted piperidinyl, optionally substituted piperazinyl, optionally substituted azepanyl, optionally substituted pyrrolyl, optionally substituted imidazolyl, optionally substituted pyrazolyl, optionally substituted pyridinyl, optionally substituted pyrazinyl, optionally substituted pyrimidinyl, or optionally substituted pyridazinyl).

In some embodiments, the compound (e.g., lipid or cationic lipid) has the formula:

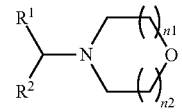

(IIc), or a pharmaceutically acceptable salt thereof, where each R¹ and R² is, optionally substituted C₁₁₋₂₄ alkyl, optionally substituted C₁₁₋₂₄ alkenyl, optionally substituted C₁₁₋₂₄ alkynyl, optionally substituted C₁₁₋₂₄ heteroalkyl, optionally substituted C₁₁₋₂₄ heteroalkenyl, optionally substituted C₁₁₋₂₄ heteroalkynyl; and each n1 and n2 is, independently, an integer from 0 to 2 (e.g., n1 and n2 are both 0 or n1 is 1 and n2 is 2). In some embodiments, the compound is L-46, or a pharmaceutically acceptable salt thereof.

In some embodiments, the compound (e.g., lipid or cationic lipid) has the formula:

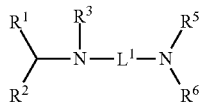

(IId), or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl, or where $R^5$ and $R^6$ combine to form an optionally substituted $C_{3-7}$ heterocyclyl.

In some embodiments, the compound (e.g., lipid or cationic lipid) has the formula:

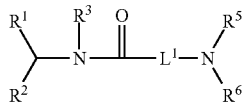

(IIe), or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl, or where $R^5$ and $R^6$ combine to form an optionally substituted $C_{3-7}$ heterocyclyl.

In some embodiments of formulas (IId) or (IIe), $R^5$ and $R^6$ combine to form optionally substituted pyrrolidinyl, optionally substituted imidazolidinyl, optionally substituted pyrazolidinyl, optionally substituted piperidinyl, optionally substituted piperazinyl, or optionally substituted azepanyl.

In some embodiments, the compound is selected from the group consisting of L-1, L-3, L-4, L-7, L-9, L-10, L-11, L-12, L-15, L-16, L-17, L-18, L-19, L-30, L-31, L-32, L-33, L-34, L-42, L-43, and L-49, or a pharmaceutically acceptable salt thereof.

In some embodiments, the compound (e.g., lipid or cationic lipid) has the formula:

(IIf)

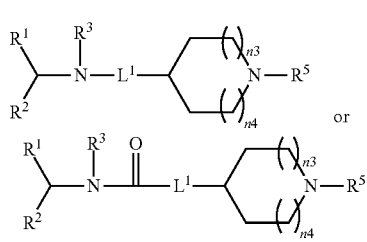

or (IIg), or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; each n3 and n4 is, independently, an integer from 0 to 2; and $R^5$ is H or optionally substituted $C_{1-6}$ alkyl.

In some embodiments, the compound is selected from the group consisting of L-14, L-21, and L-36, or a pharmaceutically acceptable salt thereof.

In some embodiments of any formula described herein (e.g., formulas (IId)-(IIj), e.g., formulas (IId)-(IIg)), $R^3$ is $C_{1-6}$ alkyl substituted with $-NR^{3a}R^{3b}$ and where each $R^{3a}$ and $R^{3b}$ is, independently, H or optionally substituted $C_{1-6}$ alkyl. In some embodiments, $R^3$ is unsubstituted $C_{1-6}$ alkyl.

In some embodiments of any formula described herein (e.g., formulas (IId)-(IIj), e.g., formulas (IId)-(IIg)), $L^1$ is $C_{1-6}$ alkylene substituted with methyl, ethyl, propyl, or $-NR^{La}R^{Lb}$, where each $R^{La}$ and $R^{Lb}$ is, independently, H or optionally substituted $C_{1-6}$ alkyl.

In some embodiments, the compound (e.g., lipid or cationic lipid) has the formula:

(IIh)

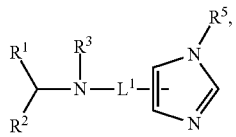

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and $R^5$ is H or optionally substituted $C_{1-6}$ alkyl.

In some embodiments, $L^1$ is linked to the imidazolyl group at the 4-position.

In some embodiments, the compound is selected from the group consisting of L-8, L-13, L-20, L-35, and L-44, or a pharmaceutically acceptable salt thereof.

In some embodiments, the compound (e.g., lipid or cationic lipid) has the formula:

(IIi)

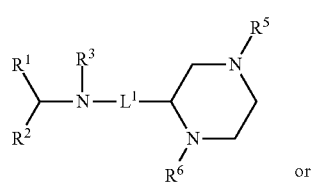

or (IIj)

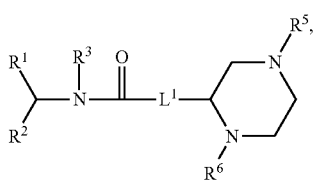

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl.

In some embodiments, the compound (e.g., lipid or cationic lipid) has the formula:

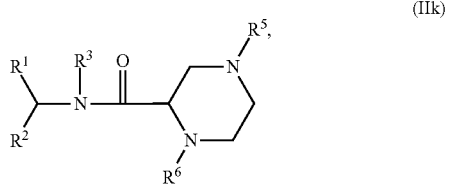

(IIk)

or a pharmaceutically acceptable salt thereof, where each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; and each $R^5$ and $R^6$ is, independently, H or optionally substituted $C_{1-6}$ alkyl.

In some embodiments of any formula described herein (e.g., formulas (IId)-(IIk), e.g., formulas (IIi)-(IIk)), each $R^5$ and $R^6$ is, independently, $C_{1-6}$ alkyl substituted with —$NR^{5a}R^{5b}$ and where each $R^{5a}$ and $R^{5b}$ is, independently, H or optionally substituted $C_{1-6}$ alkyl.

In some embodiments, the compound is selected from the group consisting of L-37, L-38, L-39, L-40, and L-41, or a pharmaceutically acceptable salt thereof.

In some embodiments of any formula described herein (e.g., formulas $L^1$ is optionally substituted $C_{1-6}$ alkylene.

In some embodiments of any formula described herein (e.g., formulas (I) or (IIa)-(IIk)), $R^3$ is optionally substituted $C_{1-6}$ alkyl. In some embodiments, each $R^1$ and $R^2$ is, independently, unsubstituted $C_{11-24}$ alkenyl or unsubstituted $C_{11-24}$ heteroalkenyl, including straight and branched forms (e.g., each $R^1$ and $R^2$ is, independently, unsubstituted $C_{11-24}$ alkenyl or unsubstituted $C_{11-24}$ heteroalkenyl containing one or more double bonds). In some embodiments, one of $R^1$ or $R^2$ is not saturated $C_{11-24}$ alkyl. In some embodiments, both $R^1$ and $R^2$ are not saturated $C_{11-24}$ alkyl. In some embodiments, each $R^1$ and $R^2$ is, independently, selected from the group consisting of linolenyl (C18:3), linolenyloxy (C18:3), linolenoyl (C18:3), linoleyl (C18:2), linoleyloxy (C18:2), linoleoyl (C18:2), oleyl (C18:1), oleyloxy (18:1), oleyloxymethylene (18:1), oleoyl (C18:1), oleoylmethylene (C18:1), stearyl (C18:0), stearyloxy (C18:0), stearoyl (C18:0), palmityl (C16:0), palmityloxy (C16:0), palmitoyl (C16:0), palmitoylmethylene (C16:0), myristyl (C14:0), myristyloxy (C14:0), myristoyl (C14:0), lauryl (C12:0), lauryloxy (C12:0), and lauroyl (C12:0), e.g., linoleyl (C18:2) or oleyl (C18:1). In some embodiments, $R^1$ and $R^2$ are the same or different.

In some embodiments of any formula described herein (e.g., formulas (I) or (IIa)-(IIk)), $R^3$ or $R^4$, but not both $R^3$ and $R^4$, is substituted with a primary amine. In some embodiments, both $R^3$ and $R^4$ are not substituted with a primary amine.

In some embodiments of any formula described herein (e.g., formulas (I) or (IIa)-(IIk)), $R^3$ and $R^4$, together with the N to which they are attached, include a head group of one of H-1 to H-52 from Tables 2 and 3. In some embodiments, each $R^1$ and $R^2$ is, independently, selected from the group consisting of linolenyl (C18:3), linolenyloxy (C18:3), linolenoyl (C18:3), linoleyl (C18:2), linoleyloxy (C18:2), linoleoyl (C18:2), oleyl (C18:1), oleyloxy (18:1), oleyloxymethylene (18:1), oleoyl (C18:1), oleoylmethylene (C18:1), stearyl (C18:0), stearyloxy (C18:0), stearoyl (C18:0), palmityl (C16:0), palmityloxy (C16:0), palmitoyl (C16:0), palmitoylmethylene (C16:0), myristyl (C14:0), myristyloxy (C14:0), myristoyl (C14:0), lauryl (C12:0), lauryloxy (C12:0), and lauroyl (C12:0), e.g., each $R^1$ and $R^2$ is, independently, linoleyl (C18:2) or oleyl (C18:1).

In another aspect, the compound of the invention include $R^1R^2$—CH-A, where $R^1$ and $R^2$ is a tail group (e.g., any described herein, e.g., in Table 4) and A is a head group (e.g., any described herein, e.g., in Tables 2 and 3). In some embodiments, the head group is one of H-1 to H-52, e.g., H-2, H-5, H-6, H-19, H-26, or H-43 (e.g., H-5 or H-43).

In another aspect, the compound of the invention is any compound provided in Table 1, or a pharmaceutically acceptable salt thereof.

In one aspect, the invention features a formulation including any compound described herein (e.g., one or more compound provided in Table 1), or a pharmaceutically acceptable salt thereof.

In some embodiments, the formulation includes two or more of the compounds, e.g., two, three, four, five, six, seven, or more of the compounds.

In any of the above aspects, the compounds of the invention includes two unsaturated lipid tail groups (e.g., each $R^1$ and $R^2$ is, independently, optionally substituted $C_{11-24}$ alkenyl, optionally substituted $C_{11-24}$ alkynyl, optionally substituted $C_{11-24}$ heteroalkenyl, or optionally substituted $C_{11-24}$ heteroalkynyl).

In any of the above aspects, the compounds of the invention include lipid tail groups, where these groups do not include an oxygen adjacent to —$CHR^3R^4$ (e.g., each $R^1$ and $R^2$ is, independently, optionally substituted $C_{11-24}$ alkyl, optionally substituted $C_{11-24}$ alkenyl, or optionally substituted $C_{11-24}$ alkynyl).

In any of the above aspects, the compounds of the invention include lipid tail groups, where these groups do not include one or more biodegradable groups (e.g., one or more ester groups).

In any of the above aspects, the compounds of the invention includes two lipid tail groups having more than 11, 12, 13, 14, 15, 16, or 18 carbons (e.g., each $R^1$ and $R^2$ is, independently, optionally substituted $C_{17-24}$ alkenyl, optionally substituted $C_{15-24}$ alkynyl, optionally substituted $C_{15-24}$ heteroalkenyl, or optionally substituted $C_{15-24}$ heteroalkynyl; each $R^1$ and $R^2$ is, independently, optionally substituted $C_{16-24}$ alkenyl, optionally substituted $C_{16-24}$ alkynyl, optionally substituted $C_{16-24}$ heteroalkenyl, or optionally substituted $C_{16-24}$ heteroalkynyl; each $R^1$ and $R^2$ is, independently, optionally substituted $C_{17-24}$ alkenyl, optionally substituted $C_{17-24}$ alkynyl, optionally substituted $C_{17-24}$ heteroalkenyl, or optionally substituted $C_{17-24}$ heteroalkynyl; or each $R^1$ and $R^2$ is, independently, optionally substituted $C_{18-24}$ alkenyl, optionally substituted $C_{18-24}$ alkynyl, optionally substituted $C_{18-24}$ heteroalkenyl, or optionally substituted $C_{18-24}$ heteroalkynyl).

In any of the above aspects, the compounds of the invention do not contain a urea group (e.g., neither $R^3$ nor $R^4$ is an optionally substituted amide). In some embodiments, the compounds do not contain a carbamyl group. In some embodiments, the compounds do not contain more than one primary amine group (e.g., do not contain two primary amine groups or do not contain any primary amine groups in one or more of $R^1$-$R^6$, e.g., in either $R^3$ or $R^4$). In particular embodiments, the compounds include only one primary amine or no primary amines (e.g., only one primary amine or no primary amines are present in one or more of $R^1$-$R^6$, e.g., in either $R^3$ or $R^4$).

In any of the above aspects, the compounds of the invention do not contain a hydroxy group (e.g., neither $R^1$ nor $R^2$ is substituted with one, two, or three hydroxy groups; or neither $R^3$ nor $R^4$ is substituted with one, two, or three hydroxy groups). In some embodiments, when $R^1$ or $R^2$ is a saturated $C_{11-24}$ alkyl group (e.g., a saturated $C_{15}$ alkyl, a saturated $C_{16}$ alkyl, a saturated $C_{17}$ alkyl, or a saturated $C_{18}$ alkyl), $R^1$ and/or $R^2$ is not substituted with one, two, or three hydroxy groups. In some embodiments, when $R^1$ or $R^2$ is a saturated $C_{11-24}$ alkyl group (e.g., a saturated $C_{15}$ alkyl, a saturated $C_{16}$ alkyl, a saturated $C_{17}$ alkyl, or a saturated $C_{18}$ alkyl), $R^3$ and/or $R^4$ is not substituted with one, two, or three hydroxy groups.

In any of the above aspects, the compounds of the invention include no more than two amide groups (e.g., no more than two or one amide groups in the head group of the compound). In other embodiments, the compounds include zero, one, or two amide groups in one or more of $R^1$-$R^6$ (e.g., zero, one, or two amide groups in $R^3$ or $R^4$). In yet other embodiments, the compounds can include one, and only one, amide group (e.g., can include one, and only one, amide groups in $R^3$ or $R^4$). In further embodiments, the compounds include one, and only, amide group or no amide groups (e.g., include one, and only one, amide group or no amide groups in $R^3$ or $R^4$).

In any of the above aspects, the compounds of the invention exclude N-(4-N',N'-dimethylamino)butanoyl-(6Z,9Z,28Z,31Z)-heptatriaconta-6,9,28,31-tetraen-19-amine or N-(3-N',N'-dimethylamino)propanoyl-(6Z,9Z,28Z,31Z)-heptatriaconta-6,9,28,31-tetraen-19-amine, or salts thereof. In some embodiments, the compounds of the invention exclude N-methyl-N-(4-N',N'-dimethylamino)butanoyl-(6Z,9Z,28Z,31Z)-heptatriaconta-6,9,28,31-tetraen-19-amine or N-methyl-N-(3-N',N'-dimethylamino)propanoyl-(6Z,9Z,28Z,31Z)-heptatriaconta-6,9,28,31-tetraen-19-amine, or salts thereof.

In any of the above aspects, the compounds of the invention exclude N-(4-N',N'-dimethylamino)butanoyl-(6Z,9Z,28Z)-heptatriaconta-6,9,28-trien-19-amine, N-methyl-N-(4-N',N'-dimethylamino)butanoyl-(6Z,9Z,28Z)-heptatriaconta-6,9,28-trien-19-amine, N-(4-N',N'-dimethylamino)butanoyl-(6Z,9Z,28Z,31Z,34Z)-heptatriaconta-6,9,28,31,34-pentaen-19-amine, N-methyl-N-(4-N',N'-dimethylamino)butanoyl-(6Z,9Z,28Z,31Z,34Z)-heptatriaconta-6,9,28,31,34-pentaen-19-amine, N-(3-N',N'-dimethylamino)propanoyl-(6Z,9Z,28Z)-heptatriaconta-6,9,28-trien-19-amine, N-methyl-N-(3-N',N'-dimethylamino)propanoyl-(6Z,9Z,28Z)-heptatriaconta-6,9,28-trien-19-amine, N-(3-N',N'-dimethylamino)propanoyl-(6Z,9Z,28Z,31Z,34Z)-heptatriaconta-6,9,28,31,34-pentaen-19-amine, N-methyl-N-(3-N',N'-dimethylamino)propanoyl-(6Z,9Z,28Z,31Z,34Z)-heptatriaconta-6,9,28,31,34-pentaen-19-amine, or salts thereof.

In any of the above aspects, the compounds of the invention exclude di((Z)-non-2-en-1-yl) 9-((3-(dimethylamino)propanoyl)amino)heptadecanedioate, di((Z)-non-2-en-1-yl) 9-((4-(dimethylamino)butanoyl)amino)heptadecanedioate, di((Z)-non-2-en-1-yl) 9-((5-(dimethylamino)pentanoyl)amino)heptadecanedioate, or salts thereof.

In any of the above aspects, the compounds of the invention has a pKa value less than 6.2 and more than 6.5 (e.g., a pKa value between 4.0 and 6.2, such as between 4.0 and 5.2, between 4.0 and 5.6, or between 4.0 and 5.8; or between 6.5 and 8.5, e.g., between 6.5 and 7.0, between 6.5 and 7.5, or between 6.5 and 8.0). In particular embodiments, the pKa value is between about 5.0 and about 6.0 (e.g., between 5.0 and 5.5, between 5.0 and 5.6, between 5.0 and 5.7, between 5.0 and 5.8, between 5.0 and 5.9, between 5.0 and 6.0, between 5.2 and 5.5, between 5.2 and 5.6, between 5.2 and 5.7, between 5.2 and 5.8, between 5.2 and 5.9, between 5.2 and 6.0, between 5.4 and 5.5, between 5.4 and 5.6, between 5.4 and 5.7, between 5.4 and 5.8, between 5.4 and 5.9, between 5.4 and 6.0, between 5.6 and 5.7, between 5.6 and 5.8, between 5.6 and 5.9, or between 5.6 and 6.0). The pKa value can be determined by any useful method, e.g., measuring fluorescence of 2-(p-toluidino)-6-naphthalene sulfonic acid (TNS), zeta potential measurements, etc. In particular embodiments, the pKa value is the ratio of the concentration of charged cationic lipid and the concentration of uncharged lipid (e.g., as measured by in situ TNS fluorescence titration, where pKa is defined as the pH at half-maximal fluorescence intensity).

DETAILED DESCRIPTION

Figure 1:
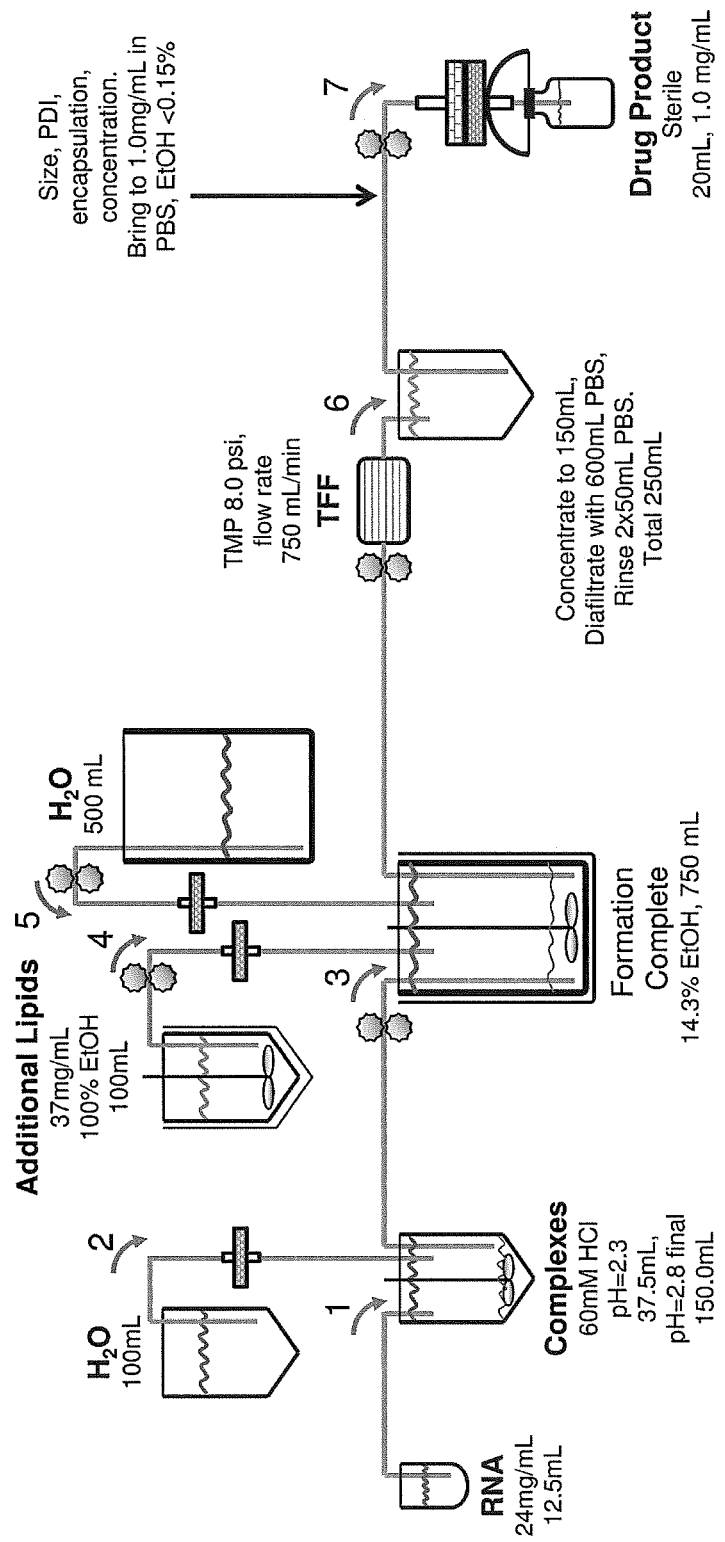
FIG. 1 illustrates an exemplary manufacturing process for an anionic agent-comprising particle of the instant invention. Performance of the process involves initially combining a lipid complex suspended in an acidic aqueous solution (here, 60 mM HCl at pH 2.3) and anionic agent (here, RNA dissolved in water), diluting such solution with water, then adding a lipidic solution dissolved in a solvent (here, ethanol) to the complex-anionic agent mixture, thereby producing particles comprising the anionic agent. Particles thus formed are then diluted in an additional volume of water and are optionally then subjected to filtration (here, tangential flow filtration (TFF)) to remove solvent and concentrate the particles prior to use.

The present invention is directed to processes for formulation of anionic agents, performance of which enhance the probability that such anionic agents achieve intracellular localization upon administration to mammalian cells and/or mammals.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" means±10% of the recited value.

As used herein, the term "acidic aqueous solution" is intended to mean an aqueous solution of pH 1.0 to pH 6.9, preferably of pH 2.0 to pH 4.0, which has a molarity of 5 to 200 mM, optionally 20 to 100 mM or 40 to 80 mM. The acidic aqueous solution may be selected from aqueous solutions of hydrochloric acid, citric acid, acetic acid and other acids. The type and pH of acidic aqueous solution will vary depending on the type of lipid and/or anionic agent to be suspended or dissolved in such solution.

By "alkenyl" is meant a monovalent straight or branched chain group of, unless otherwise specified, from 2 to 24 carbon atoms containing one or more carbon-carbon double bonds. Alkenyl groups are exemplified by ethenyl, 1-propenyl, 2-propenyl, 2-methyl-1-propenyl, 1-butenyl, 2-butenyl, oleyl, linoleyl, linolenyl, and the like. The term "$C_{x-y}$ alkenyl" represents alkenyl groups having between x and y carbons. Exemplary values for x are 2, 3, 4, 5, and 11; for y are 3, 4, 5, 6, and 24; and for x to y are 2 to 10, 2 to 9, 2 to 8, 2 to 7, 2 to 6, 2 to 5, 2 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20. In some embodiments, the alkenyl can be further substituted with 1, 2, 3, or 4 substituent groups as defined herein for an alkyl group.

By "alkyl" is meant a monovalent straight or branched saturated group of, unless otherwise specified, 1 to 24 carbon atoms. Alkyl groups are exemplified by methyl, ethyl, n-propyl, iso-propyl, n-butyl, sec-butyl, iso-butyl, tert-butyl, neopentyl, lauryl, myristyl, palmityl, stearyl, and the like, and may be optionally substituted with one, two, three, or, in the case of alkyl groups of two carbons or more, four substituents independently selected from the group consisting of: (1) alkoxy; (2) amino, as defined herein; (3) halo, such as F, Cl, Br, or I; (4) (heterocyclyl)oxy; (5) heterocyclyl; (6) alkyl; (7) alkenyl; (9) alkynyl; (10) cycloalkyl; (11) hydroxy; (12) nitro; or (13) oxo (e.g., carboxyaldehyde or acyl). In some embodiments, each of these groups can be further substituted as described herein. The term "$C_{x-y}$ alkyl" represents alkyl groups having between x and y carbons. Exemplary values for x are 1, 2, 3, 4, 5, and 11; for y are 2, 3, 4, 5, 6, and 24; and for x to y are 1 to 10, 1 to 9, 1 to 8, 1 to 7, 1 to 6, 1 to 5, 1 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20.

The term "alkylene" and the prefix "alk-," as used herein, represent a polyvalent (e.g., divalent) hydrocarbon group derived from a straight or branched chain hydrocarbon by the removal of two hydrogen atoms. Alkylene groups are exemplified by methylene, ethylene, isopropylene, and the like. The term "$C_{x-y}$ alkylene" represent alkylene groups having between x and y carbons. Exemplary values for x are 1, 2, 3, 4, and 5, and exemplary values for y are 2, 3, 4, 5, and 6. In some embodiments, the alkylene can be further substituted with 1, 2, 3, or 4 substituent groups as defined herein for an alkyl group.

By "alkynyl" is meant a monovalent straight or branched chain group of, unless otherwise specified, from 2 to 24 carbon atoms containing one or more carbon-carbon triple bonds. Alkynyl groups are exemplified by ethynyl, 1-propynyl, and the like. The term "$C_{x-y}$ alkynyl" represents alkynyl groups having between x and y carbons. Exemplary values for x are 2, 3, 4, 5, and 11; for y are 3, 4, 5, 6, and 24; and for x to y are 2 to 10, 2 to 9, 2 to 8, 2 to 7, 2 to 6, 2 to 5, 2 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20. In some embodiments, the alkynyl can be further substituted with 1, 2, 3, or 4 substituent groups as defined herein for an alkyl group.

By "amide" is meant an amine group, as defined herein, attached to the parent molecular group through a carbonyl group.

By "amino," as used herein, is meant $-N(R^1)_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl or an N-protecting group, and wherein each $R^{N2}$ is, independently, H, alkyl, or aryl. In a preferred embodiment, amino is $-NH_2$, or $-NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl. By "primary amine" is meant a group having the structure $-NH_2$.

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group.

By "amount sufficient" of an agent is meant the amount of the agent sufficient to effect beneficial or desired results, such as clinical results, and, as such, an amount sufficient depends upon the context in which it is applied. For example, in the context of administering a formulation that reduces the expression level of a target gene, the amount sufficient of the formulation is an amount sufficient to achieve a reduction in the expression level of the target gene as compared to the response obtained without administration of the formulation.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, di stearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

As used herein, the term "anionic agent" refers to a chemical moiety comprising at least one negatively charged atom, which optionally may be incorporated into a formulation (e.g., as a payload). By "polyanionic payload" is meant a chemical moiety comprising multiple negatively charged atoms that may be incorporated into a formulation. Examples of a polyanionic payload include nucleic acids, RNAi agents, siRNA, dsRNA, miRNA, shRNA, DsiRNA, and antisense payloads.

By "anionic lipid" is meant any lipid molecule that has a net negative charge at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

As used herein, the term "antisense compound" or "antisense payload" encompasses, inter alfa, single-stranded antisense oligonucleotides (DNA, DNA-like, RNA, RNA-like) or certain double-stranded or self-hybridizing constructs comprising an antisense orientation oligonucleotide, antisense PNAs, ribozymes and external guide sequences (sequences that recruit RNase P, as described, e.g., in Guerrier-Takada et al., *Proc. Natl. Acad. Sci. USA* 94:8468, 1997). Antisense compounds can exert their effect by a variety of means. One such means is the antisense-mediated direction of an endogenous nuclease, such as RNase H in eukaryotes or RNase P in prokaryotes (Chiang et al., *J. Biol. Chem.* 1266:18162, 1991; Forster et al., *Science,* 249:783, 1990).

As used herein, the term "aqueous solution" refers to a composition comprising in whole, or in part, water.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma (HCC), secondary liver cancer (e.g., caused by metastasis of some other non-liver cancer cell type), and hepatoblastoma. As used herein, a "tumor" comprises one or more cancerous cells.

By "cationic lipid" is meant any lipid molecule that has a net positive charge at physiological pH. Exemplary cationic lipids include any described herein, e.g., in Table 1. In certain embodiments, the cationic lipid may comprise from about 20 mol % to about 50 mol % or about 40 mol % of the total lipid present in the particle.

As used herein, the term "carbamyl" refers to a carbamate group having the structure —NR$^{N1}$C(=O)OR or —OC(=O)N(R$^{N1}$)$_2$, where the meaning of each R$^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

By "cycloalkyl" is meant a monovalent saturated or partially unsaturated 3- to 10-membered monocyclic or polycyclic (e.g., bicyclic or tricyclic) hydrocarbon ring system. Examples include cyclopropyl, cyclobutyl, cyclopentyl, cyclohexyl, and cycloheptyl.

By "Dicer-substrate RNA" or "DsiRNA" is meant a class of 25+, e.g., 25-35 (e.g., 25-27, such as double stranded regions of 25 nucleotides in length) nucleotide double-stranded molecules that are capable of gene silencing. Due to its longer length compared to other RNAi agents, DsiRNA are likely substrates of Dicer.

By "double-stranded molecule" is meant a double-stranded RNA:RNA or RNA:DNA molecule that can be used to silence a gene product through RNA interference.

By "expression" is meant the detection of a gene or polypeptide by methods known in the art. For example, DNA expression is often detected by Southern blotting or polymerase chain reaction (PCR), and RNA expression is often detected by Northern blotting, RT-PCR, gene array technology, or RNAse protection assays. Methods to measure protein expression level generally include, but are not limited to, Western blotting, immunoblotting, enzyme-linked immunosorbent assay (ELISA), radioimmunoassay (MA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), and flow cytometry, as well as assays based on a property of the protein including, but not limited to, enzymatic activity or interaction with other protein partners.

The term "fusogenic" refers to the ability of a lipid particle, such as those described herein, to fuse with the membranes of a cell. The membranes can be either the plasma membrane or membranes surrounding organelles, e.g., endosome, nucleus, etc.

The term "halo," as used herein, represents a halogen selected from bromine, chlorine, iodine, or fluorine.

By "heteroalkenyl" is meant an alkenyl group, as defined herein, in which one or more of the constituent carbon atoms have each been replaced by O, N, or S. Exemplary heteroalkenyl groups include alkenyl groups, as described herein, substituted with an oxo group and/or attached to the parent molecular group through an oxygen atom. In some embodiments, the heteroalkenyl group can be further substituted with 1, 2, 3, or 4 substituent groups as described herein for alkyl groups.

By "heteroalkyl" is meant an alkyl group, as defined herein, in which one or more of the constituent carbon atoms have each been replaced by O, N, or S. Exemplary heteroalkyl groups include alkyl groups, as described herein, substituted with an oxo group and/or attached to the parent molecular group through an oxygen atom. In some embodiments, the heteroalkyl group can be further substituted with 1, 2, 3, or 4 substituent groups as described herein for alkyl groups.

The term "heteroalkylene," as used herein, refers to an alkylene group, as defined herein, in which 1 or 2 of the constituent carbon atoms have each been replaced by O, N, or S. In some embodiments, the heteroalkylene group can be further substituted with 1, 2, 3, or 4 substituent groups as described herein for alkylene groups. The term "$C_{x-y}$ heteroalkylene" represent heteroalkylene groups having between x and y carbons. Exemplary values for x are 1, 2, 3, 4, 5, and 11; for y are 2, 3, 4, 5, 6, and 24; and for x to y are 1 to 10, 1 to 9, 1 to 8, 1 to 7, 1 to 6, 1 to 5, 1 to 4, 10 to 24, 11 to 24, 12 to 24, 14 to 24, 16 to 24, 18 to 24, 10 to 22, 11 to 22, 12 to 22, 14 to 22, 16 to 22, 18 to 22, 10 to 20, 11 to 20, 12 to 20, 14 to 20, 16 to 20, or 18 to 20.

By "heteroalkynyl" is meant an alkynyl group, as defined herein, in which one or more of the constituent carbon atoms have each been replaced by O, N, or S. Exemplary heteroalkynyl groups include alkynyl groups, as described herein, substituted with an oxo group and/or attached to the parent molecular group through an oxygen atom. In some embodiments, the heteroalkynyl group can be further substituted with 1, 2, 3, or 4 substituent groups as described herein for alkyl groups.

The term "heteroaryl," as used herein, represents that subset of heterocyclyls, as defined herein, which are aromatic: i.e., they contain 4n+2 pi electrons within the mono- or multicyclic ring system. In some embodiment, the heteroaryl is substituted with 1, 2, 3, or 4 substituents groups as defined for a heterocyclyl group.

The term "heterocyclyl," as used herein represents a 3-, 4-, 5-, 6-, 7-, or 8-membered ring, unless otherwise specified, containing one, two, three, or four heteroatoms independently selected from the group consisting of nitrogen, oxygen, and sulfur. The heterocyclyl may be saturated or unsaturated and contain between 0 and 3 unsaturated bonds. For example, the 5-membered ring has zero to two double bonds, and the 6- and 7-membered rings have zero to three double bonds. Certain heterocyclyl groups include from 2 to 9 carbon atoms, e.g., from 3 to 7 carbon atoms. Other such groups may include up to 12 carbon atoms. The term "heterocyclyl" also represents a heterocyclic compound having a bridged multicyclic structure in which one or more carbons and/or heteroatoms bridges two non-adjacent members of a monocyclic ring, e.g., a quinuclidinyl group. Examples of heterocyclic groups include aziridinyl, azetidinyl, pyrrolinyl, pyrrolyl, pyrrolidinyl, pyrazolyl, pyrazolinyl, pyrazolidinyl, imidazolyl, imidazolinyl, imidazolidinyl, pyridyl, pyrimidinyl, piperidinyl, azepanyl, pyrazinyl, piperazinyl, diazepanyl, morpholinyl, tetrahydrofuranyl, dihydrofuranyl, and the like.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

By "hybridize" is meant to pair to form a double-stranded molecule between sufficiently complementary polynucleotides, as defined herein, or portions thereof, under various conditions of stringency. (See, e.g., Wahl et al., *Methods Enzymol.* 152:399 (1987); Kimmel, *Methods Enzymol.* 152: 507 (1987)). For example, high stringency salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. High stringency temperature conditions will ordinarily include temperatures of at least about 30° C., 37° C., or 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In an alternative embodiment, hybridization will occur at 50° C. or 70° C. in 400 mM NaCl, 40 mM PIPES, and 1 mM EDTA, at pH 6.4, after hybridization for 12-16 hours, followed by washing. Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. Useful variations on these conditions will be readily apparent to those skilled in the art. One such exemplary variation includes assessment of hybridization under conditions designed to mimic physiological intracellular conditions, wherein cations and anions are assorted in the following proportions: for cations, Sodium:Potassium:Calcium:Magnesium at 10:160:2:26; and for anions, Chloride:Bicarbonate:Phosphate:Sulfate:Gluconate at 3:10:100:20:65.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "hydroxy," as used herein, represents an —OH group.

The term "lipid" refers to any fatty acid derivative which is capable of forming a micelle such that a hydrophobic portion of the lipid material is shielded from an aqueous phase/solution by a hydrophilic portion that orients toward the aqueous phase, or is capable of forming a bilayer such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups and such groups substituted by one or more aromatic, cycloaliphatic or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine could be used. Other compounds lacking in phosphorus, such as sphingolipid and glycosphingolipid families are also within the group designated as lipid. Additionally, the amphipathic lipids described above may be mixed with other lipids including triglycerides and sterols.

The term "lipid conjugate" refers to a conjugated lipid, optionally one that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides (see, e.g., U.S. Pat. No. 5,885,613), cationic PEG lipids, polyoxazoline (POZ)-lipid conjugates (e.g., POZ-DAA conjugates; see, e.g., U.S. Provisional Application No. 61/294,828, filed Jan. 13, 2010, and U.S. Provisional Application No. 61/295,140, filed Jan. 14, 2010), polyamide oligomers (e.g., ATTA-lipid conjugates), and mixtures thereof. Additional examples of POZ-lipid conjugates are described in PCT Publication No. WO 2010/006282. PEG or POZ can be conjugated directly to the lipid or may be linked to the lipid via a linker moiety. Any linker moiety suitable for coupling the PEG or the POZ to a lipid can be used including, e.g., non-ester containing linker moieties and ester-containing linker moieties. In certain embodiments, non-ester containing linker moieties, such as amides or carbamates, are used. The disclosures of each of the above patent documents are herein incorporated by reference in their entirety for all purposes. A conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl (Ci2), a PEG-dimyristyloxypropyl (Ci4), a PEG-dipalmitoyloxypropyl (Ci6), or a PEG-distearyloxypropyl (Ci8). In certain embodiments, a conjugated lipid that prevents aggregation of particles may be from 0 mol % to about 20 mol % or about 2 mol % of the total lipid present in the particle.

By "lipid vector" is meant a liposome, lipoplex, micelle, lipid nanoparticle, core-based particle, particle comprising an RNA binding agent-RNA aggregate which is combined with transfection lipid(s) or vesicle-based particle made by a process of the invention.

By "linker" is meant an optionally substituted polyvalent (e.g., divalent) group containing one or more atoms. Examples of linkers include optionally substituted alkylene and heteroalkylene groups, as described herein.

"Local delivery," as used herein, refers to delivery of an active agent such as an interfering RNA (e.g., DsiRNA) directly to a target site within an organism. For example, an agent can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

By "microRNA" (miRNA) is meant a single-stranded RNA molecule that can be used to silence a gene product through RNA interference.

The term "modified lipid" refers to lipids modified to aid in, for example, inhibiting aggregation and/or precipitation, inhibiting immune response and/or improving half-life in circulation in vivo. In certain aspects of the present invention, the modified lipids are neutral lipids. Modified neutral lipids include, but are not limited to, pegylated lipids, such as polyethyleneglycol 2000 distearoylphosphatidylethanolamine (PEG(2000) DSPE); PEG-DMG; PEG-DMPE; PEG-DPPE; PEG-DPG; PEG-DOPE; or PEG-DOG.

As used herein, a "modified lipid which prevents particle aggregation during lipid-anionic agent particle formation" is any modified lipid that provides a means for increasing circulation lifetime and/or increasing the delivery of the anionic agent-lipid particles to a target tissue. Exemplary such modified lipids include polyethylene glycol (PEG), PEG-ceramide, or ganglioside (e.g., GM1)-modified lipids. Typically, the concentration of the PEG, PEG-ceramide or ganglioside-modified lipids in the particle will be about 1-15%.

By "modulate" is meant that the expression of a gene, or level of an RNA molecule or equivalent RNA molecules encoding one or more proteins or protein subunits, or activity of one or more proteins or protein subunits is up-regulated or down-regulated, such that expression, level, or activity is greater than or less than that observed in the absence of the modulator. For example, the term modulate can include inhibition or gene silencing, and the level of expression of a gene or the level of an RNA molecule, or an equivalent thereof, is reduced by at least 10% (e.g., 15%, 20%, 25%, 30%, 35%, 40%, 50%, 60%, 70%, 80%, 85%, 90%, 95%, 97%, 98%, 99%, or 100%), as compared to a control.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

As used herein, the term "organic lipid solution" refers to a composition comprising in whole, or in part, an organic solvent having a lipid.

The term "oxo" as used herein, represents =O.

The term "urea" refers to a group having the structure $NR^{N1}C(=O)NR^{N1}$, where the meaning of each $R^{N1}$ is found in the definition of "amino" provided herein.

By "neutral lipid" is meant any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid. The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. In certain embodiments, the non-cationic lipid may be from about 5 mol % to about 90 mol %, about 10 mol %, or about 58 mol % if cholesterol is included, of the total lipid present in the particle. In some embodiments, the nucleic acid-lipid particle further includes cholesterol at, e.g., about 10 mol % to about 60 mol % or about 48 mol % of the total lipid present in the particle.

By "pharmaceutical composition" is meant a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

By "pharmaceutically acceptable excipient" is meant any ingredient other than the compounds described herein (for example, a vehicle capable of suspending or dissolving the active compound) and having the properties of being non-toxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

By "pharmaceutically acceptable salt" is meant those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharm. Sci.* 66(1):1, 1977 and in *Pharmaceutical Salts: Properties, Selection, and Use*, P. H. Stahl and C. G. Wermuth (eds.), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, and the like.

By "RNA-binding agent" is meant any agent or combination of agents capable of binding or hybridizing a nucleic acid, e.g., a nucleic acid payload of a therapeutic formulation. RNA-binding agents include any lipid described herein (e.g., one or more cationic lipids, combinations of one or more cationic lipids, such as those described herein or in Table 1, as well as combinations of one or more cationic lipids and any other lipid, such as neutral lipids or PEG-lipid conjugates). The RNA-binding agent can form any useful structure within a formulation, such as an internal aggregate.

By "RNAi agent" is meant any agent or compound that exerts a gene silencing effect by hybridizing a target nucleic acid. RNAi agents include any nucleic acid molecules that are capable of mediating sequence-specific RNAi (e.g., under stringent conditions), for example, a short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and Dicer-substrate RNA (DsiRNA).

By "short hairpin RNA" or "shRNA" is meant a sequence of RNA that makes a tight hairpin turn and is capable of gene silencing.

By "sense region" is meant a nucleotide sequence of a nucleic acid of the invention having sufficient complementarity to an antisense region of another nucleic acid. In addition, the sense region of a nucleic acid of the invention can include a nucleotide sequence having homology with a target gene nucleotide sequence. By "antisense region" is meant a nucleotide sequence of a nucleic acid of the invention having sufficient complementarity to a target gene nucleotide sequence.

"Serum-stable" in relation to nucleic acid-lipid particles such as those described herein means that the particle is not significantly degraded after exposure to a serum or nuclease assay that would significantly degrade free DNA or RNA. Suitable assays include, for example, a standard serum assay, a DNAse assay, or an RNAse assay.

By "silencing" or "gene silencing" is meant that the expression of a gene or the level of an RNA molecule that encodes one or more proteins is reduced in the presence of an RNAi agent below that observed under control conditions (e.g., in the absence of the RNAi agent or in the presence of an inactive or attenuated molecule such as an RNAi molecule with a scrambled sequence or with mismatches). Gene silencing may decrease gene product expression by 1%, 2%, 3%, 4%, 5%, 6%, 7%, 8%, 9%, 10%, 15%, 20%, 25%, 30%, 35%, 40%, 50%, 60%, 70%, 80%, 85%, 90%, 95%, 97%, 98%, 99%, or 100% (i.e., complete inhibition).

By "small inhibitory RNA," "short interfering RNA," or "siRNA" is meant a class of 10-40 (e.g., 15-25, such as 21, or 25-35 and/or 25-30, such as 25, 26 or 27) nucleotide double-stranded molecules that are capable of gene silencing. Most notably, siRNA are typically involved in the RNA interference (RNAi) pathway by which the siRNA interferes with the expression of a specific gene product.

The term "solubility" refers to the quantity of a compound (the solute) that dissolves in a given quantity of solvent to form a saturated solution. A "solution" refers to a homogeneous mixture of a liquid (the solvent) with a gas or solid (the solute). In a solution the molecules of the solute are discrete and mixed with the molecules of the solvent. The solubility of a substance depends on the temperature. The "solubility in water" refers to the solubility of a solute in the solvent water.

By "subject" is meant either a human or non-human animal (e.g., a mammal).

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full-length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "sufficiently complementary" is meant a polynucleotide sequence that has the exact complementary polynucleotide sequence, as a target nucleic acid, or has a specified percentage or nucleotides that are the exact complement at the corresponding location within the target nucleic acid when the two sequences are optimally aligned. For example, a polynucleotide sequence that is "substantially complementary" to a target nucleic acid sequence has at least 50%, 60%, 70%, 75%, 80%, 85%, 90%, 95%, 96%, 97%, 98%, 99%, or 100% complementarity to the target nucleic acid sequence. For RNAi agents having a length between 10 to 40 nucleotides, sufficiently complementary sequences include those having one, two, three, four, or five non-complementary nucleotides. Indeed, in certain embodiments that include, e.g., DsiRNA agents, an active double-stranded RNAi agent can possess as few as 15 to 19 consecutive nucleotides of guide strand which are sufficiently complementary to a target nucleic acid, while there is no requirement for the remainder of the guide strand to possess any extent of complementarity with the target nucleic acid (though in certain embodiments, the remainder of the guide strand may partially or fully complementary with the nucleic acid (e.g., mRNA) that is targeted).

"Systemic delivery," as used herein, refers to delivery of lipid particles that leads to a broad biodistribution of an active agent such as an interfering RNA (e.g., DsiRNA) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

By "target nucleic acid" is meant any nucleic acid sequence whose expression or activity is to be modulated. The target nucleic acid can be DNA or RNA. In certain embodiments, the target nucleic acid is a target mRNA.

By "transfection lipid" is meant any lipid or combination of lipids capable of delivering a nucleic acid, e.g., a nucleic acid payload (optionally, the nucleic acid payload is in associated with an RNA binding agent, e.g., one or more cationic lipids) Transfection lipids include any lipid described herein (e.g., one or more cationic lipids, combinations of one or more cationic lipids, such as those described herein or in Table 1, as well as combinations of one or more cationic lipids and any other lipid or agent, such as neutral lipids, anionic lipids, PEG-lipid conjugates, or sterol derivatives). The transfection lipid or combinations including such a transfection lipid can form any useful structure within a formulation, such as an external, aggregate surface.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. By "treating cancer," "preventing cancer," or "inhibiting cancer" is meant causing a reduction in the size of a tumor or the number of cancer cells, slowing or inhibiting an increase in the size of a tumor or cancer cell proliferation, increasing the disease-free survival time between the disappearance of a tumor or other cancer and its reappearance, preventing or reducing the likelihood of an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay. Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after no less than 5, 10, 15, or 20 years. By "prophylactically treating" a disease or condition (e.g., cancer) in a subject is meant reducing the risk of developing (i.e., the incidence) of or reducing the severity of the disease or condition prior to the appearance of disease symptoms. The prophylactic treatment may completely prevent or reduce appears of the disease or a symptom thereof and/or may be therapeutic in terms of a partial or complete cure for a disease and/or adverse effect attributable to the disease. Prophylactic treatment may include reducing or preventing a disease or condition (e.g., preventing cancer) from occurring in an individual who may be predisposed to the disease but has not yet been diagnosed as having it.

Composition of Particles Comprising Anionic Agents

In some embodiments, a particle of the invention includes a cationic lipid (e.g., DODMA, DOTMA, DPePC, DODAP, or DOTAP), a neutral lipid (e.g., DSPC, POPC, DOPE, or SM), and, optionally, a sterol derivative (e.g., cholesterol; cholestanone; cholestenone; coprostanol; 3β-[-(N—(N',N'-dimethylaminoethane)-carbamoyl]cholesterol (DC-cholesterol); bis-guanidium-tren-cholesterol (BGTC); (2S,3S)-2-(((3S,10R,13R,17R)-10,13-dimethyl-17-(R)-6-methylheptan-2-yl)-2,3,4,7,8,9,10,11,12,13,14,15,16,17-tetradecahydro-1H-cyclopenta[a]phenanthren-3-yloxy)carbonylamino)ethyl 2,3,4,4-tetrahydroxybutanoate (DPC-1); (2S,3S)-((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4,4-tetrahydroxybutanoate (DPC-2); bis((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) 2,3,4-trihydroxypentanedioate (DPC-3); or 6-(((3S,10R,13R,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)oxidophosphoryloxy)-2,3,4,5-tetrahydroxyhexanoate (DPC-4)). In some embodiments, the particle further includes a PEG-lipid conjugate (e.g., PEG-DMG, PEG-DMPE, PEG-DPPE, PEG-DPG, PEG-DOPE, or PEG-DOG).

In some embodiments, the particle includes from about 10 mol % to about 40 mol % of one or more compounds of the invention (e.g., one or more of any compounds described herein, e.g., in Table 1), from about 10 mol % to about 40 mol % of one or more cationic lipids or one or more compounds of the invention (e.g., one or more of any compounds described herein, e.g., in Table 1), from about 1 mol % to about 20 mol % of one or more PEG-lipid conjugates, from about 5 mol % to about 20 mol % of one or more neutral lipids, and from about 20 mol % to about 40 mol % of one or more sterol derivatives.

In particular embodiments, the particle includes from about 10 mol % to about 80 mol % (e.g., from about 40 mol % to about 55 mol %, such as about 48 mol %) of one or more cationic lipids (e.g., compounds of the invention and/or other cationic lipids, as described herein), from about 1 mol % to about 20 mol % of one or more PEG-lipid conjugates, from about 5 mol % to about 20 mol % of one or more neutral lipids, and from about 20 mol % to about 40 mol % of one or more sterol derivatives. In some embodiments, the particle includes from about 10 mol % to about 30 mol % (e.g., about 22 mol %) of one or more compounds of the invention (e.g., L-6, L-30, and/or any described herein), from about 15 mol % to about 35 mol % (e.g., about 26 mol %) of one or more cationic lipids (e.g., DODMA or any described herein), from about 3 mol % to about 9 mol % (e.g., about 6 mol %) of one or more PEG-lipid conjugates (e.g., PEG-DSPE, PEG-DMPE, and/or any described herein), from about 10 mol % to about 20 mol % (e.g., about 14 mol %) of one or more neutral lipids (e.g., DSPC or any described herein), and from about 20 mol % to about 40 mol % (e.g., from about 29 mol % to about 33 mol %, such as about 33 mol %) of one or more sterol derivatives (e.g., cholesterol, a derivative thereof, or any described herein).

In some embodiments, one or more compounds of Table 1 is present in an amount between about 10 mol % to about 40 mol %, e.g., between about 10 mol % and about 15 mol %, between about 10 mol % and about 20 mol %, between about 10 mol % and about 25 mol %, between about 10 mol % and about 30 mol %, between about 10 mol % and about 35 mol %, between about 15 mol % and about 20 mol %, between about 15 mol % and about 25 mol %, between about 15 mol % and about 30 mol %, between about 15 mol % and about 35 mol %, between about 15 mol % and about 40 mol %, between about 20 mol % and about 25 mol %, between about 20 mol % and about 30 mol %, between about 20 mol % and about 35 mol %, between about 20 mol % and about 40 mol %, between about 25 mol % and about 30 mol %, between about 25 mol % and about 35 mol %, between about 25 mol % and about 40 mol %, between about 30 mol % and about 35 mol %, between about 30 mol % and about 40 mol %, or between about 35 mol % and about 40 mol % (e.g., about 21.0 mol %, 21.2 mol %, 21.4 mol %, 21.6 mol %, 21.8 mol %, 22 mol %, 25 mol %, 26 mol %, 26 mol %, 30 mol %, 35 mol %, or 40 mol %) of one or more compounds of Table 1. In some embodiments, one or more compounds of Table 1 is present in an amount between about 10 mol % to about 80 mol %, e.g., between about 10 mol % and about 15 mol %, between about 10 mol % and about 20 mol %, between about 10 mol % and about 25 mol %, between about 10 mol % and about 30 mol %, between about 10 mol % and about 35 mol %, between about 10 mol % and about 40 mol %, between about 10 mol % and about 45 mol %, between about 10 mol % and about 50 mol %, between about 10 mol % and about 55 mol %, between about 10 mol % and about 60 mol %, between about 10 mol % and about 65 mol %, between about 10 mol % and about 70 mol %, between about 10 mol % and about 75 mol %, between about 15 mol % and about 20 mol %, between about 15 mol % and about 25 mol %, between about 15 mol % and about 30 mol %, between about 15 mol % and about 35 mol %, between about 15 mol % and about 40 mol %, between about 15 mol % and about 45 mol %, between about 15 mol % and about 50 mol %, between about 15 mol % and about 55 mol %, between about 15 mol % and about 60 mol %, between about 15 mol % and about 65 mol %, between about 15 mol % and about 70 mol %, between about 15 mol % and about 75 mol %, between about 15 mol % and about 80 mol %, between about 20 mol % and about 25 mol %, between about 20 mol % and about 30 mol %, between about 20 mol % and about 35 mol %, between about 20 mol % and about 40 mol %, between about 20 mol % and about 45 mol %, between about 20 mol % and about 50 mol %, between about 20 mol % and about 55 mol %, between about 20 mol % and about 60 mol %, between about 20 mol % and about 65 mol %, between about 20 mol % and about 70 mol %, between about 20 mol % and about 75 mol %, between about 20 mol % and about 80 mol %, between about 25 mol % and about 30 mol %, between about 25 mol % and about 35 mol %, between about 25 mol % and about 40 mol %, between about 25 mol % and about 45 mol %, between about 25 mol % and about 50 mol %, between about 25 mol % and about 55 mol %, between about 25 mol % and about 60 mol %, between about 25 mol % and about 65 mol %, between about 25 mol % and about 70 mol %, between about 25 mol % and about 75 mol %, between about 25 mol % and about 80 mol %, between about 30 mol % and about 35 mol %, between about 30 mol % and about 40 mol %, between about 30 mol % and about 45 mol %, between about 30 mol % and about 50 mol %, between about 30 mol % and about 55 mol %, between about 30 mol % and about 60 mol %, between about 30 mol % and about 65 mol %, between about 30 mol % and about 70 mol %, between about 30 mol % and about 75 mol %, between about 30 mol % and about 80 mol %, between about 35 mol % and about 40 mol %, between about 35 mol % and about 45 mol %, between about 35 mol % and about 50 mol %, between about 35 mol % and about 55 mol %, between about 35 mol % and about 60 mol %, between about 35 mol % and about 65 mol %, between about 35 mol % and about 70 mol %, between about 35 mol % and about 75 mol %, or between about 35 mol % and about 80 mol %, between about 40 mol % and about 45 mol %, between about 40 mol % and about 50 mol %, between about 40 mol % and about 55 mol %, between about 40 mol % and about 60 mol %, between about 40 mol % and about 65 mol %, between about 40 mol % and about 70 mol %, between about 40 mol % and about 75 mol %, between about 40 mol % and about 80 mol %, between about 45 mol % and about 50 mol %, between about 45 mol % and about 55 mol %, between about 45 mol % and about 60 mol %, between about 45 mol % and about 65 mol %, between about 45 mol % and about 70 mol %, between about 45 mol % and about 75 mol %, or between about 45 mol % and about 80 mol %, between about 50 mol % and about 55 mol %, between about 50 mol % and about 60 mol %, between about 50 mol % and about 65 mol %, between about 50 mol % and about 70 mol %, between about 50 mol % and about 75 mol %, or between about 50 mol % and about 80 mol % (e.g., about 21.0 mol %, 21.2 mol %, 21.4 mol %, 21.6 mol %, 21.8 mol %, 22 mol %, 25 mol %, 26 mol %, 26 mol %, 30 mol %, 35 mol %, 40 mol %, 45 mol %, 48 mol %, 49 mol %, 50 mol %, 55 mol %, 60 mol %, 65 mol %, 70 mol %, or 75 mol %) of one or more compounds of Table 1.

In some embodiments, one or more cationic lipids is present in an amount between about 10 mol % to about 40 mol %, e.g., between about 10 mol % and about 15 mol %, between about 10 mol % and about 20 mol %, between about 10 mol % and about 25 mol %, between about 10 mol % and about 30 mol %, between about 10 mol % and about 35 mol %, between about 15 mol % and about 20 mol %, between about 15 mol % and about 25 mol %, between about 15 mol % and about 30 mol %, between about 15 mol % and about 35 mol %, between about 15 mol % and about 40 mol %, between about 20 mol % and about 25 mol %, between about 20 mol % and about 30 mol %, between about 20 mol % and about 35 mol %, between about 20 mol % and about 40 mol %, between about 25 mol % and about 30 mol %, between about 25 mol % and about 35 mol %, between about 25 mol % and about 40 mol %, between about 30 mol % and about 35 mol %, between about 30 mol % and about 40 mol %, or between about 35 mol % and about 40 mol % (e.g., about 25.1 mol %, 25.2 mol %, 25.3 mol %, 25.4 mol %, 25.5 mol %, 25.6 mol %, 25.7 mol %, 25.8 mol %, 25.9 mol %, 26.0 mol %, 26.2 mol %, 26.4 mol %, 26.6 mol %, 26.8 mol %, or 27 mol %) of one or more cationic lipids (e.g., DODMA or any described herein, such as in Table 1).

In some embodiments, one or more PEG-lipid conjugates is present in an amount between about 1 mol % to about 20 mol %, e.g., between about 1 mol % and about 5 mol %, between about 1 mol % and about 10 mol %, between about 1 mol % and about 15 mol %, between about 2 mol % and about 5 mol %, between about 2 mol % and about 10 mol %, between about 2 mol % and about 15 mol %, between about 2 mol % and about 20 mol %, between about 5 mol % and about 10 mol %, between about 5 mol % and about 15 mol %, between about 5 mol % and about 20 mol %, between about 10 mol % and about 15 mol %, between about 10 mol % and about 20 mol %, between about 15 mol % and about 20 mol % (e.g., about 2.5 mol %, 2.6 mol %, 2.7 mol %, 2.8 mol %, 2.9 mol %, 3 mol %, 3.5 mol %, 4 mol %, 4.3 mol %, 4.5 mol %, 4.7 mol %, 5 mol %, 5.3 mol %, 5.5 mol %, 5.7 mol %, 6 mol %, 6.5 mol %, 6.7 mol %, 7 mol %, 7.5 mol %, 8 mol %, 8.5 mol %, or 9 mol %) of one or more PEG-lipid conjugates (e.g., PEG-DSPE, PEG-DMPE, and/or any described herein).

In some embodiments, one or more neutral lipids is present in an amount between about 5 mol % to about 20 mol %, e.g., between about 5 mol % and about 10 mol %, between about 5 mol % and about 15 mol %, between about 5 mol % and about 20 mol %, between about 7 mol % and about 10 mol %, between about 7 mol % and about 15 mol %, between about 7 mol % and about 20 mol %, between about 10 mol % and about 15 mol %, between about 10 mol % and about 20 mol %, between about 15 mol % and about 20 mol % (e.g., about 13.0 mol %, 13.2 mol %, 13.4 mol %, 13.6 mol %, 13.8 mol %, 14 mol %, 14.1 mol %, 14.3 mol %, 14.5 mol %, 14.7 mol %, or 14.9 mol %) of one or more neutral lipids (e.g., DSPC or any described herein).

In some embodiments, one or more sterol derivatives is present in an amount between about 20 mol % to about 40 mol %, e.g., between about 20 mol % and about 25 mol %, between about 20 mol % and about 30 mol %, between about 20 mol % and about 35 mol %, between about 25 mol % and about 30 mol %, between about 25 mol % and about 35 mol %, between about 25 mol % and about 40 mol %, between about 30 mol % and about 35 mol %, between about 30 mol % and about 40 mol %, or between about 35 mol % and about 40 mol % (e.g., about 28.4 mol %, 28.6 mol %, 28.8 mol %, 29.0 mol %, 30 mol %, 31 mol %, 32 mol %, 33 mol %, 33.2 mol %, 33.4 mol %, 33.6 mol %, 33.8 mol %, 34 mol %, 34.4 mol %, 34.7 mol %, or 34.9 mol %) of one or more sterol derivatives (e.g., cholesterol or any described herein).

In some embodiments, the particle includes one or more lipid particles comprising one or more RNA-binding agents and one or more transfection lipids, where the one or more RNA-binding agents include from about 10 mol % to about 40 mol % of one or more cationic lipids or one or more compounds of Table 1 and from about 0.5 mol % to about 10 mol % of one or more PEG-lipid; and where the one or more transfection lipids include from about 10 mol % to about 40 mol % of one or more compounds of Table 1, from about 5 mol % to about 20 mol % of one or more neutral lipids, from about 0.5 mol % to about 10 mol % of one or more PEG-lipid conjugates, and from about 20 mol % to about 40 mol % of one or more sterol derivatives. Additional particles and percentages are as described herein.

In some embodiments, the particle further includes an anionic agent, e.g., a polyanionic agent such as an RNAi agent (e.g., dsRNA, siRNA, miRNA, shRNA, ptgsRNA, or DsiRNA, e.g., DsiRNA) or an antisense agent. In some embodiments, the RNAi agent has a length of 10 to 40 nucleotides, e.g., length of 10 to 15 nucleotides, 10 to 20 nucleotides, 10 to 25 nucleotides, 10 to 30 nucleotides, 10 to 35 nucleotides, 15 to 20 nucleotides, 15 to 25 nucleotides, 15 to 30 nucleotides, 15 to 35 nucleotides, 15 to 40 nucleotides, 16 to 20 nucleotides, 16 to 25 nucleotides, 16 to 30 nucleotides, 16 to 35 nucleotides, 16 to 40 nucleotides, 20 to 25 nucleotides, 18 to 20 nucleotides, 18 to 25 nucleotides, 18 to 30 nucleotides, 18 to 35 nucleotides, 18 to 40 nucleotides, 19 to 20 nucleotides, 19 to 25 nucleotides, 19 to 30 nucleotides, 19 to 35 nucleotides, 19 to 40 nucleotides, 20 to 30 nucleotides, 20 to 35 nucleotides, 20 to 40 nucleotides, 25 to 30 nucleotides, 25 to 35 nucleotides, 25 to 40 nucleotides, 30 to 35 nucleotides, 30 to 40 nucleotides, or 35 to 40 nucleotides, e.g., a length of 25 to 35 nucleotides, e.g., a length of 16 to 30 nucleotides, e.g., a length of 19 to 29 nucleotides. In some embodiments, the antisense agent has a length of 8 to 50 nucleotides (e.g., a length of 8 to 10 nucleotides, 8 to 15 nucleotides, 8 to 15 nucleotides, 8 to 20 nucleotides, 8 to 25 nucleotides, 8 to 30 nucleotides, 8 to 35 nucleotides, 8 to 40 nucleotides, or 8 to 45 nucleotides), e.g., a length of 14 to 35 nucleotides (e.g., a length of 14 to 15 nucleotides, 14 to 20 nucleotides, 14 to 25 nucleotides, or 14 to 30 nucleotides), e.g., a length of 17 to 24 nucleotides, e.g., a length of 17 to 20 nucleotides.

In some embodiments, the particle includes from about 1:10 (w/w) to about 1:100 (w/w) ratio of the anionic agent to the total lipid present in the particle, e.g., from about 1:10 (w/w) to about 1:15 (w/w) ratio, from about 1:10 (w/w) to about 1:20 (w/w) ratio, from about 1:10 (w/w) to about 1:40 (w/w) ratio, from about 1:10 (w/w) to about 1:50 (w/w) ratio, from about 1:10 (w/w) to about 1:60 (w/w) ratio, from about 1:10 (w/w) to about 1:70 (w/w) ratio, from about 1:10 (w/w) to about 1:80 (w/w) ratio, from about 1:10 (w/w) to about 1:90 (w/w) ratio, from about 1:10 (w/w) to about 1:95 (w/w) ratio, from about 1:20 (w/w) to about 1:40 (w/w) ratio, from about 1:20 (w/w) to about 1:50 (w/w) ratio, from about 1:20 (w/w) to about 1:60 (w/w) ratio, from about 1:20 (w/w) to about 1:70 (w/w) ratio, from about 1:20 (w/w) to about 1:80 (w/w) ratio, from about 1:20 (w/w) to about 1:90 (w/w) ratio, from about 1:20 (w/w) to about 1:95 (w/w) ratio, from about 1:20 (w/w) to about 1:100 (w/w) ratio, from about 1:40 (w/w) to about 1:50 (w/w) ratio, from about 1:40 (w/w) to about 1:60 (w/w) ratio, from about 1:40 (w/w) to about 1:70 (w/w) ratio, from about 1:40 (w/w) to about 1:80 (w/w) ratio, from about 1:40 (w/w) to about 1:90 (w/w) ratio, from about 1:40 (w/w) to about 1:95 (w/w) ratio, from about 1:40 (w/w) to about 1:100 (w/w) ratio, from about 1:50 (w/w) to about 1:60 (w/w) ratio, from about 1:50 (w/w) to about 1:70 (w/w) ratio, from about 1:50 (w/w) to about 1:80 (w/w) ratio, from about 1:50 (w/w) to about 1:90 (w/w) ratio, from about 1:50 (w/w) to about 1:95 (w/w) ratio, from about 1:50 (w/w) to about 1:100 (w/w) ratio, from about 1:60 (w/w) to about 1:70 (w/w) ratio, from about 1:60 (w/w) to about 1:80 (w/w) ratio, from about 1:60 (w/w) to about 1:90 (w/w) ratio, from about 1:60 (w/w) to about 1:95 (w/w) ratio, from about 1:60 (w/w) to about 1:100 (w/w) ratio, from about 1:80 (w/w) to about 1:90 (w/w) ratio, from about 1:80 (w/w) to about 1:95 (w/w) ratio, or from about 1:80 (w/w) to about 1:100 (w/w) ratio of the anionic agent to the total lipid present in the particle.

In some embodiments, the particle includes a liposome (e.g., a lipid nanoparticle), a lipoplex, or a micelle.

In one aspect, the process of the invention features a pharmaceutical composition including any compound described herein (e.g., one or more compound provided in Table 1), or a pharmaceutically acceptable salt thereof, or any particle or formulation described herein; and a pharmaceutically acceptable excipient.

In another aspect, the invention features a method of treating or prophylactically treating a disease in a subject, the method including administering to the subject a particle made by a process described herein (e.g., as set forth in the below Examples), any formulation described herein, or any composition described in an amount sufficient to treat the disease (e.g., liver cancer (e.g., hepatocellular carcinoma, hepatoblastoma, cholangiocarcinoma, angiosarcoma, or hemangiosarcoma), lung cancer (e.g., small cell lung cancer, non small cell lung cancer), prostate cancer, or neuroblastoma). The invention further features a method of treating or prophylactically treating neoplastic diseases and associated complications including, but not limited to, carcinomas (e.g., lung, breast, pancreatic, colon, hepatocellular, renal, female genital tract, prostate, squamous cell, carcinoma in situ), lymphoma (e.g., histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g., small cell lung cancer, non small cell lung cancer), breast, colon, bladder, prostate, gastrointestinal tract, endometrium, fallopian tube, testes and ovary, gastrointestinal stromal tumors (GISTs), prostate tumors, mast cell tumors (including canine mast cell tumors), acute myeloid myelofibrosis, leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g., sarcomas of neuroectodermal origin or leiomyosarcoma), metastasis of tumors to other tissues, and chemotherapy-induced hypoxia.

In another aspect, the invention features a method of modulating the expression of a target nucleic acid in a subject, the method including administering any particle made by a process described herein (e.g., as set forth in the below Examples), any formulation described herein, or any composition described in an amount sufficient to reduce the expression of the target gene (e.g., any described herein, e.g., one or more target genes selected from the group consisting of ABL1, AR, β-Catenin (CTNNB1), BCL1, BCL2, BCL6, CBFA2, CBL, CSF1R, ERBA1, ERBA2, ERBB1, ERBB2, ERBB3, ERBB4, ETS1, ETS2, ETV6, FGR, FOS, FYN, HCR, HRAS, JUN, KRAS, LCK, LYN, MET, MDM2, MLL1, MLL2, MLL3, MYB, MYC, MYCL1, MYCN, NRAS, PIM1, PML, RET, SRC, TAL1 TAL2, TCL3, TCL5, YES, BRCA1, BRCA2, MADH4, MCC, NF1, NF2, RB1, TP53, WT1, ApoB100, CSN5, CDK6, ITGB1, TGFβ1, Cyclin D1, hepcidin, PCSK9, TTR, PLK1, and KIF1-binding protein) in the subject (e.g., where the method includes reducing the expression of the target gene in the subject).

In another embodiment, the invention features the administration of a dosage of the particle/anionic agent of the invention to a subject one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month). A subject may receive dosages of the anionic agent in the range of about 0.0001 to about 10 mg/kg, e.g., about 0.0001 to about 1 mg/kg, about 0.0001 to about 5 mg/kg, about 0.001 to about 1 mg/kg, about 0.001 to about 5 mg/kg, about 0.001 to about 10 mg/kg, about 0.01 to about 1 mg/kg, about 0.01 to about 5 mg/kg, about 0.01 to about 10 mg/kg, about 1 to about 5 mg/kg, or about 1 to about 10 mg/kg, in any dosage regimen (e.g., one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month)).

In certain embodiments, a subject may receive dosages of a particle made by a process of the invention in the range of about 0.001 to about 200 mg/kg, e.g., about 0.001 to about 1 mg/kg, about 0.001 to about 10 mg/kg, about 0.001 to about 20 mg/kg, about 0.001 to about 50 mg/kg, about 0.001 to about 100 mg/kg, about 0.01 to about 1 mg/kg, about 0.01 to about 10 mg/kg, about 0.01 to about 20 mg/kg, about 0.01 to about 50 mg/kg, about 0.01 to about 100 mg/kg, about 0.01 to about 200 mg/kg, about 0.1 to about 1 mg/kg, about 0.1 to about 10 mg/kg, about 0.1 to about 20 mg/kg, about 0.1 to about 50 mg/kg, about 0.1 to about 100 mg/kg, about 0.1 to about 200 mg/kg, about 1 to about 10 mg/kg, about 1 to about 20 mg/kg, about 1 to about 50 mg/kg, about 1 to about 100 mg/kg, about 1 to about 200 mg/kg, about 10 to about 20 mg/kg, about 10 to about 50 mg/kg, about 10 to about 100 mg/kg, about 10 to about 200 mg/kg, about 20 to about 50 mg/kg, about 20 to about 100 mg/kg, or about 20 to about 200 mg/kg, in any dosage regimen (e.g., one or more times per day (e.g., 1, 2, 3, or 4 times per day), one or more times per week (e.g., 2, 3, 4, 5, 6, or 7 times per week) or one or more times per month (e.g., 2, 3, 4, 5, 6, 7, or 10 times per month)).

In another aspect, the invention features a method of delivering a particle/agent made by a process of the invention to a specific type of tissue. Examples of specific types of tissues to which the particle/agent may be delivered to include, but are not limited to, liver, pancreas, lung, prostate, kidney, bone marrow, spleen, thymus, lymph node, brain, spinal cord, heart, skeletal muscle, skin, oral mucosa, esophagus, stomach, ileum, small intestine, colon, bladder, cervix, ovary, testis, mammary gland, adrenal gland, adipose tissue (white and/or brown), blood (e.g., hematopoietic cells, such as human hematopoietic progenitor cells, human hematopoietic stem cells, CD34+ cells, CD4+ cells), lymphocytes, and other blood lineage cells.

Amino-Amine and Amino-Amide Lipids

Exemplary compounds employed in the processes of the invention are shown in Table 1.

TABLE 1

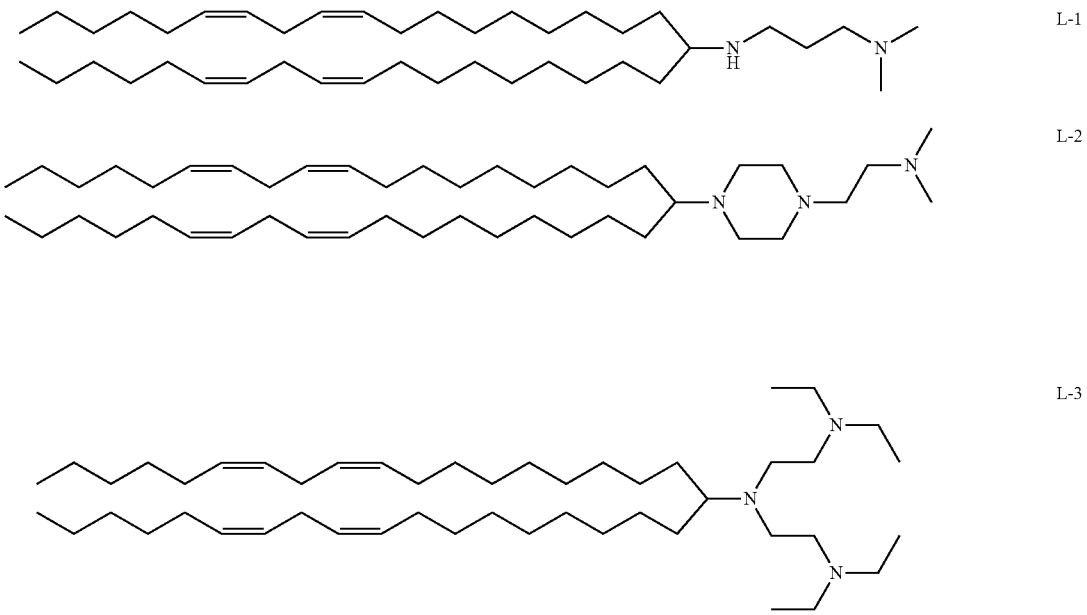

TABLE 1-continued
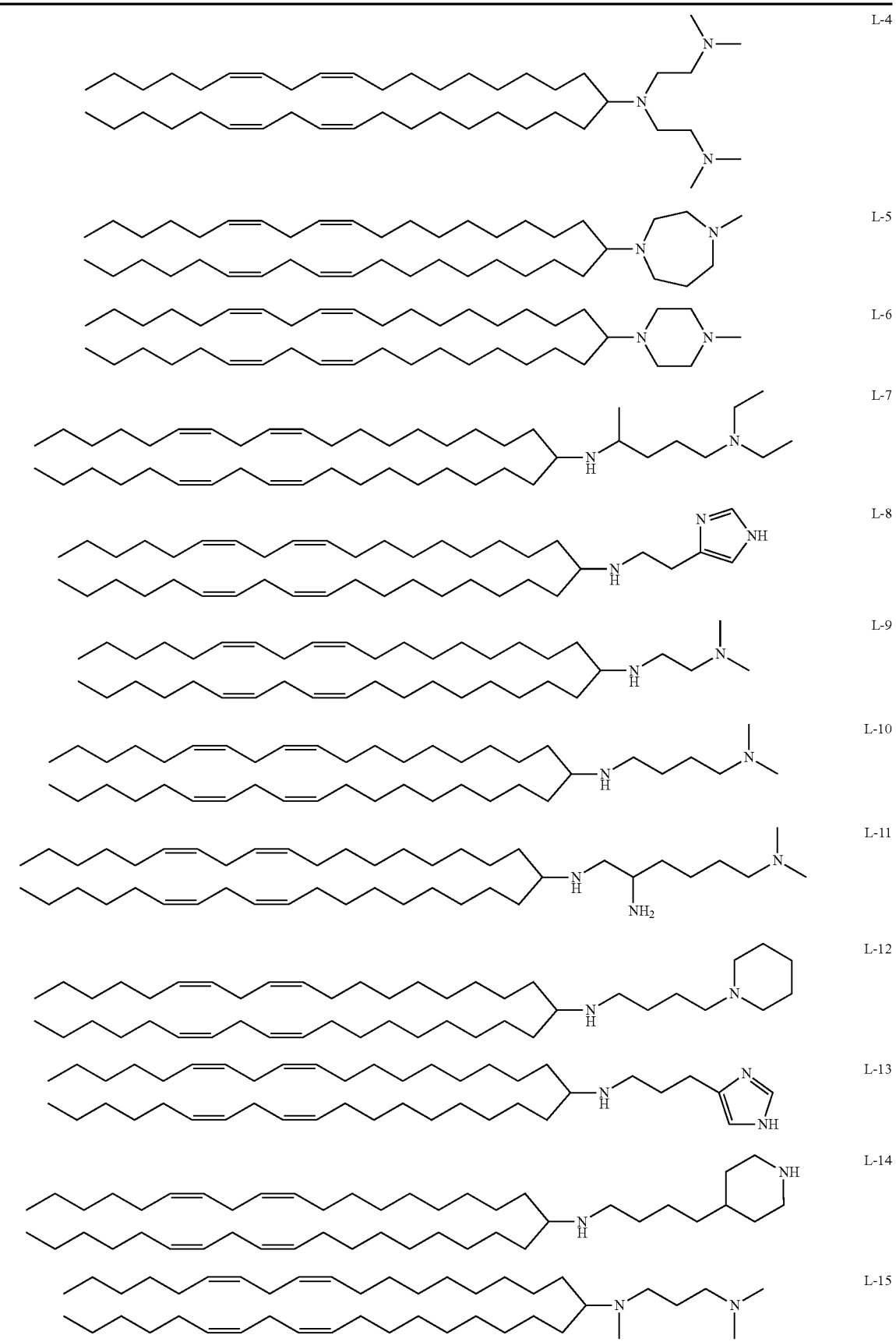

TABLE 1-continued
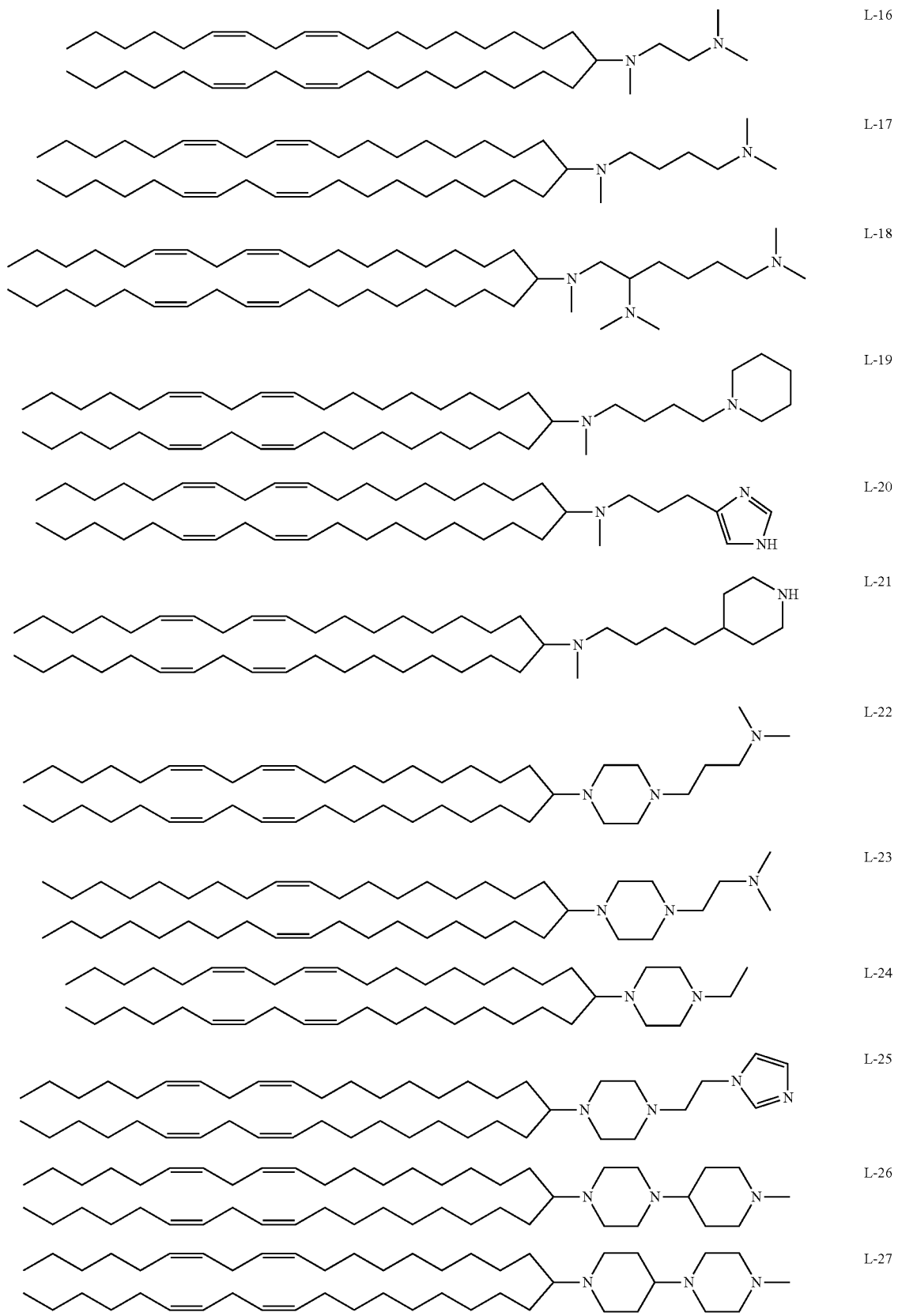

TABLE 1-continued

| | |
|---|---|
| (structure) | L-28 |
| (structure) | L-29 |
| (structure) | L-30 |
| (structure) | L-31 |
| (structure) | L-32 |
| (structure) | L-33 |
| (structure) | L-34 |
| (structure) | L-35 |
| (structure) | L-36 |
| (structure) | L-37 |
| (structure) | L-38 |

TABLE 1-continued
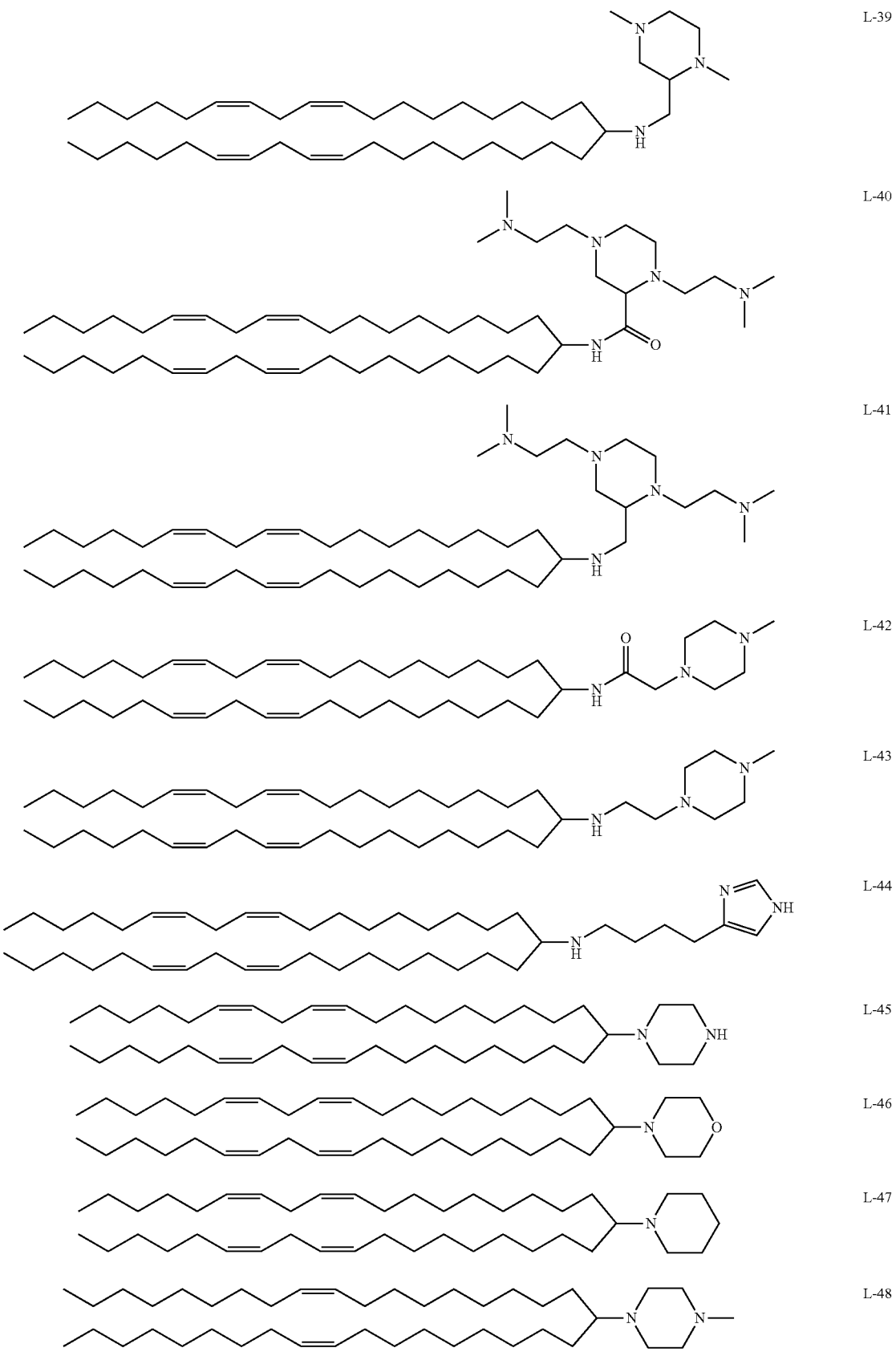

TABLE 1-continued

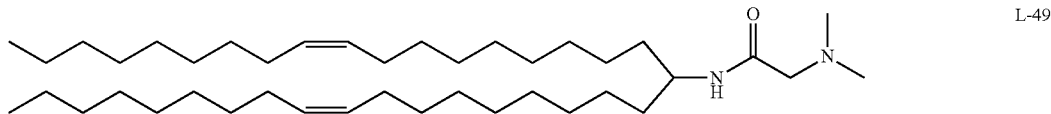

L-49

Certain compounds of the processes of the invention (e.g., as provided in Table 1) may be prepared by processes analogous to those established in the art, for example, by the reaction sequences shown in Schemes 1-4.

Scheme 1

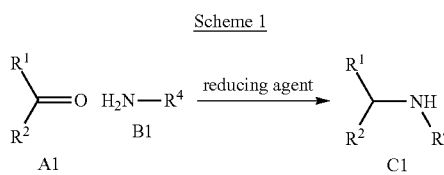

The secondary amine of formula C1 may be prepared under reductive amination conditions by treating ketone A1, where $R^1$ and $R^2$ is a lipid tail group, as described herein, with a primary amine B1, wherein $R^4$ is described herein. Conditions for reductive amination include combining ketone A1 and primary amine B1 with a reducing agent, such as sodium cyanoborohydride or sodium trioacetoxyborohydride, in an appropriate solvent. In particular embodiments, the amino-amine lipid of C1 is further oxidized to form a corresponding amino-amide lipid having an oxo group on the carbon in $R^3$ that is adjacent to the nitrogen. In other embodiments, the amino-amine lipid of C1 is further subject to alkylation at the nitrogen or on any carbon in $R^4$. Exemplary compounds that can be produced using this scheme are provided in Tables 1-4.

Scheme 2

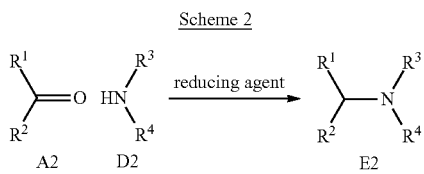

The tertiary amine of formula E2 may be prepared under reductive amination conditions by treating ketone A2, where each $R^1$ and $R^2$ is a lipid tail group, as described herein, with a secondary amine D2, where $R^3$ and $R^4$ is described herein. Conditions for reductive amination include combining ketone A2 and secondary amine D2 with a reducing agent, such as sodium cyanoborohydride or sodium trioacetoxyborohydride, in an appropriate solvent. In some embodiments of D2, $R^3$ and $R^4$ join to form a heterocyclic ring containing one or more heteroatoms, and the resultant tertiary amine E2 includes such $R^3$ and $R^4$ groups. In particular embodiments, the amino-amine lipid of E2 is further oxidized to form a corresponding amino-amide lipid having an oxo group on a carbon in $R^3$ or $R^4$ that is adjacent to the nitrogen. In other embodiments, the amino-amine lipid of E2 is further subject to alkylation on any carbon in $R^3$ and/or $R^4$.

Scheme 3

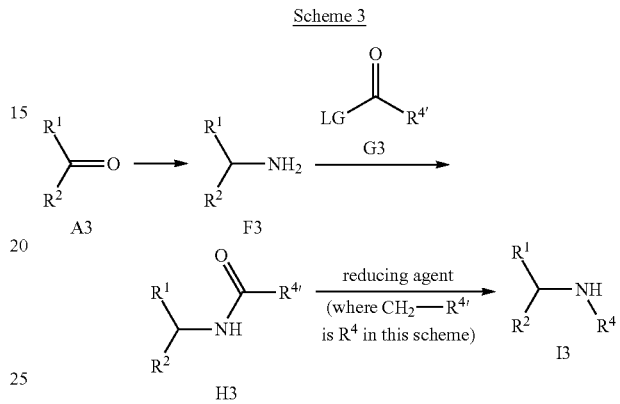

The amine of formula F3 may be prepared by combining ketone A3, ammonia, dihydrogen, and a catalyst in an appropriate solvent, optionally, under high pressure. The amino-amide lipid of formula H3 may be prepared by combining amine F3 with an activated carboxylic acid G3 in an appropriate solvent, where LG is a leaving group and $R^4$ is described herein. Exemplary LG's include halo (e.g., chloride, bromine, or iodine), tosylate, and triflate. The amino-amine lipid of I3 may be prepared by combining amide H3 with a reducing agent (e.g., lithium aluminum hydride, borane-tetrahydrofuran, or borane-dimethylsulfide). In particular embodiments, the amino-amide lipid of H3 is further subject to alkylation at the nitrogen or on any carbon in $R^4$. In other embodiments, the amino-amine lipid of I3 is further subject to alkylation at the nitrogen or on any carbon in $R^4$.

Scheme 4

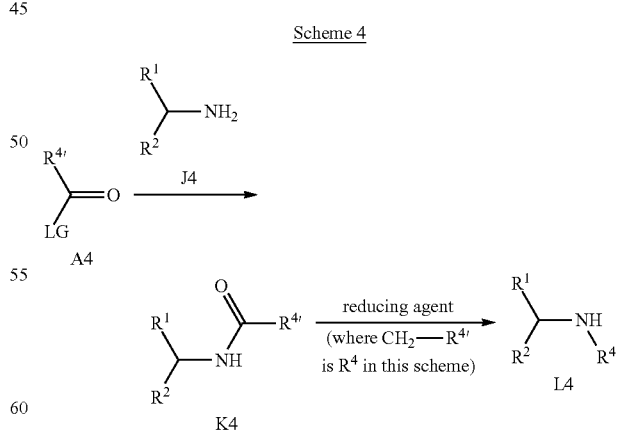

The amino-amide lipid of formula K4 may be prepared by combining ketone A4 and amine J4 in an appropriate solvent, where LG is a leaving group and $R^1$, $R^2$, and $R^4$ are described herein. Exemplary LG's include halo (e.g., chloride, bromine, or iodine), tosylate, and triflate. The amino-amine lipid of L4 may be prepared by combining amide K4 with a reducing agent (e.g., lithium aluminum hydride, borane-tetrahydrofuran, or borane-dimethylsulfide). In other embodiments, the amino-amide lipid of K4 is further subject to alkylation at the nitrogen or on any carbon in $R^{4'}$. In other embodiments, the amino-amine lipid of L4 is further subject to alkylation at the nitrogen or on any carbon in $R^4$.

In any of the above schemes, $R^4$ can be optionally substituted heterocyclyl, optionally substituted $-L^1-NR^5R^6$, optionally substituted $-C(O)L^1-NR^5R^6$, or optionally substituted $-L^1$-heterocyclyl, as described herein.

In any of the above schemes, the compounds can be further alkylated to introduce an optionally substituted $C_{1-6}$ alkyl on N (i.e., $R^3$ is an optionally substituted $C_{1-6}$ alkyl) to form a tertiary amine.

Any of the lipids described herein, e.g., as in Table 1, can be produced by applying the synthetic schemes provided above, synthetic schemes disclosed in the art and, if needed, by making modifications known to one skilled in the art.

Lipid Head Groups

Compounds employed in the processes of the invention may include a lipid head group, a headpiece, and one or more lipid tail groups. The headpiece, e.g., >CH—, connects the head group to the tail group(s). In particular embodiments, the head group includes two or more nitrogen atoms. Any of the head groups described herein, e.g., in Tables 2 or 3, may be optionally substituted with one or more substituents (e.g., one or more substituents described herein for alkyl).

A non-limiting list of head groups having an amine group is provided in Table 2. Any of the head groups described herein, e.g., head groups H-1 to H-39 in Table 2, can be combined with any of the tail groups described herein, e.g., in Table 4, via headpiece >CH— to form a compound of the invention.

TABLE 2

Examples of lipid head groups

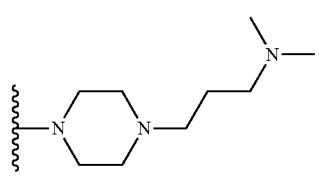 [SMILES: *N1CCN(CCCN(C)C)CC1] (H-1)

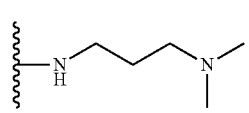 [SMILES: *NCCCN(C)C] (H-2)

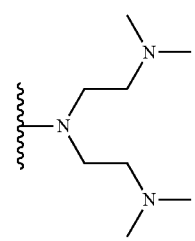 [SMILES: *N(CCN(C)C)CCN(C)C] (H-3)

TABLE 2-continued

Examples of lipid head groups

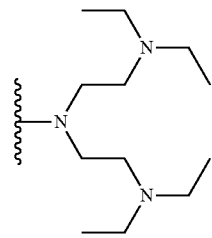 [SMILES: *N(CCN(CC)CC)CCN(CC)CC] (H-4)

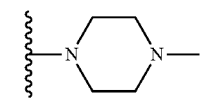 (H-5)

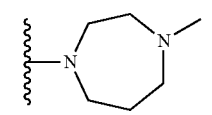 (H-6)

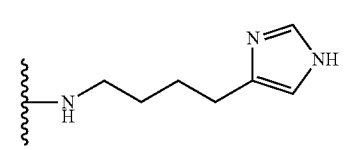 [SMILES: *NCCCCc1c[nH]cn1] (H-7)

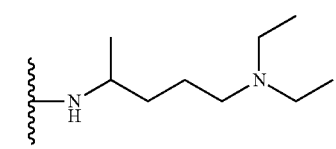 [SMILES: *NC(C)CCCN(CC)CC] (H-8)

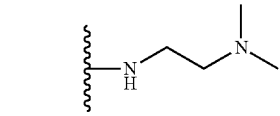 [SMILES: *NCCN(C)C] (H-9)

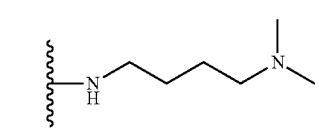 [SMILES: *NCCCCN(C)C] (H-10)

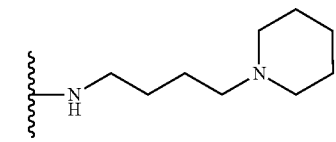 [SMILES: *NCCCCN1CCCCC1] (H-11)

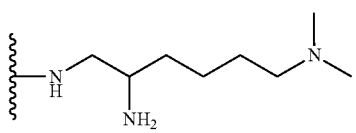 [SMILES: *NCC(N)CCCCN(C)C] (H-12)

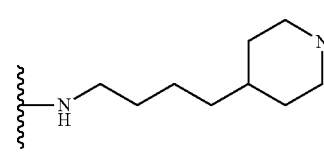 (H-13)

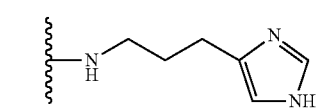 [SMILES: *NCCCc1c[nH]cn1] (H-14)

TABLE 2-continued
Examples of lipid head groups
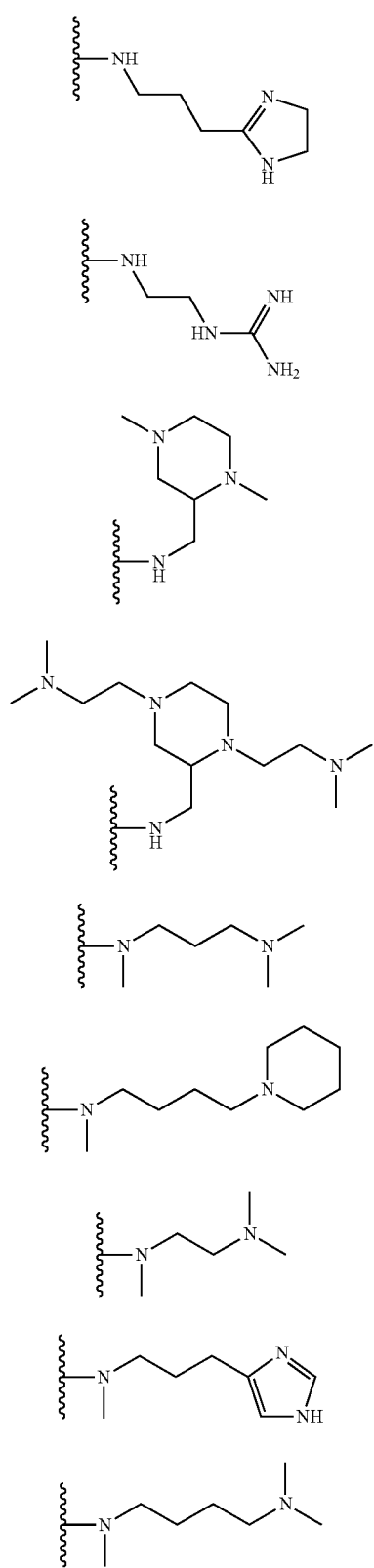
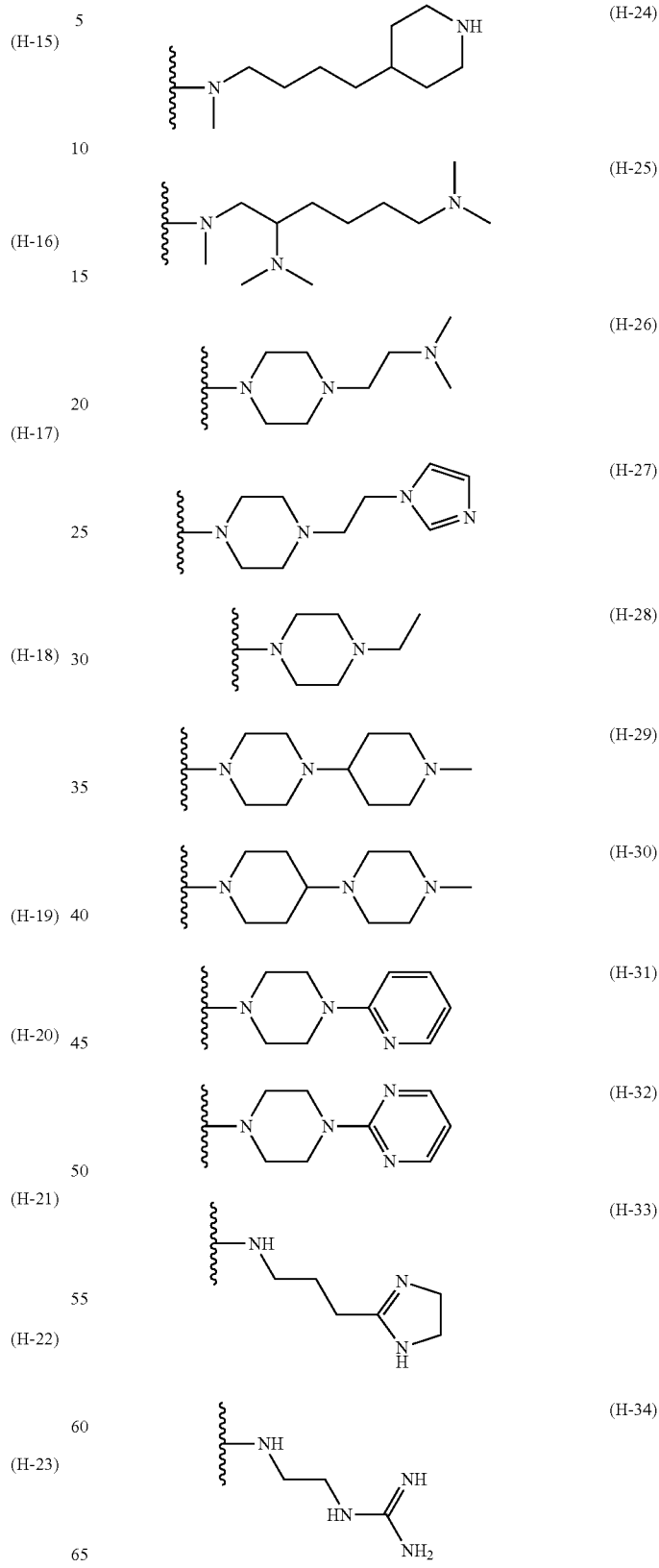

TABLE 2-continued

Examples of lipid head groups (H-35)
(H-36)
(H-37)
(H-38)
(H-39)

A non-limiting list of head groups having an amide group is provided in Table 3. Any of the head groups described herein, e.g., head groups H-40 to H-52 in Table 3, can be combined with any of the tail groups described herein, e.g., in Table 4, via headpiece >CH— to form a compound for use in the processes of the invention.

TABLE 3

Examples of lipid head groups containing an amide (H-40)
(H-41)
(H-42)
(H-43)
(H-44)
(H-45)
(H-46)
(H-47)
(H-48)
(H-49)
(H-50)
(H-51)

TABLE 3-continued

Examples of lipid head groups containing an amide

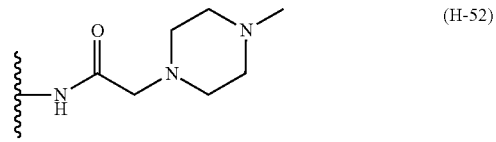
(H-52)

Lipid Tail Groups

As described herein, the compounds used in the processes of the invention generally include one or more tail groups that can optionally include one or more heteroatoms. For each compound, the tail groups can be the same or different. Any of the tail groups described herein, e.g., in Table 4, may be optionally substituted with one or more substituents (e.g., one or more substituents described herein for alkyl).

Exemplary tail groups include saturated and unsaturated groups having carbon or one or more heteroatoms (e.g., O), such as linolenyl (C18:3), linolenyloxy (C18:3), linolenoyl (C18:3), linoleyl (C18:2), linoleyloxy (C18:2), and linoleoyl (C18:2); and any heteroatomic tail group described herein that is connected to the headpiece by a methylene, e.g., tail groups selected from the group of linolenyloxymethylene (C18:3), linolenoylmethylene (C18:3), and linoleyloxymethylene (C18:2), or linoleoylmethylene (C18:2). Additional non-limiting list of lipid tail groups is provided in Table 4.

TABLE 4

Examples of lipid tail groups

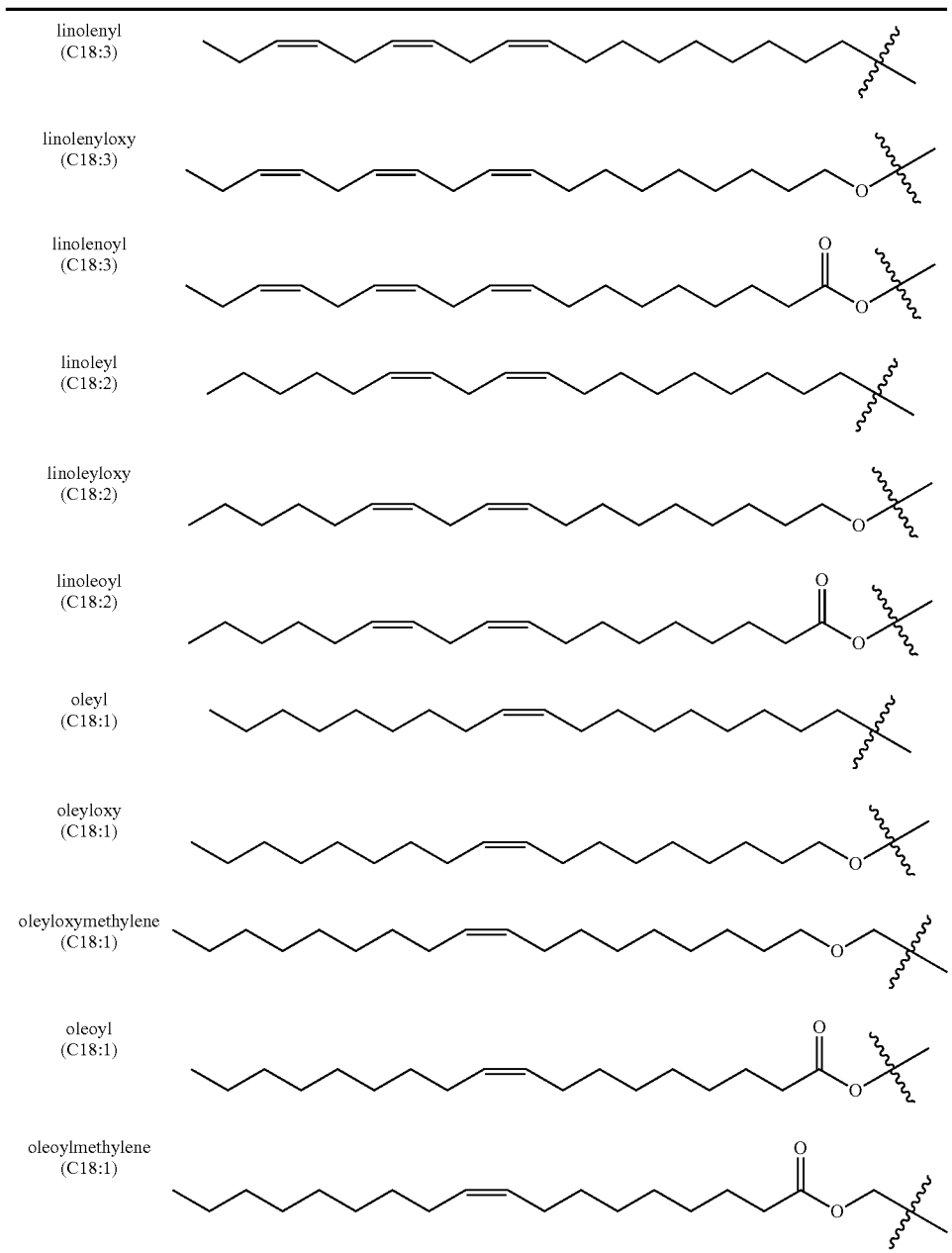

TABLE 4-continued

Examples of lipid tail groups

| | |
|---|---|
| stearyl (C18:0) | 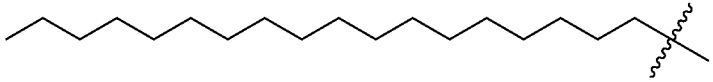 [SMILES: *CCCCCCCCCCCCCCCCCC] |
| stearyloxy (C18:0) | 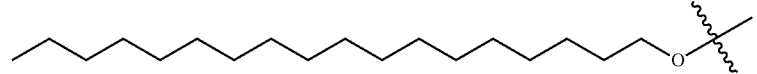 [SMILES: *OCCCCCCCCCCCCCCCCCC] |
| stearoyl (C18:0) | 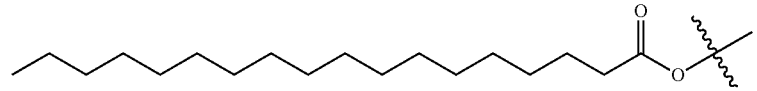 [SMILES: *OC(=O)CCCCCCCCCCCCCCCCC] |
| palmityl (16:0) | 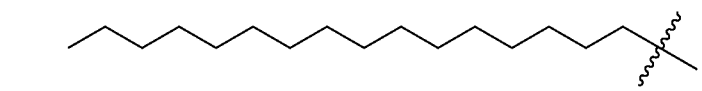 [SMILES: *CCCCCCCCCCCCCCCC] |
| palmityloxy (C16:0) | 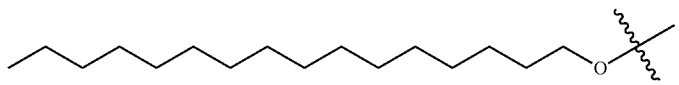 [SMILES: *OCCCCCCCCCCCCCCCC] |
| palmitoyl (C16:0) | 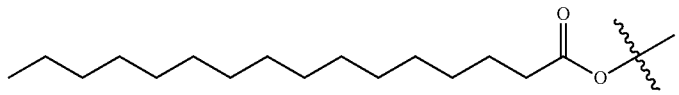 [SMILES: *OC(=O)CCCCCCCCCCCCCCC] |
| palmitoylmethylene (C16:0) | 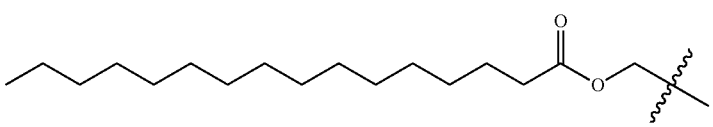 [SMILES: *COC(=O)CCCCCCCCCCCCCCC] |
| myristyl (14:0) | 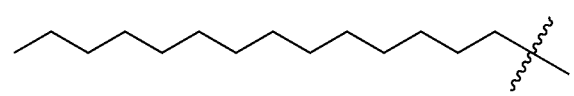 [SMILES: *CCCCCCCCCCCCCC] |
| myristyloxy (C14:0) | 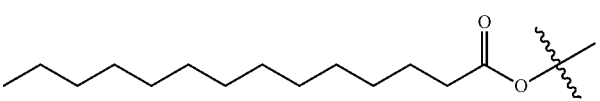 [SMILES: *OC(=O)CCCCCCCCCCCCC] |
| myristoyl (C14:0) |  |
| lauryl (12:0) | 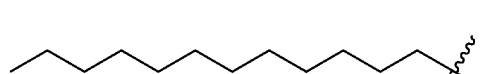 |
| lauryloxy (12:0) |  |
| lauryloyl (12:0) |  |

Measurement of pKa Values of Lipids in Assembled Nanoparticles

Different physiochemical properties of lipids greatly determine the behavior of lipids when present in different environments. One such important property is the ionization constant (Ka) of the lipid. The intrinsic pKa of the lipid may not be a correct representation of their behavior when present in an assembled nanoparticle. When present in an aqueous environment, the lipid experiences an environment with high dielectric constant, whereas in an assembled nanoparticle/vesicle, it is surrounded by lipids which provide low dielectric constant. In addition, the surrounding lipids, cholesterol, and PEGylated lipids all influence the apparent pKa of the formulation. The nature of interaction between the cationic lipids and nucleic acid being electrostatic, the apparent pKa of the formulation determines encapsulation of nucleic acid in the nanoparticle and also its subsequent intracellular release.

The TNS fluorescence method may be used to determine the apparent pKa of the lipid in the formulation. TNS (2-(p-toluidino)-6-naphthalene sulfonic acid) is a negatively charged fluorescent dye whose fluorescence is quenched in the presence of water. TNS partitions into a positively charged membrane and this results in an increase in fluorescence due to removal of water. The increase in the fluorescence can thus be used to estimate the ionization of a cationic lipid when present in different pH environment. Methods of determining pKa using TNS are known in the art.

Methods of Determining Solubility

The compounds used in the processes of the invention, as well as particles and compounds resulting from the processes of the invention, can be assessed to determine its solubility in a particular solvent. Compounds of the invention include but are not limited to any lipid molecule (e.g., cationic, anionic, or neutral lipid), sterol, component, particle, or combination thereof, as described herein.

Solubility can be measured by any useful method and/or by any useful metric. Exemplary methods and metrics include high performance liquid chromatography (optionally coupled with an evaporative light scattering detector), nuclear magnetic resonance, mass spectrometry, UV/VIS spectroscopy, and metrics such as the partition coefficient (Log P), solubility (e.g., as measured by g of solute per kg of solvent, g of solute per dL (100 mL) of solvent, molarity, molality, or mole fraction), critical micelle concentration, average particle size, size distribution of particles (e.g., as determined by the polydispersity index), homogeneity of the resultant solution, and encapsulation efficiency (e.g., of an anionic agent, such as any described herein, e.g., DsiRNA).

Formulations

The compounds used in the processes of the invention to synthesize particles and/or the particles may be combined with one or more lipid molecules (e.g., cationic, anionic, or neutral lipids) to produce a formulation, or the particles may be the formulation. The formulation can also include one or more components (e.g., sterol derivatives, PEG-lipid conjugates, polyamide-lipid conjugates, gangliosides, antioxidants, surfactants, amphiphilic agents, or salts) and/or one or more anionic agents (e.g., one or more nucleic acids or RNAi agents). Methods of formulating lipids to incorporate nucleic acid agents have been described, see, for example, Judge et al., *J. Clin. Invest.* 119(3):661, 2009; Noble et al., *Cancer Chemother. Pharmacol.* 64(4):741, 2009; Abrams et al., *Mol. Ther.* 18(1):171, 2009; Yagi et al., *Cancer Res.* 69(16):6531, 2009; Ko et al., *J. Control. Release* 133(2): 132, 2009; Mangala et al., *Methods Mol. Biol.* 555:29, 2009, which are hereby incorporated by reference.

Formulations with More than One Lipid Molecule

Formulations incorporating the particles of the processes of the invention may include any useful combination of lipid molecules (e.g., a compound as tabulated herein, a cationic lipid (optionally including one or more cationic lipids, e.g., one or more cationic lipids as described herein and/or optionally including one or more cationic lipids known in the art), a neutral lipid, an anionic lipid, and a PEG-lipid conjugate), including polypeptide-lipid conjugates and other components that aid in the formation or stability of a lipid vector, as described herein. The formulations incorporating the particles of the processes of the invention may include other components that aid in formation or stability.

The percentage of each component in the formulation can be balanced to produce a particle or lipid vector capable of encapsulating an anionic agent and transfecting the agent into a cell. An exemplary formulation includes from about 10 mol % to about 40 mol % of one or more compounds of Table 1, from about 10 mol % to about 40 mol % of one or more cationic lipids, from about 1 mol % to about 20 mol % of one or more PEG-lipid conjugates, from about 5 mol % to about 20 mol % of one or more neutral lipids, and from about 20 mol % to about 40 mol % of one or more sterol derivatives. In particular embodiments, the formulation includes from about 20 mol % to about 25 mol % (e.g., about 21.0 mol %, 21.2 mol %, 21.4 mol %, 21.6 mol %, 21.8 mol %, or 22 mol %) of one or more compounds of Table 1, from about 25 mol % to about 30 mol % (e.g., about 25.1 mol %, 25.2 mol %, 25.3 mol %, 25.4 mol %, 25.5 mol %, 25.6 mol %, 25.7 mol %, 25.8 mol %, 25.9 mol %, 26.0 mol %, 26.2 mol %, 26.4 mol %, 26.6 mol %, 26.8 mol %, or 27 mol %) of one or more cationic lipids (e.g., DODMA), from about 10 mol % to about 15 mol % (e.g., about 13.0 mol %, 13.2 mol %, 13.4 mol %, 13.6 mol %, 13.8 mol %, 14 mol %, 14.1 mol %, 14.3 mol %, 14.5 mol %, 14.7 mol %, or 14.9 mol %) of one or more neutral lipids (e.g., DSPC), from about 2.5 mol % to about 10 mol % (e.g., about 2.5 mol %, 2.6 mol %, 2.7 mol %, 2.8 mol %, 2.9 mol %, 3 mol %, 3.5 mol %, 4 mol %, 4.3 mol %, 4.5 mol %, 4.7 mol %, 5 mol %, 5.3 mol %, 5.5 mol %, 5.7 mol %, 6 mol %, 6.5 mol %, 6.7 mol %, 7 mol %, 7.5 mol %, 8 mol %, 8.5 mol %, or 9 mol %) of one or more PEG-lipid conjugates (e.g., about 2.8 mol %, 2.9 mol %, 3.0 mol %, 3.5 mol %, 3.7 mol %, 3.9 mol %, 4 mol %, 4.1 mol %, 4.3 mol %, 4.5 mol %, 4.7 mol %, 4.9 mol %, 5 mol %, 5.1 mol %, 5.3 mol %, 5.5 mol %, 5.7 mol %, 5.9 mol %, 6 mol %, 6.3 mol %, 6.5 mol %, 6.7 mol %, or 7 mol % of PEG2000-DSPE and/or PEG2000-DMPE and/or 3 mol %, 3.5 mol %, 3.7 mol %, 3.9 mol %, 4 mol %, 4.1 mol %, 4.3 mol %, 4.5 mol %, 4.7 mol %, 4.9 mol %, 5 mol %, 5.1 mol %, 5.3 mol %, 5.5 mol %, 5.7 mol %, 5.9 mol %, 6 mol %, 6.3 mol %, 6.5 mol %, 6.7 mol %, or 7 mol % of PEG2000-DMG), and about 25 mol % to about 35 mol % (e.g., about 28.4 mol %, 28.6 mol %, 28.8 mol %, 29.0 mol %, 30 mol %, 31 mol %, 32 mol %, 33 mol %, 33.2 mol %, 33.4 mol %, 33.6 mol %, 33.8 mol %, 34 mol %, 34.4 mol %, 34.7 mol %, or 34.9 mol %) of a sterol derivative (e.g., cholesterol).

The formulation can include any useful amount of one or more cationic lipids. In some embodiments, the content of the cationic lipid in the formulation is from about 10 mol % to about 40 mol % (e.g., from about 10 mol % to 15 mol %, from about 15 mol % to 20 mol %, from about 20 mol % to 25 mol %, from about 25 mol % to 30 mol %, from about 30 mol % to 35 mol %, and from about 35 mol % to 40 mol %). In particular embodiments, mixed cationic lipids (e.g., 10.8 mol % of L-1 and 10.8 mol % of L-2) are used.

In some embodiments, the formulation includes lipid particles having one or more RNA-binding agents and one or more transfection lipids, where the one or more RNA-binding agents include about 10 mol % to about 40 mol % of one or more cationic lipids (e.g., DODMA) and about 0.5 mol % to about 10 mol % of one or more PEG-lipid conjugates (e.g., PEG-DSPE, such as PEG2000-DSPE, and/or PEG-DMPE, such as PEG2000-DMPE); and where the one or more transfection lipids include about 10 mol % to about 40 mol % of one or more compounds of Table 1 (e.g., L-6, -30, or any in Table 1), about 5 mol % to about 20 mol % of one or more neutral lipids (e.g., DSPC), about 0.5 mol % to about 10 mol % of one or more PEG-lipid conjugates (e.g., PEG-DSPE, such as PEG2000-DSPE, and/or PEG- DMPE, e.g., PEG2000-DMPE), and about 20 mol % to about 40 mol % of one or more sterol derivatives (e.g., cholesterol).

The RNA-binding agent(s) of a lipid particle can include a combination of any useful lipids and conjugates. In particular embodiments, the content of the cationic lipid (e.g., DODMA) is from about 10 mol % to about 40 mol % (e.g., from about 20 mol % to 40 mol %, 20 mol % to 35 mol %, 20 mol % to 30 mol %, 15 mol % to 40 mol %, 15 mol % to 35 mol %, 15 mol % to 25 mol %, or 15 mol % to 20 mol %). In some embodiments, the PEG-lipid conjugate (e.g., PEG-DSPE, such as PEG2000-DSPE, and/or PEG-DMPE, such as PEG2000-DMPE) is from about 0.5 mol % to about 10 mol (e.g., from about 0.5 mol % to 1 mol %, 0.5 mol % to 5 mol %, 0.5 mol %, to 10 mol %, 1 mol % to 5 mol %, or 1 mol % to 10 mol %).

The transfection lipid(s) of a lipid particle can include a combination of any useful lipids and conjugates. In particular embodiments, the content of one or more compounds of Table 1 (e.g., L-6, -30, or any in Table 1) is from about 10 mol % to about 40 mol % (e.g., from about 10 mol % to 20 mol %, 10 mol % to 30 mol %, 10 mol % to 35 mol %, 15 mol % to 20 mol %, 15 mol % to 25 mol %, 15 mol % to 30 mol %, 15 mol % to 35 mol %, 15 mol % to 40 mol %, 20 mol % to 25 mol %, 20 mol % to 30 mol %, 20 mol % to 35 mol %, 20 mol % to 40 mol %, 25 mol % to 30 mol %, 25 mol % to 35 mol %, or 25 mol % to 40 mol %). In some embodiments, the content of one or more neutral lipids (e.g., DSPC) is about 5 mol % to about 20 mol % (e.g., from about 5 mol % to 10 mol %, 5 mol % to 15 mol %, 7 mol % to 10 mol %, 7 mol % to 15 mol %, 7 mol % to 20 mol %, 10 mol % to 15 mol %, or 10 mol % to 20 mol %). In some embodiments, the content of one or more PEG-lipid conjugates (e.g., PEG-DSPE, such as PEG2000-DSPE, and/or PEG-DMPE, such as PEG2000-DMPE) is about 0.5 mol % to about 10 mol % (e.g., from about 0.5 mol % to 1 mol %, 0.5 mol % to 5 mol %, 0.5 mol %, to 10 mol %, 1 mol % to 5 mol %, or 1 mol % to 10 mol %). In some embodiments, the content of one or more sterol derivatives (e.g., cholesterol) is about 20 mol % to about 40 mol % (e.g., from about 20 mol % to 25 mol %, 20 mol % to 30 mol %, 20 mol % to 35 mol %, 20 mol % to 40 mol %, 25 mol % to 30 mol %, 25 mol % to 35 mol %, or 25 mol % to 40 mol %).

In other embodiments, compounds selected from Table 1 are used in the formulation of the RNA-binding agent(s) (e.g., about 25.9 mol % of L-6, L-30, L-48, or L-49). In particular embodiments, the compound selected from Table 1 used in the formulation of the RNA-binding agent(s) is different from the compound (optionally from Table 1) used in the formulation of the transfection lipid(s) (e.g., 25.9 mol % L-48 as the RNA-binding agent, and 21.6 mol % L-30 as the transfection lipid). In some embodiments of the formulation, the one or more RNA-binding agents form an internal aggregate, and the one or more transfection lipids form an external, aggregate surface. In particular embodiments, the external, aggregate surface is not a membrane, a lipid bilayer, and/or a multilamellar layer.

The formulation can also include any useful amount of one or more PEG-lipid conjugates. In some embodiments, the content of the PEG-lipid conjugate in the formulation is from about 1 mol % and about 20 mol % (e.g., from about 1 mol % to about 2 mol %, from about 2 mol % to about 4 mol %, from about 2 mol % to about 7 mol %, from about 4 mol % to about 8 mol %, from about 8 mol % to about 12 mol %, from about 12 mol % to about 16 mol %, or from about 16 mol % to about 20 mol %). In other embodiments, the content of PEG-lipid conjugate is about 7 mol %, 6 mol %, 3.0 mol %, or 2.5 mol %. Moreover, the PEG-lipid content may be varied from about 1 mol % to about 20 mol %, by appropriate adjustment of the content of either DSPC or cholesterol, or both. The PEG-lipid may be varied by using C14:0 (as in Table 4, e.g., PEG-DSPE or PEG-DMPE, etc.), C16 (PEG-DPPE, PEG-DPG, etc.), C18:0 (PEG-DSPE, PEG-DSG, etc.), or C18:1 (PEG-DOPE, PEG-DOG, etc.). Furthermore, different molecular weight PEG moieties can be used (PEG2000, PEG3400, PEG5000, etc.). In particular embodiments, mixed PEG-conjugates are used, as described herein. In particular embodiments, PEG2000-DSPE is used. In particular embodiments, PEG2000-DMPE is used.

Formulations with RNAi Agents

The processes of the invention can be used to produce a particle and/or formulation containing an RNAi agent by any of the methods described herein. For example, see: Judge et al., *J. Clin. Invest.* 119(3):661, 2009; Noble et al., *Cancer Chemother. Pharmacol.* 64(4):741, 2009; Abrams et al., *Mol. Ther.* 18(1):171, 2009; Yagi et al., *Cancer Res.* 69(16):6531, 2009; Ko et al., *J. Control. Release* 133(2): 132, 2009; Mangala et al., *Methods Mol. Biol.* 555:29, 2009, which are hereby incorporated by reference.

The particle and/or formulation can include an RNAi agent and a lipid molecule and/or one or more components in any useful ratio. Exemplary ratios include from a (w/w) ratio of from about 1:10 to about 1:100 (w/w) (e.g., from about 1:10 to about 1:50, e.g., about 1:20) of RNAi agent: total lipid ratio, where the total lipid ratio is the weight of the combination of one or more lipid molecules (e.g., cationic, anionic, or neutral lipids) and one or more components (e.g., sterol derivatives, PEG-lipid conjugates, polyamide-lipid conjugates, gangliosides, antioxidants, surfactants, amphiphilic agents, or salts). In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The particle and/or formulation can include an RNAi agent in a dose ranging from about 1 mg/kg to about 10 mg/kg of any RNAi agent described here. Exemplary doses include 1 mg/kg, 2 mg/kg, 3 mg/kg, 4 mg/kg, 5 mg/kg, 6 mg/kg, 7 mg/kg, 8 mg/kg, 9 mg/kg, and 10 mg/kg of an RNAi agent in the particle or formulation.

Methods of Preparing Formulations

The particles of the invention can be prepared with a variety of useful processes. In one exemplary procedure, the components of the particles of the invention (e.g., one or more lipids) are dissolved in a solvent (e.g., an aqueous solvent, a non-aqueous solvent, or solvent mixtures thereof). Exemplary FDA-approved solvents for use in the processes of the invention include acetic acid, acetone, acetonitrile, anisole, benzene, 1-butanol, 2-butanol, butyl acetate, tert-butylmethyl ether, carbon tetrachloride, chlorobenzene, chloroform, cumene, cyclohexane, 1,2-dichloroethane, 1,1-dichloroethene, 1,2-dichloroethene, dichloromethane, 1,2-dimethoxyethane, n,n-dimethylacetamide, n,n-dimethylformamide, dimethyl sulfoxide, 1,4-dioxane, ethanol, 2-ethoxyethanol, ethyl acetate, ethyleneglycol, ethyl ether, ethyl formate, formamide, formic acid, heptane, hexane, isobutyl acetate, isopropyl acetate, methanol, 2-methoxyethanol, methyl acetate, 3-methyl-1-butanol, methylbutyl ketone, methylcyclohexane, methylethyl ketone, methylisobutyl ketone, 2-methyl-1-propanol, n-methylpyrrolidone, nitromethane, pentane, 1-pentanol, 1-propanol, 2-propanol, propyl acetate, pyridine, sulfolane, tetrahydrofuran, tetralin, toluene, 1,1,1-trichloroethane, 1,1,2-trichloroethene, xylene and combinations thereof. The resultant lipid suspension can be optionally filtered, mixed (e.g., batch mixed, in-line mixed, and/or vortexed), evaporated (e.g., using a nitrogen or argon stream), re-suspended (e.g., in an aqueous solvent, a non-aqueous solvent, or solvent mixtures thereof), freeze-thawed, extruded, and/or sonicated. Furthermore, the lipid suspension can be optionally processed by combining with any desired components (e.g., anionic agents (e.g., one or more RNAi agents), RNA-binding agents, transfection lipids, and/or any lipids described herein) to produce a final suspension. The one or more desired components can be provided in the same or different solvent as the suspension. For example, the lipid suspension can be provided in a first solvent or solvent system (e.g., an acidic aqueous solution such as water-HCl, or one or more aqueous or non-aqueous solvent(s), such as water, water-ethanol, buffer (e.g., phosphate buffered saline (PBS), Hank's balanced salt solution (HB SS), Dulbecco's phosphate-buffered saline (DPBS), Earle's balanced salt solution (EB SS), carbonate, lactate, ascorbate, and citrate, such as 5 mM, 10 mM, 50 mM, 75 mM, 100 mM, or 150 mM)), physiological osmolality solution (290 mOsm/kg, e.g., 0.9% saline, 5% dextrose, and 10% sucrose), saline, methanol, ethanol, n-propanol, isopropanol, n-butanol, isobutanol, tert-butanol, glycerol, ethylene glycol, propylene glycol, polyethylene glycol, chloroform, dichloromethane, hexane, cyclohexane, acetone, ether, diethyl ether, dioxan, isopropyl ether, tetrahydrofuran, or combinations thereof), and the anionic agent (e.g., RNAi agent) can be provided in a second solvent or solvent system e.g., one or more aqueous or non-aqueous solvent(s), such as water, water-HCl, water-ethanol, buffer (e.g., phosphate buffered saline (PBS), Hank's balanced salt solution (HBSS), Dulbecco's phosphate-buffered saline (DPBS), Earle's balanced salt solution (EBSS), carbonate, lactate, ascorbate, and citrate, such as 5 mM, 10 mM, 50 mM, 75 mM, 100 mM, or 150 mM)), physiological osmolality solution (290 mOsm/kg, e.g., 0.9% saline, 5% dextrose, and 10% sucrose), saline, methanol, ethanol, n-propanol, isopropanol, n-butanol, isobutanol, tert-butanol, glycerol, ethylene glycol, propylene glycol, polyethylene glycol, chloroform, dichloromethane, hexane, cyclohexane, acetone, ether, diethyl ether, dioxan, isopropyl ether, tetrahydrofuran, or combinations thereof). Exemplary concentrations of aqueous solvents and/or buffers include from about 4% to about 8% ethanol (e.g., from about 4% to 5%, 5% to 6%, 6%, to 7%, or 7% to 8%), from about 10 mM to about 100 mM citrate (e.g., from about 10 mM to 30 mM, 30 mM to 50 mM, 50 mM to 70 mM, 70 mM to 90 mM, or 90 mM to 100 mM). Any of the solvents or solvent systems can include one or more stabilizers, such as an antioxidant, a salt (e.g., sodium chloride), citric acid, ascorbic acid, glycine, cysteine, ethylenediamine tetraacetic acid (EDTA), mannitol, lactose, trehalose, maltose, glycerol, and/or glucose. In further examples, the one or more anionic agents are introduced into a lipid suspension using a first solvent or solvent system and then followed by addition of one or more additional lipids (e.g., transfection lipids) in a second solvent or solvent system, where first and second solvents or solvent systems are the same or different (e.g., the first solvent or solvent system is any described herein; and the second solvent or solvent system is any described herein). In particular embodiments, the second solvent or solvent system include one or more aqueous or non-aqueous solvents selected from the group consisting of saline, buffer (e.g., citrate or PBS), water, and ethanol. The final suspension can be optionally separated (e.g., by ultracentrifuge), mixed (e.g., batch mixed, in-line mixed, and/or vortexed), re-suspended, adjusted (e.g., with one or more solvents or buffer systems), sonicated, freeze-thawed, extruded, and/or purified.

Cationic Lipids

One or more cationic lipids can be included in the particles and/or formulations produced by the methods of the invention. In addition to the compounds of Table 1, other cationic lipids include, but are not limited to: N,N-dioleyl-N,N-dimethylammonium chloride (DODAC), 1,2-di-O-octadecenyl-3-trimethylammonium propane (DOTMA), N,N-distearyl-N,N-dimethylammonium (DDAB), 1,2-dioleoyl-3-trimethylammonium-propane (DOTAP, including chiral forms R-DOTAP and S-DOTAP), N-(1-(2,3-dioleyloxy)propyl)-N-2-(sperminecarboxamido)ethyl)-N,N-dimethylammonium (DOSPA), dioctadecylamidoglycyl carboxyspermine (DOGS), 1,2-dioleoyl-3-dimethylammonium propane (DODAP), N,N-dimethyl-(2,3-dioleyloxy)propylamine (DODMA), N-(1,2-dimyristyloxyprop-3-yl)-N,N-dimethyl-N-hydroxyethylammonium (DMRIE), 1,2-dilinoleyloxy-3-dimethylaminopropane (DLinDMA), 1,2-dilinolenyloxy-3-dimethylaminopropane (DLenDMA), 1,2-dilinoleoyl-3-dimethylaminopropane (DLinDAP), 1-linoleoyl-2-linoleyloxy-3-dimethylaminopropane (DLin-2-DMAP), 1,2-dilinoleylcarbamoyloxy-3-dimethylaminopropane (DLin-C-DAP), 1,2-dilinoleylthio-3-dimethylaminopropane (DLin-S-DMA), 2,2-dilinoleyl-4-dimethylaminomethyl-[1,3]-dioxolane (DLin-K-DMA), 2,2-dilinoleyl-4-(2-dimethylaminoethyl)[1,3]-dioxolane (DLin-KC2-DMA), (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl 4-(dimethylamino)butanoate (DLin-MC3-DMA), 1,2-dipalmitoyl-sn-glycero-O-ethyl-3-phosphocholine (DPePC), distearyldimethylammonium chloride (DSDMA), 1,2-dilauroyl-sn-glycero-3-ethylphosphocholine (12:0 EPC, e.g., or a chloride salt thereof), 1,2-dipalmitoyl-sn-glycero-3-ethylphosphocholine (16:0 EPC, e.g., or a chloride salt thereof), 1,2-distearoyl-sn-glycero-3-ethylphosphocholine (18:0 EPC, e.g., or a chloride salt thereof), 1,2-dioleoyl-sn-glycero-3-ethylphosphocholine (18:1 EPC, e.g., or a chloride salt thereof), dipalmitoyl phosphatidylethanolamidospermine (DPPES), dipalmitoyl phosphatidyl ethanolamido L-lysine (DPPEL), 1-[2-dioleoyloxy)ethyl]-2-oleyl-3-(2-hydroxyethyl)imidazolinium chloride (DOTIM), (1-methyl-4-(cis-9-dioleyl)methyl-pyridinium-chloride)) (SAINT), and C12-200, as described in Love et al., *Proc Natl Acad Sci USA*, 107(5): 1864-1869 (2010), which is incorporated herein by reference.

Cationic lipids include those of different chiral forms (e.g., R or S forms of any cationic lipid described herein) or any salt forms (e.g., a chloride, bromide, trifluoroacetate, or methanesulfonate salt of any cationic lipid described herein).

Additionally, a number of commercial preparations of cationic lipids may be included in the particle and/or formulation. Such commercial preparations include, but are not limited to: Lipofectamine™ (a combination of DOSPA and DOPE) and Lipofectin® (a combination of DOTMA and DOPE from Invitrogen Corp.; and Transfectam® (a composition including DOGS) and Transfast™ from Promega Corp.

Anionic Lipids

One or more anionic lipids can be included in the formulation and/or particles of the methods of the instant invention. Such anionic lipids include, but are not limited to:

phosphatidylglycerols (PGs), cardiolipins (CLs), diacylphosphatidylserines (PSs), diacylphosphatidic acids (PAs), phosphatidylinositols (PIs), N-acylphosphatidylethanolamines (NAPEs), N-succinylphosphatidylethanolamines, N-glutarylphosphatidylethanolamines, lysylphosphatidylglycerols, and palmitoyloleoylphosphatidylglycerol (POPG), as well as different chiral forms (e.g., R or S forms), salt forms (e.g., a chloride, bromide, trifluoroacetate, or methanesulfonate salts), and mixtures thereof Neutral Lipids One or more neutral lipids can be included in the formulation and/or particles of the methods of the instant invention. Such neutral lipids include, but are not limited to: ceramides, sphingomyelin (SM), diacylglycerols (DAGs), 1,2-distearoyl-sn-glycero-3-phosphocholine (DSPC, including chiral forms R-DSPC and S-DSPC), 1,2-dioleoyl-sn-glycero-3-phosphocholine (DOPC), 1,2-dipalmitoyl-sn-glycero-3-phosphocholine (DPPC), 1,2-dioleoyl-glycero-sn-3-phosphoethanolamine (DOPE), 1-palmitoyl-2-oleoyl-sn-glycero-3-phosphocholine (POPC), 1-palmitoyl-2-oleoyl-sn-glycero-3-phosphoethanolamine (POPE), 1,2-dipalmitoyl-sn-glycero-3-phosphoethanolamine (DPPE), 1,2-dimyristoyl-sn-glycero-3-phosphoethanolamine (DMPE), 1,2-distearoyl-sn-glycero-3-phosphoethanolamine (DSPE), 1,2-dielaidoyl-sn-glycero-3-phosphoethanolamine (DEPE), 1-stearoyl-2-oleoyl-sn-glycero-3-phosphoethanolamine (SOPE), 1,2-dilinoleoyl-sn-glycero-3-phosphocholine (DLPC), as well as different chiral forms (e.g., R or S forms), salt forms (e.g., a chloride, bromide, trifluoroacetate, or methanesulfonate salts), and mixtures thereof. Other diacyl-sn-glycero-3-phosphocholine and diacyl-glycero-sn-3-phosphoethanolamine lipids may also be used in the lipids particles of the invention.

In some embodiments, the neutral lipid component present in the formulation and/or particles comprises one or more phospholipids. In further embodiments, the neutral lipid component comprises a mixture of one or more phospholipids and cholesterol. In some embodiments, the selection of neutral lipids for use in the formulation and/or particles is guided by consideration of pharmacokinetic and/or pharmacodynamic properties, e.g., lipid particle size and stability in the bloodstream.

Sterol Derivatives

One or more sterol derivatives can be included in the formulation and/or particles of the methods of the instant invention. Without wishing to be limited by theory, sterol derivatives can be used to stabilize the formulation/particles and/or increase transfection. Exemplary sterol derivatives include cholesterol, derivatives of cholestanol (e.g., cholestanone, cholestenone, or coprostanol); 3β-[-(N—(N',N'-dimethylaminoethane)-carbamoyl]cholesterol (DC-cholesterol, e.g., a hydrochloride salt thereof); bis-guanidium-tren-cholesterol (BGTC); (2S,3 S)-2-(((3S,10R,13R,17R)-10,13-dimethyl-17-((R)-6-methylheptan-2-yl)-2,3,4,7,8,9,10,11, 12,13,14,15,16,17-tetradecahydro-1H-cyclopenta[a]phenanthren-3-yloxy)carbonylamino)ethyl 2,3,4,4-tetrahydroxybutanoate (DPC-1); (2S,3S)-((3S,10R,13R,17R)-10, 13-dimethyl-17-((R)-6-methylheptan-2-yl)-2,3,4,7,8,9,10, 11,12,13,14,15,16,17-tetradecahydro-1H-cyclopenta[a] phenanthren-3-yl) 2,3,4,4-tetrahydroxybutanoate (DPC-2); bis((3S,10R,13R,17R)-10,13-dimethyl-17-((R)-6-methyl-heptan-2-yl)-2,3,4,7,8,9,10,11,12,13,14,15,16,17-tetradeca-hydro-1H-cyclopenta[a]phenanthren-3-yl) 2,3,4-trihydroxy-pentanedioate (DPC-3); and 6-(((3S,10R,13R,17R)-10,13-dimethyl-17-((R)-6-methylheptan-2-yl)-2,3,4,7,8,9,10,11, 12,13,14,15,16,17-tetradecahydro-1H-cyclopenta[a] phenanthren-3-yloxy)oxidophosphoryloxy)-2,3,4,5-tetrahydroxyhexanoate (DPC-4).

PEG-Lipid Conjugates

One or more PEG-lipid conjugates can be included in formulation and/or particles of the methods of the instant invention. Without wishing to be limited by theory, PEG-lipid conjugates could act in reducing aggregation of lipid vectors. PEG-lipid conjugates are described in U.S. Pat. No. 5,885,613 and U.S. Patent Publication No. 2003/0077829, which are hereby incorporated by reference.

PEG-lipid conjugates that may be included in the formulation and/or particles include, but are not limited to: 1,2-dimyristoyl-sn-glycero-3-phosphoethanolamine-N-(carbonyl-methoxy-polyethylene glycol) (PEG-DMPE or DMPE-PEG) (e.g., 1,2-dimyristoyl-sn-glycero-3-phosphoethanolamine-N-(carbonyl-methoxy-polyethylene glycol-2000) (PEG-2000-DMPE or DMPE-PEG or DMPE-PEG2k)), 1,2-dipalmitoyl-sn-glycero-3-phosphoethanolamine-N-(carbonyl-methoxy-polyethylene glycol) (PEG-DPPE or DPPE-PEG), 1,2-distearoyl-sn-glycero-3-phosphoethanolamine-N-(carbonyl-methoxy-polyethylene glycol) (PEG-DSPE or DSPE-PEG), 1,2-dioleoyl-sn-glycero-3-phosphoethanolamine-N-(carbonyl-methoxy-polyethylene glycol) (PEG-DOPE or DOPE-PEG), 1,2-dimyristoyl-sn-glycerol-3-(methoxy-polyethylene glycol) (PEG-DMG or DMG-PEG) (e.g., 1,2-dimyristoyl-sn-glycerol-3-(methoxy-polyethylene glycol) (PEG-2000-DMG or DMG-PEG or DMG-PEG2k)), 1,2-dipalmitoyl-sn-glycerol-3-(methoxy-polyethylene glycol) (PEG-DPG or DPG-PEG), 1,2-distearoyl-sn-glycerol-3-(methoxy-polyethylene glycol) (PEG-DSG or DSG-PEG), 1,2-dioleoyl-sn-glycerol-3-(methoxy-polyethylene glycol) (PEG-DOG or DOG-PEG), 3-N-[(ω-methoxy-poly(ethylene glycol)2000)carbamoyl]-1,2-dimyristyloxy-propylamine (PEG-C-DMA), R-3-[(ω-methoxy poly (ethylene glycol)2000)carbamoyl)]-1,2-dimyristyloxl-propyl-3-amine (PEG-2000-C-DOMG), and PEG-ceramide conjugates (e.g., PEG-CerC14 or PEG-CerC20, which are described in U.S. Pat. No. 5,820,873, incorporated herein by reference). Additional PEG-lipid conjugates include PEG conjugated to any lipid described herein, such as phosphatidylethanolamine or ceramide (see, U.S. Pat. Nos. 5,820, 873; 5,534,499; and 5,885,613, which is incorporated herein by reference), and salt forms of any PEG-lipid conjugates described herein (e.g., sodium, ammonium, or trimethylammonium salts).

The PEG-lipid conjugate can include one or more various modifications, such as substitutions with any lipid molecule described herein or with PEG moieties of different molecular weights (e.g., from 300 to 5,000 daltons). Exemplary substitutions include use of one or more of C14:0 (as in Table 4), C16 (PEG-DPPE, PEG-DPG, etc.), C18:0 (PEG-DSPE, PEG-DSG, etc.), or C18:1 (PEG-DOPE, PEG-DOG, etc.) in combination with a polyethyleneglycol moiety (e.g., PEG2000, PEG3400, PEG5000, etc) to form a PEG-lipid conjugate (e.g., mPEG2000-DMG). Examples of PEG moieties with various molecular weights include PEG350, PEG550, PEG750, PEG1000, PEG2000, PEG3000, PEG3400, PEG4000, and PEG5000.

Exemplary Lipids

The formulation and/or particles can include one or a combination of any art-recognized lipids or other associated components, including, e.g., those described in U.S. Pat. Nos. 6,756,054; 5,976,567; 6,815,432; 6,858,225; 6,020, 526; 6,638,529; 6,670,393; 6,034,135; 5,958,901; 6,172, 049; 8,324,366; 8,158,601; 8,034,376; 8,329,070; 7,901, 708; 8,283,333; 8,236,943; 8,188,263; 8,101,741; 8,058, 069; 7,982,027; 7,803,397; 7,915,399; 7,807,815; 7,799, 565; 7,745,651; 6,841,537; 6,410,328; 7,811,602; 7,244,448; and 8,227,443, as well as application Nos. US 2012/0294905; US 2012/0244207; US 2012/0046478; US 2012/0183602; US 2012/0128760; US 2012/0101148; US 2009/0163705; US 2012/0016006; US 2003/0077829; WO 2010/088537; WO 2010/036962; US 2012/0095075; US 2012/0058144; US 2012/0027796; US 2011/0311583; US 2012/0027803; WO 2010/048536; WO 2011/038031; WO 2009/132131; WO 2009/100351; WO 2004/064737; WO 2004/030634; WO 2011/071860; WO 2013/013017; WO 2013/013013; WO 2010/057217; WO 2010/036962; WO 2011/153493; WO 2011/075656; WO 2010/144740; WO 2009/086558; WO 2010/054405; WO 2010/054401; WO 2010/054384; US 2011/0086826; US 2012/0225434; US 2011/0117125; WO 2009/086558; US 2011/0256175; WO 2010/042877; US 2010/0041152; US 2009/0285878; WO 2009/108235; WO 2009/108235; US 2011/0216622; US 2004/0142025; WO 2004/002453; US 2012/0202871; US 2011/0076335; WO 2011/000106; WO 2011/000107; US 2011/0195127; WO 2011/000108; US 2011/0178155; WO 2009/129319; US 2012/0328668; US 2009/0270481; US 2007/0135372; WO 2007/051303; US 2012/0183581; US 2010/0130588; US 2009/0291131; WO 2009/127060; WO 2009/082817; US 2012/0058188; US 2011/0091525; US 2006/0240093; US 2005/0175682; US 2005/0064595; WO 2005/007196; WO 2005/026372; WO 2005/007196; US 2011/0224418; US 2008/0249046; US 2006/0051405; US 2006/0025366; WO 2006/007712; WO 2006/002538; WO 2006/007712; US 2011/0262527; US 2011/0060032; US 2006/0083780; US 2006/0008910; WO 2005/120152; WO 2005/121348; WO 2005/120152; US 2005/0118253; US 2013/0022649; WO 2011/066651; US 2012/0172411; US 2011/0313017; US 2011/0201667; WO 2011/011447; US 2011/0189300; US 2006/0134189; WO 2006/053430; US 2011/0177131; US 2007/0135370; WO 2007/048046; US 2011/0071208; US 2009/0149403; US 2008/0171716; WO 2008/019486; US 2007/0218122; WO 2007/056861; US 2007/0054873; US 2007/0042031; WO 2007/012191; WO 2002/088370; US 2003/0108886; WO 2002/088370; WO 2002/087541; WO 2011/038160; WO 2010/083615; WO 2011/141705; WO 2011/141704; WO 2012/000104; WO 2011/141703; WO 2010/105372; and WO 2006/074546.

Other Components

The formulation and/or particles can include any other component to aid in stabilizing the lipid vector, reducing aggregation of lipid vectors, and/or delivering a therapeutic agent (e.g., an RNAi agent). Exemplary components include polyamide-lipid conjugates (ATTA-lipids) based on co-amino (oligoethyleneglycol) alkanoic acid monomers, such as those described in U.S. Pat. Nos. 6,320,017 and 6,586,559, which is incorporated herein by reference; gangliosides (e.g., asialoganglioside GM1 or GM2; disialoganglioside GD1a, GD1a-NAcGal, GD1-b, GD2, or GD3; globoside, monosialoganglioside GM1, GM2, or GM3, tetrasialoganglioside GQ1b, and trisialoganglioside GT1a or GT1b); antioxidants (e.g., α-tocopherol or β-hydroxytoluidine); one or more surfactants (e.g., sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cetyl ether, as well as polyoxyethylene castor oil or hydrogenated castor oil derivatives and polyglycerine fatty acid esters, such as Pluronic®, Poloxamer®, Span®, Tween®, Polysorbate®, Tyloxapol®, Emulphor®, or Cremophor® (e.g., Cremophor® EL having a major component of glycerol-polyethyleneglycol ricinoleate with fatty acid esters of polyethylene glycol); one or more amphiphilic agents (e.g., vegetable oils, such as soybean oil, safflower oil, olive oil, sesame oil, borage oil, castor oil, and cottonseed oil; mineral oils and marine oils, hydrogenated and/or fractionated triglycerides from such sources; medium chain triglycerides (MCT-oils, e.g., Miglyol®), and various synthetic or semi-synthetic mono-, di- or triglycerides, such as the defined nonpolar lipids disclosed in WO 92/05571, as well as acetylated monoglycerides, or alkyl esters of fatty acids, such isopropyl myristate, ethyl oleate (see EP 0 353 267) or fatty acid alcohols, such as oleyl alcohol, cetyl alcohol); and one or more salts, such as any salt described herein. Typically, the concentration of the lipid component selected to reduce aggregation is about 1 mol % to 15 mol %.

Lipid Vectors

The formulation and/or particles of the methods of the invention can include one or more compounds selected from Table 1, and/or any lipid-based composition capable of transporting a therapeutic agent (e.g., an anionic agent, such as an RNAi agent). Exemplary lipid-based compositions include one or more lipid molecules (e.g., compounds of Table 1, cationic lipids, anionic lipids, or neutral lipids) and/or one or more components (e.g., sterol derivatives and/or PEG-lipid conjugates).

Lipid vectors can be formed using any biocompatible lipid or combination of lipids capable for forming a lipid vector (e.g., liposomes, lipoplexes, and micelles). Encapsulation of a therapeutic agent into a lipid vector can protect the agent from damage or degradation or facilitate its entry into a cell. Lipid vectors, as a result of charge interactions (e.g., a cationic lipid vector and anionic cell membrane), interact and fuse with the cell membrane, thus releasing the agent into the cytoplasm. A liposome is a bilayered vesicle comprising one or more of compounds of the invention, lipid molecules, and/or components. A lipid nanoparticle is a liposome ranging in size from about 1 nm to about 1,000 nm. A lipoplex is a liposome formed with cationic lipid molecules to impart an overall positive charge to the liposome. A micelle is vesicle with a single layer of lipid molecules.

Liposomes

In certain embodiments, the lipid vector is a liposome. Typically, the lipids used are capable of forming a bilayer and are cationic. Classes of suitable lipid molecules include phospholipids (e.g., phosphotidylcholine), fatty acids, glycolipids, ceramides, glycerides, and cholesterols, or any combination thereof. Alternatively or in addition, the lipid vector can include neutral lipids (e.g., dioleoylphosphatidyl ethanolamine (DOPE)). Other lipids that can form lipid vectors are known in the art and described herein.

As used herein, a "lipid molecule" is a molecule with a hydrophobic head moiety and a hydrophilic tail moiety and may be capable of forming liposomes, including a compound of Table 1 or any cationic, neutral, or anionic lipid described herein. The lipid molecule can optionally be modified to include hydrophilic polymer groups. Examples of such lipid molecules include 1,2-distearoyl-sn-glycero-3-phosphoethanolamine-N-[methoxy(polyethylene glycol)-2000] (PEG2000-DSPE), e.g., an ammonium salt thereof) and 1,2-distearoyl-sn-glycero-3-phosphoethanolamine-N-[carboxy(polyethylene glycol)-2000] (PEG2000-DSPE carboxy).

Examples of lipid molecules include natural lipids, such as cardiolipin (CL), phosphatidic acid (PA), phosphatidylcholine (PC), lysophosphatidylcholine (LPC), phosphatidylethanolamine (PE), phosphatidylglycerol (PG), phosphatidylinositol (PI), and phosphatidylserine (PS); lipid mixtures, such as lechitin; sphingolipids, such as sphingosine, ceramide, sphingomyelin, cerebrosides, sulfatides, gangliosides, and phytosphingosine; cationic lipids, such as 1,2-dioleoyl-3-trimethylammonium-propane (DOTAP), 1,2-dioleoyl-3-dimethylammonium-propane (DODAP), dimethyldioctadecyl ammonium bromide (DDAB), 3-1β-[N—(N',N'-dimethylaminoethane)carbamoly]cholesterol (DC-Chol), N-[1-(2,3,-ditetradecyloxy)propyl]-N,N-dimethyl-N-hydroxyethylammonium bromide (DMRIE), N-[1-(2,3,-dioleyloxy)propyl]-N,N-dimethyl-N-hydroxy ethylammonium bromide (DOME), and 1,2-di-O-octadecenyl-3-trimethylammonium propane (DOTMA); phosphatidylcholines, such as 1,2-dilauroyl-sn-glycero-3-ethylphosphocholine, 1,2-dilauroyl-sn-glycero-3-phosphocholine (D-LPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-phosphocholine (DOPC), and 1-palmitoyl-2-oleoyl-sn-glycerol-3-phosphocholine (POPC); phosphoethanolamines, such as 1,2-dibutyryl-sn-glycero-3-phosphoethanolamine, 1,2-distearoyl-sn-glycero-3-phosphoethanolamine (DSPE), 1,2-dimyristoyl-sn-glycero-3-phosphoethanolamine (DMPE), 1,2-dipalmitoyl-sn-glycero-3-phosphoethanolamine (DPPE), 1,2-dioleoyl-sn-glycero-3-phosphoethanolamine (DOPE), 1-palmitoyl-2-oleoyl-sn-glycero-3-phosphoethanolamine (POPE), and 1,2-dioleoyl-sn-glycero-3-phosphoethanolamine-N-(glutaryl); phosphatidic acids, such as dicetyl phosphate (DCP), 1,2-dimyristoyl-sn-glycero-3-phosphate, 1,2-dipalmitoyl-sn-glycero-3-phosphate, and 1,2-dioleoyl-sn-glycero-3-phosphate; phosphatidylglycerols, such as dipalmitoyl phosphatidylglycerol (DPPG), dioleoyl phosphatidylglycerol (DOPG), 1,2-dimyristoyl-sn-glycero-3-phospho-(1'-rac-glycerol), and 1,2-dioleoyl-sn-glycero-3-phospho-(1'-rac-glycerol); phosphatidylserines, such as 1,2-dimyristoyl-sn-glycero-3-phospho-L-serine, 1,2-dipalmitoyl-sn-glycero-3-phospho-L-serine, and 1,2-dioleoyl-sn-glycero-3-phospho-L-serine; cardiolipins, such as 1',3'-bis[1,2-dimyristoyl-sn-glycero-3-phospho]-sn-glycerol; and PEG-lipid conjugates, such as 1,2-dipalmitoyl-sn-glycero-3-phosphoethanolamine-N-[methoxy(polyethylene glycol)-750], 1,2-dipalmitoyl-sn-glycero-3-phosphoethanolamine-N-[methoxy(polyethylene glycol)-2000],1,2-dipalmitoyl-sn-glycero-3-phosphoethanolamine-N-[methoxy(polyethylene glycol)-5000], 1,2-distearoyl-sn-glycero-3-phosphoethanolamine-N-[methoxy(polyethylene glycol)-2000], and 1,2-distearoyl-sn-glycero-3-phosphoethanolamine-N-[carboxy(polyethylene glycol)-2000].

Compounds such as those of Table 1 can be combined with any useful lipid composition, including commercially available lipid compositions. Examples of such compositions include Lipofectamine™ (a combination of DOSPA and DOPE) and Lipofectin® (a combination of DOTMA and DOPE) from Invitrogen Corp.; Transfectam® (a composition including DOGS) and Transfase™ from Promega Corp.; NeuroPORTER™ and Escort™ from Sigma-Aldrich Co.; FuGENE® 6 from Roche; and LipoTAXI® from Stratgene. Known lipid compositions include the Trojan Horse Lipsome technology, as described in Boado, Pharm. Res. 24:1772-1787 (2007).

The liposomes can also include other components that aid in the formation or stability of liposomes. Examples of components include cholesterol, antioxidants (e.g., α-tocopherol or β-hydroxytoluidine), surfactants, and salts.

The liposome can be of any useful combination comprising lipid molecules, including, e.g., one or more compounds of Table 1 and other lipid components that aid in the formation or stability of liposomes. A person of skill in that art will know how to optimize the combination that favor encapsulation of a particular agent, stability of the liposome, scaled-up reaction conditions, or any other pertinent factors. Exemplary combinations are described in Boado, Pharm. Res. 24:1772-1787 (2007).

Producing liposomes typically occur through a general two-step process. In the first step, the lipids and lipid components are mixed in a volatile organic solvent or mixtures of solvents to ensure a homogenous mixture of lipids. Examples of solvents include chloroform, methanol, cyclohexane, and t-butanol. The solvent is then removed to form a dry lipid mixture in a film, powder, or pellet. The solvent can also be removed by using any known analytical techniques, such as by using nitrogen, rotary evaporation, spray drying, lyophilization, and vacuum-drying.

In the second step, the dry lipid mixture is hydrated with an aqueous solution to form liposomes. The agent can be added to the aqueous solution, which results in the formation of liposomes with encapsulated agent. Alternatively, the liposomes are first formed with a first aqueous solution and then exposed to another aqueous solution containing the agent. Encapsulation of the agent can be promoted by any known technique, such as by repeat freeze-thaw cycles, sonication, or mixing. A further example of this approach is described in Boado, Pharm. Res. 24:1772-1787 (2007). Alternatively, the agent is coupled to a hydrophobic moiety (e.g., cholesterol) to produce a lipophilic derivative and the lipophilic derivative is used with other lipid molecules to form liposomes.

During the second step, the dry lipid mixture may or may not contain the polypeptide-lipid conjugate. The process can optionally include various additional steps, including heating the aqueous solution past the phase transition temperature of the lipid molecules before adding it to the dry lipid mixture, where particular ranges of temperatures include from about 40° C. to about 70° C.; incubating the combination of the dry lipid mixture and the aqueous solution, where particular time ranges include from about 30 minutes to about 2 hours; mixing of the dry lipid mixture and the aqueous solution during incubation, such as by vortex mixing, shaking, stirring, or agitation; addition of nonelectrolytes to the aqueous solution to ensure physiological osmolality, such as a solution of 0.9% saline, 5% dextrose, and 10% sucrose; disruption of large multilamellar vesicles, such as by extrusion or sonication; and additional incubation of the pre-formed liposomes with polypeptide-lipid conjugate, where the dry lipid mixture did not contain the lipid molecules. One of skill in the art will be able to identify the particular temperature and incubation times during this hydration step to ensure incorporation of the derivatized lipid molecule into the liposomes or to obtain stable liposomes.

Lipid compounds such as those of Table 1 can be added at any point in the process of forming liposomes. In one example, the compound is added to the lipids and lipid components during the formation of the dry lipid mixture. In another example, the compound is added to liposomes that are pre-formed with a dry lipid mixture containing the lipids and lipid components. In yet another example, micelles are formed with the compound, liposomes are formed with a dry lipid mixture containing lipids and lipid components, and then the micelles and liposomes are incubated together. The aqueous solution can include additional components to stabilize the agent or the liposome, such as buffers, salts, chelating agents, saline, dextrose, sucrose, etc.

In one example of this procedure, a dry film composed of the lipid mixture is hydrated with an aqueous solution containing an agent. This mixture is first heated to 50° C. for 30 minutes and then cooled to room temperature. Next, the mixture is transferred onto a dry film containing the polypeptide-lipid conjugate. The mixture is then incubated at 37° C. for two hours to incorporate the polypeptide-lipid conjugate into the liposomes containing the agent. See, e.g., Zhang et al., *J. Control. Release* 112:229-239 (2006).

Lipid Particles Having a Vesicle Structure

In certain embodiments, the lipid particle comprises a cationic lipid (e.g., DODMA, DOTMA, and/or an amino-amine lipid, amino-amide lipid, or other such lipid, e.g., of Table 1) and an anionic agent (e.g., an RNAi agent), as well as a neutral or zwitterionic lipid, a PEG-lipid conjugate, and, optionally, cholesterol.

Lipid Particles Having One or More RNA-Binding Agents and One or More Transfection Lipids Lipid particles also include those having one or more RNA-binding agents and one or more transfection lipids. In one embodiment, the one or more RNA-binding agents form an internal aggregate, and the one or more transfection lipids form an external, aggregate surface. In particular embodiments, the external, aggregate surface is not a membrane, a lipid bilayer, and/or a multilamellar layer. In certain embodiments, the one or more RNA-binding agents (e.g., lipids) represent about 10-90% of the total lipids. In other embodiments, the one or more RNA-binding agents (e.g., lipids) represent about 50% of the total lipid. In other embodiments, the one or more RNA-binding agents (e.g., lipids) represent about 30% of the total lipid. In certain embodiments, the complex/aggregate of a nucleic acid agent with one or more RNA-binding agents of the lipid particle comprises a cationic lipid (e.g., DODMA, DOTMA, and/or an amino-amine lipid or amino-amide lipid, e.g., of Table 1) and an RNAi agent; and the one or more transfection lipids of the lipid particle comprise a neutral or zwitterionic lipid, a PEG-lipid conjugate, and, optionally, cholesterol. In other embodiments, the one or more transfection lipids of the particle comprise a cationic lipid (e.g., DODMA, DOTMA, an amino-amine lipid, and/or an amino-amide lipid), a neutral lipid, a PEG-lipid conjugate, and, optionally, cholesterol.

Scalable Lipid Particle Manufacturing Process

In certain embodiments, the invention provides processes for particle production which improve upon processes previously practiced, with such improved processes, for example, allowing for production of larger amounts of lipid particles with little or even no significant loss of particle efficacy, as compared to other such processes for making lipid particles and/or formulations. Without wishing to be bound by theory, the processes of the invention are designed to produce a more homogeneous population of particle sizes and structures than those obtained using alternative processes for particle/formation preparation. Such attributes of the instant invention are believed to result from the order of addition of components during performance of the processes disclosed herein—specifically, where anionic agent-containing complexes are suspended in an aqueous solution and additional lipids are suspended in a solvent such as ethanol, addition of the ethanol-containing lipid solution to the aqueous solution containing the anionic agent complexes results in less disruption/dissociation of anionic agent complexes than when the aqueous solution containing anionic agent complexes is added to the ethanol-containing lipid solution. When the latter order of addition is performed (aqueous into ethanol), the initial anionic agent complexes added to the ethanol-containing lipid solution are exposed to an elevated concentration of ethanol, which then declines over time following further addition of the aqueous solution to the ethanol solution, ultimately to achieve the final ethanol concentration of the mixed solution. Exposure of these initial anionic agent complexes to a transiently high concentration of ethanol is thought to be disruptive to such complexes, resulting in greater heterogeneity of particle structures and sizes within an ultimate particle population that also possesses reduced activity and/or potency. In contrast, certain aspects of the instant invention relate to the surprising identification of improved particle population structural and size homogeneity, efficacy and/or potency when the order of addition is such that the ethanol solution containing additional lipids is added to the anionic agent complexes suspended in aqueous solution, which causes the anionic agent complexes to be exposed to an initially low and then gradually increasing concentration of ethanol (to achieve the same final concentration as when the order of addition is reversed), in turn resulting in reduced particle disruption and/or dissociation and improved particle population homogeneity, efficacy and/or potency.

While differences between methods, e.g., that involve addition of aqueous complexes to solvent (e.g., ethanol)-suspended lipids and the improved methods of the instant invention can be modest and/or difficult to detect at small production scales (e.g., preparation of 1 mg of anionic agent in particles in one mL volume of water), such inventive differences become much more pronounced and apparent once production scale is increased. Exemplary particle production scales for the processes of the invention include not only small-scale production (e.g., 1 mg of anionic agent in particles), but also 10 mg or more of anionic agent in particles, 50 mg or more of anionic agent in particles, 100 mg or more of anionic agent in particles, 250 mg or more of anionic agent in particles, 500 mg or more of anionic agent in particles, 1 g or more of anionic agent in particles, 2 g or more of anionic agent in particles, 3 g or more of anionic agent in particles, 4 g or more of anionic agent in particles, 5 g or more of anionic agent in particles, 7.5 g or more of anionic agent in particles, 10 g or more of anionic agent in particles, 20 g or more of anionic agent in particles, 40 g or more of anionic agent in particles, 50 g or more of anionic agent in particles, 100 g or more of anionic agent in particles, 200 g or more or anionic agent in particles, 300 g or more of anionic agent in particles, 400 g or more of anionic agent in particles, 500 g or more of anionic agent in particles, 1 kg or more of anionic agent in particles, 2 kg or more of anionic agent in particles, 3 kg or more of anionic agent in particles, 4 kg or more of anionic agent in particles, 5 kg or more of anionic agent in particles, or 10 kg or more of anionic agent in particles.

In certain embodiments, particles of the improved processes of the instant invention possess at least 10% greater total efficacy and/or potency (per particle quantity and/or volume, etc.) than a corresponding population of particles produced by methods involving addition of the aqueous solution to the solvent (e.g., ethanol) solution. Optionally, particles of the improved processes of the instant invention possess at least 20% greater, at least 30% greater, at least 40% greater, at least 50% greater, at least 60% greater, at least 70% greater, at least 80% greater, at least 90% greater, at least 100% greater, at least 200% greater, at least 500% greater, or at least 1000% greater total efficacy and/or potency (per particle quantity and/or volume, etc.) than a corresponding population of particles produced by methods involving addition of the aqueous solution to the solvent (e.g., ethanol) solution. In related embodiments, particles of the improved processes of the instant invention reduce anionic agent (e.g., RNAi agent) target gene expression to at least 10% lower absolute levels than a corresponding population of particles produced by methods involving addition of the aqueous solution to the solvent (e.g., ethanol) solution. Optionally, particles of the improved processes of the instant invention reduce anionic agent (e.g., RNAi agent) target gene expression to at least 20% lower absolute levels, at least 30% lower absolute levels, at least 40% lower absolute levels, at least 50% lower absolute levels, at least 60% lower absolute levels, at least 70% lower absolute levels, at least 80% lower absolute levels, at least 90% lower absolute levels, at least 95% lower absolute levels, or 100% lower absolute levels than a corresponding population of particles produced by methods involving addition of the aqueous solution to the solvent (e.g., ethanol) solution. Such differences or improvements are commonly best observed at high levels of particle production, such as at levels of about 10 mg or higher, 20 mg or higher, 50 mg or higher, 100 mg or higher, 250 mg or higher, 500 mg or higher, 1 g or higher, 2 g or higher, 3 g or higher, 4 g or higher, 5 g or higher, 7.5 g or higher, 10 g or higher, 20 g or higher, 40 g or higher, 50 g or higher, 100 g or higher, 200 g or more or anionic agent, 300 g or higher, 400 g or higher, 500 g or higher, 1 kg or higher, 2 kg or higher, 3 kg or higher, 4 kg or higher, 5 kg or higher, or 10 kg or higher.

The lipid particles of the processes of the invention typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In addition, nucleic acids, when present in the lipid particles of the processes of the present invention, are resistant in aqueous solution to degradation with a nuclease. Nucleic acid-lipid particles and certain methods of preparation are disclosed in, e.g., U.S. Patent Publication Nos. 20040142025 and 20070042031, the disclosures of which are herein incorporated by reference in their entirety for all purposes.

RNAi Agents

RNA interference (RNAi) is a mechanism that inhibits gene expression by causing the degradation of specific RNA molecules or hindering the transcription of specific genes. In nature, RNAi targets are often RNA molecules from viruses and transposons (a form of innate immune response), although it also plays a role in regulating development and genome maintenance. Key to the mechanism of RNAi are small interfering RNA strands (siRNA), which have sufficiently complementary nucleotide sequences to a targeted messenger RNA (mRNA) molecule. The siRNA directs proteins within the RNAi pathway to the targeted mRNA and degrades them, breaking them down into smaller portions that can no longer be translated into protein.

The RNAi pathway is initiated by the enzyme Dicer, which cleaves long, double-stranded RNA (dsRNA) molecules into siRNA molecules, typically about 21 to about 23 nucleotides in length and containing about 19 base pair duplexes. One of the two strands of each fragment, known as the guide strand, is then incorporated into the RNA-induced silencing complex (RISC) and pairs with complementary sequences. RISC mediates cleavage of single-stranded RNA having sequence complementary to the antisense strand of the siRNA duplex. Cleavage of the target RNA takes place in the middle of the region complementary to the antisense strand of the siRNA duplex. The outcome of this recognition event is post-transcriptional gene silencing. This occurs when the guide strand specifically pairs with a mRNA molecule and induces the degradation by Argonaute, the catalytic component of the RISC complex.

The particles of the methods of the invention can be used to deliver one or more anionic agents, such as RNAi agents, to a cell in vitro or in vivo (e.g., in a subject). RNAi agents can include different types of double-stranded molecules that include either RNA:RNA or RNA:DNA strands. These agents can be introduced to cells in a variety of structures, including a duplex (e.g., with or without overhangs on the 3'-terminus), a hairpin loop, or an expression vector that express one or more polynucleotides capable of forming a double-stranded polynucleotide alone or in combination with another polynucleotide. Exemplary RNAi agents include siRNA, shRNA, DsiRNA, and miRNA agents, which are described herein. Generally, these agents are about 10 to about 40 nucleotides in length, and preferred lengths are described below for particular RNAi agents.

Functional gene silencing by an RNAi agent does not necessarily include complete inhibition of the targeted gene product. In some cases, marginal decreases in gene product expression caused by an RNAi agent may translate to significant functional or phenotypic changes in the host cell, tissue, organ, or animal. Therefore, gene silencing is understood to be a functional equivalent and the degree of gene product degradation to achieve silencing may differ between gene targets or host cell type.

siRNA

Small interfering RNA (siRNA) are generally double-stranded RNA molecules of 16 to 30 nucleotides in length (e.g., 18 to 25 nucleotides, e.g., 21 nucleotides) with one or two nucleotide overhangs on the 3'-terminii or without any overhangs. A skilled practitioner may vary this sequence length (e.g., to increase or decrease the overall level of gene silencing). In certain embodiments, the overhangs are UU or dTdT at the 3'-terminus. Generally, siRNA molecules are completely complementary to one strand of a target DNA molecule, since even single base pair mismatches have been shown to reduce silencing. In other embodiments, siRNAs may have a modified backbone composition, such as, for example, 2'-deoxy- or 2'-O-methyl modifications, or any modifications described herein.

siRNA refers to a nucleic acid molecule capable of inhibiting or down-regulating gene expression in a sequence-specific manner; see, for example, Zamore et al., Cell 101:25 33 (2000); Bass, Nature 411:428-429 (2001); Elbashir et al., Nature 411:494-498 (2001); and PCT Publication Nos. WO 00/44895, WO 01/36646, WO 99/32619, WO 00/01846, WO 01/29058, WO 99/07409, and WO 00/44914. Methods of preparing a siRNA molecule for use in gene silencing are described in U.S. Pat. No. 7,078,196, which is hereby incorporated by reference.

shRNA

Short hairpin RNA (shRNA) are single-stranded RNA molecules in which a hairpin loop structure is present, allowing complementary nucleotides within the same strand to form intermolecular bonds. shRNA can exhibit reduced sensitivity to nuclease degradation as compared to siRNA. In certain embodiments, an shRNA have a stem length from 19 to 29 nucleotides in length (e.g., 19 to 21 nucleotides or 25 to 29 nucleotides). In some embodiments, loop size is between 4 to 23 nucleotides in length. shRNA can generally contain one or more mismatches, e.g., G-U mismatches between the two strands of the shRNA stem, without decreasing potency.

DsiRNA

Dicer-substrate RNA (DsiRNA) are double-stranded RNA agents of 25 to 35 nucleotides. Agents of such length are believed to be processed by the Dicer enzyme of the RNA interference (RNAi) pathway, whereas agents shorter than 25 nucleotides generally mimic Dicer products and escape Dicer processing. In some embodiments, DsiRNA has a single-stranded nucleotide overhang at the 3'-terminal of the antisense or sense strand of 1 to 4 nucleotides (e.g., 1 or 2 nucleotides).

Certain modified structures of DsiRNA agents were previously described, as such as in U.S. Patent Publication No. 2007/0265220, which is incorporated herein by reference. Additional DsiRNA structures and specific compositions suitable for use in the formulations of the instant invention are described in U.S. patent application Ser. No. 12/586,283; U.S. Patent Publication Nos. 2005/0244858, 2005/0277610, 2007/0265220, 2011/0021604, 2010/0173974, 2010/0184841, 2010/0249214, 2010/0331389, 2011/0003881, 2011/0059187, 2011/0111056; and PCT Publication Nos. WO 2010/080129, WO 2010/093788, WO 2010/115202, WO 2010/115206, WO 2010/141718, WO 2010/141724, WO 2010/141933, WO 2011/072292, WO 2011/075188, which are hereby incorporated by reference. Generally, DsiRNA constructs are synthesized using solid phase oligonucleotide synthesis methods as described for 19-23mer siRNAs (see U.S. Pat. Nos. 5,804,683; 5,831,071; 5,998,203; 6,117,657; 6,353,098; 6,362,323; 6,437,117; 6,469,158; 6,111,086; 6,008,400; and 6,111,086).

miRNA

MicroRNA (miRNA) are single-stranded RNA molecules of 17 to 25 nucleotides (e.g., 21 to 23 nucleotides) in length. A skilled practitioner may vary this sequence length to increase or decrease the overall level of gene silencing. These agents silence a target gene by binding complementary sequences on target messenger RNA. As used herein, the term "miRNA precursor" is used to encompass, without limitation, primary RNA transcripts, pri-miRNAs and pre-miRNAs. A "miRNA agent" of the invention can include pri-miRNA, pre-miRNA, and/or miRNA (or mature miRNA). In certain embodiments, an siRNA (e.g., a DsiRNA) of the invention may present a guide strand that incorporates a miRNA sequence, or is sufficiently homologous to the miRNA sequence to function as said miRNA (rendering such siRNA a "miRNA mimetic").

Antisense Compounds

Exemplary antisense compounds comprise a consecutive nucleoside length range, wherein the upper end of the range is 50 nucleosides and wherein the lower end of the range is 8 nucleosides. In certain embodiments, the upper end of the range is 35 nucleosides and the lower end of the range is 14 nucleosides. In further embodiments, the upper end of the range is 24 nucleosides and the lower end of the range is 17 nucleosides. In still further embodiments, the antisense compound is 20 consecutive nucleosides. Those skilled in the art will readily recognize that the upper end of the range, as disclosed herein comprises 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive nucleosides and the lower end of the range comprises 8, 9, 10, 11, 12, 13, 14, 15, 16, 17, 18, 19 or 20 consecutive nucleosides.

Exemplary antisense compounds comprise a stretch of at least 8, optionally at least 12, optionally at least 15 consecutive nucleosides that is sufficiently complementary to a target sequence to interfere with transcription, translation, promote degradation (optionally nuclease-mediated degradation) and/or otherwise disrupt the function (e.g., interfere with the function of an otherwise functional target sequence, e.g., disruption of a promoter, enhancer or other functional nucleic acid target sequence via an antisense compound-mediated mechanism) of the target sequence.

Modifications can be made to antisense compounds and may include conjugate groups attached to one of the termini, selected nucleobase positions, sugar positions or to one of the internucleoside linkages. Possible modifications include, but are not limited to, 2'-fluoro (2'-F), 2'-OMethyl (2'-OMe), 2'-O-(2-methoxyethyl) (2'-MOE) high affinity sugar modifications, inverted abasic caps, deoxynucleobases, and bicyclic nucleobase analogs, such as locked nucleic acids (LNA) and ethylene-bridged nucleic acids (ENA).

Method of Making RNAi Agents

RNAi agents include at least one antisense nucleotide sequence that is directed to a target nucleic acid (e.g., a target gene). Antisense nucleotides are single strands of DNA or RNA that are complementary to a chosen target sequence. In the case of antisense RNA, they prevent translation of complementary RNA strands by binding to it. Antisense DNA can be used to target a specific, complementary (coding or non-coding) RNA. In a particular embodiment, antisense nucleotides contain from about 10 to about 40 nucleotides, more preferably about 15 to about 30 nucleotides. The antisense nucleotide can have up to 80%, 85%, 90%, 95%, 99%, or even 100% complementary to the desired target gene.

Methods of producing antisense and sense nucleotides, as well as corresponding duplexes or hairpin loops, are known in the art and can be readily adapted to produce an antisense oligonucleotide that targets any target nucleic acid sequence. Antisense nucleotide sequences can be selected to optimize target specificity, such as by analyzing the target sequence and determining secondary structure, Tm, binding energy, and relative stability; and/or to reduce the formation of secondary structures, such as dimers, hairpins, or other secondary structures that would reduce or prohibit specific binding to the target mRNA in a host cell. In some embodiments, highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., *Nucleic Acids Res.* 25(17):3389-3402, 1997). Non-limiting methods for preparing RNAi agents are described in U.S. Pat. Nos. 5,804,683; 5,831,071; 5,998,203; 6,117,657; 6,353,098; 6,362,323; 6,437,117; 6,469,158; 6,111,086; 6,008,400; and 6,111,086, which are incorporated herein by reference.

The RNAi agents can have any useful form, such as single-stranded, double-stranded, linear, circular (e.g., a plasmid), nicked circular, coiled, supercoiled, concatemerized, or charged. Additionally, nucleotides may contain 5' and 3' sense and antisense strand terminal modifications and can have blunt or overhanging terminal nucleotides (e.g., UU or TT at the 3'-terminus), or combinations thereof.

Modified nucleic acids, including modified DNA or RNA molecules, may be used in the in place of naturally occurring nucleic acids in the polynucleotides (e.g., RNAi agents) described herein. Modified nucleic acids can improve the half-life, stability, specificity, delivery, solubility, and nuclease resistance of the polynucleotides described herein. For example, siRNA agents can be partially or completed composed of nucleotide analogs that confer the beneficial qualities described above. As described in Elmen et al. (*Nucleic Acids Res.* 33:439-447 (2005)), synthetic, RNA-like nucleotide analogs (e.g., locked nucleic acids (LNA)) can be used to construct siRNA molecules that exhibit silencing activity against a target gene product.

The phosphorothioate (PS) backbone modification, where a non-bridging oxygen in the phosphodiester bond is replaced by sulfur, is one of the earliest and most common means deployed to stabilize nucleic acid drugs against nuclease degradation. In general, it appears that PS modifications can be made extensively to both siRNA strands without much impact on activity (Kurreck, Eur. *J. Biochem.* 270:1628-44 (2003)). In particular embodiments, the PS modification is usually restricted to one or two bases at the 3' and 5' ends. The boranophosphate linker can be used to enhance siRNA activity while having low toxicity (Hall et al., *Nucleic Acids Res.* 32:5991-6000 (2004)). Other exemplary modifications to the oligonucleotide backbone include methylphosphonates, phosphorodithioates, phosphotriesters, aminoalkylphosphotriesters, alkyl phosphonates (e.g., 3'-alkylene phosphonate), chiral phosphonates, phosphinates, phosphoramidates (e.g., 3'-amino phosphoramidate), aminoalkylphosphoramidates, thionophosphoramidates, thionoalkylphosphonates, thionoalkylphosphotriesters, and a protein nucleotide (PNA) backbone having repeating N-(2-aminoethyl)-glycine units linked by peptide bonds, where representative PNA compounds include, but are not limited to, those disclosed in U.S. Pat. Nos. 5,539, 082, 5,714,331, and 5,719,262, and Nielsen et al., *Science* 254:1497-1500 (1991).

Other modifications to the backbone include those replacing the phosphorous atom with short chain alkyl or cycloalkyl internucleoside linkages, mixed heteroatom and alkyl or cycloalkyl internucleoside linkages, or one or more short chain heteroatomic or heterocyclic internucleoside linkages (e.g., morpholino linkages; siloxane backbones; sulfide, sulfoxide and sulfone backbones; formacetyl and thioformacetyl backbones; methylene formacetyl and thioformacetyl backbones; alkene containing backbones; sulphamate backbones; methyleneimino and methylenehydrazino backbones; sulfonate and sulfonamide backbones; amide backbones; and others having mixed N, O, S and $CH_2$ component parts).

Certain modified nucleobases are particularly useful for increasing the binding affinity of the oligomeric compounds of the invention, such as 5-substituted pyrimidines, 6-azapyrimidines and N-2, N-6 and O-6 substituted purines (e.g., 2-aminopropyladenine, 5-propynyluracil, 5-propynylcytosine, and 5-methylcytosine). Exemplary modified nucleobases include 5-methylcytosine (5-me-C or m5c); 5-hydroxymethyl cytosine, xanthine, and hypoxanthine; 2-aminoadenine, 6-methyl, and other alkyl derivatives of adenine and guanine; 2-propyl and other alkyl derivatives of adenine and guanine; 2-thiouracil; 2-thiothymine; 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxy, and other 8-substituted adenines and guanines; 5-halo, particularly 5-bromo, 5-trifluoromethyl and other 5-substituted uracils and cytosines; 7-methylguanine; 7-methyladenine; 8-azaguanine; 8-azaadenine; 7-deazaguanine; 7-deazaadenine; 3-deazaguanine; and 3-deazaadenine. These modified nucleobases may be combined, in particular embodiments, with other modifications, such as any sugar modification described herein.

Modified oligonucleotides may also contain one or more substituted sugar moieties, where modifications can be made at any reactive site of the ribose ring (e.g., the 2'-OH of the ribose ring), or one or more universal bases. Exemplary modifications include 2'-halo, such as F, Br, or Cl; 2'-O-alkyl, 2'-S-alkyl, or 2'-N-alkyl, such as 2'-OMe; alkyl, such as 2'-O-methoxyethyl (2'-O-MOE), 2'-O[$(CH_2)_nO]_mCH_3$, 2'-O$(CH_2)_n$OCH$_3$, 2'-O$(CH_2)_2$ON(CH$_3$)$_2$O(CH$_2$)$_n$NH$_2$, O(CH$_2$)$_n$CH$_3$, 2'-O(CH$_2$)$_n$ONH$_2$, and 2'-O(CH$_2$)$_n$ON[(CH$_2$)$_n$CH$_3$)]$_2$, where n and m are from 1 to about 10; 2'-O-alkenyl, 2'-S-alkenyl, or 2'-N-alkenyl; 2'-O-alkynyl, 2'-S-alkynyl, or 2'-N-alkynyl, wherein the alkyl, alkenyl and alkynyl may be substituted or unsubstituted $C_{1-10}$ alkyl or $C_{2-10}$ alkenyl and alkynyl, as well as a bridging modification between the 2' and 4' positions of ribose to form a locked nucleic acid (LNA). Exemplary universal bases include a heterocyclic moiety located at the 1' position of a nucleotide sugar moiety in a modified nucleotide, or the equivalent position in a nucleotide sugar moiety substitution, such as 1-O-D-ribofuranosyl-5-nitroindole and 1-β-D-ribofuranosyl-3-nitropyrrole.

In certain embodiments, nucleic acids possessing described forms of modification and/or patterns of modification can be employed. Additional detail regarding exemplary modifications and modification patterns of nucleic acids can be found, e.g., in at least the following references: US 2010/0240734; WO 2010/080129; WO 2010/033225; US 2011/0021604; WO 2011/075188; WO 2011/072292; WO 2010/141724; WO 2010/141726; WO 2010/141933; WO 2010/115202; WO 2008/136902; WO 2011/109294; WO 2011/075188; PCT/US11/42810; PCT/US11/42820; U.S. Ser. No. 61/435,304; U.S. Ser. No. 61/478,093; U.S. Ser. No. 61/497,387; U.S. Ser. No. 61/529,422; U.S. Pat. No. 7,893,245; WO 2007/051303; and US 2010/0184209. Each of the preceding documents is hereby incorporated by reference in its entirety.

RNAi Gene Targets

In certain embodiments, the present invention features the silencing of a target gene in a diseased tissue or organ by treatment with a particle or formulation, in combination with an RNAi agent. The therapeutic potential of the present invention is realized when the mRNA molecules of a specific and targeted gene known or thought to be involved in the establishment or maintenance of the disease state (e.g., a cancer) are degraded by the RNAi agent.

Examples of RNAi targets for use with the present invention include developmental proteins, such as adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors; oncogene-encoded proteins (e.g., ABL1 (UniProt Entry No. P00519, NCBI Gene ID: 25), AR (UniProt Entry No. P10275, NCBI Gene ID: 3647), β-Catenin (CTNNB1, UniProt Entry No. P35222, NCBI Gene ID: 1499), BCL1 (UniProt Entry No. P24385, NCBI Gene ID: 595), BCL2 (UniProt Entry No. P10415, NCBI Gene ID: 596), BCL6 (UniProt Entry No. P41182), CBFA2 (UniProt Entry No. Q01196, NCBI Gene ID: 861), CBL (UniProt Entry No. P22681, NCBI Gene ID: 687), CSF1R (UniProt Entry No. P07333, NCBI Gene ID: 1436), ERBA1 (UniProt Entry No. P10827, NCBI Gene ID: 7067), ERBA2 (UniProt Entry No. P10828, NCBI Gene ID: 7068), ERBB (UniProt Entry No. P00533, NCBI Gene ID: 1956), ERBB2 (UniProt Entry No. P04626, NCBI Gene ID: 2064), ERBB3 (UniProt Entry No. P21860, NCBI Gene ID: 190151), ERBB4 (UniProt Entry No. Q15303, NCBI Gene ID: 600543), ETS1 (UniProt Entry No. P14921, NCBI Gene ID: 2113), ETS2 (UniProt Entry No. P15036, NCBI Gene ID: 2114), ETV6 (UniProt Entry No. 41212, NCBI Gene ID: 2120), FGR (UniProt Entry No. P09769, NCBI Gene ID: 2268), FOS (UniProt Entry No. P0110, NCBI Gene ID: 2353), FYN (UniProt Entry No. P06241, NCBI Gene ID: 2534), HCR (UniProt Entry No. Q8TD31, NCBI Gene ID: 54535), HRAS (UniProt Entry No. P01112, NCBI Gene ID: 3265), JUN (UniProt Entry No. P05412, NCBI Gene ID: 3725), KRAS (UniProt Entry No. P01116, NCBI Gene ID: 3845), LCK (UniProt Entry No. P06239 NCBI Gene ID: 3932), LYN (UniProt Entry No. P07948, NCBI Gene ID: 4067), MDM2 (UniProt Entry No. Q00987, NCBI Gene ID: 4193), MLL1 (UniProt Entry No. Q03164, NCBI Gene ID: 4297), MLL2 (UniProt Entry No. 014686, NCBI Gene ID: 8085), MLL3 (UniProt Entry No. Q8NEZ4, NCBI Gene ID: 58508), MYB (UniProt Entry No. P10242, NCBI Gene ID: 4602), MYC (UniProt Entry No. P01106, NCBI Gene ID: 4609), MYCL1 (UniProt Entry No. P12524, NCBI Gene ID: 4610), MYCN (UniProt Entry No. P04198, NCBI Gene ID: 4613), NRAS (UniProt Entry No. P01111, NCBI Gene ID: 4893), PIM1 (UniProt Entry No. P11309, NCBI Gene ID: 5292), PML (UniProt Entry No. P29890, NCBI Gene ID: 5371), RET (UniProt Entry No. P07949, NCBI Gene ID: 5979), SRC (UniProt Entry No. P12931, NCBI Gene ID: 6714), TAL1 (UniProt Entry No. P17542, NCBI Gene ID: 6886), TAL2 (UniProt Entry No. Q16559, NCBI Gene ID: 6887), TCL3 (UniProt Entry No. P31314, NCBI Gene ID: 3195), TCL5 (UniProt Entry No. P17542, NCBI Gene ID: 6886), and YES (UniProt Entry No. P07947, NCBI Gene ID: 7525)); tumor suppressor proteins (e.g., BRCA1 (UniProt Entry No. P38398, NCBI Gene ID: 672), BRCA2 (UniProt Entry No. P51587, NCBI Gene ID: 675), MADH4 (UniProt Entry No. Q13485, NCBI Gene ID: 4089), MCC (UniProt Entry No. P23508, NCBI Gene ID: 4163), NF1 (UniProt Entry No. P21359, NCBI Gene ID: 4763), NF2 (UniProt Entry No. P35240, NCBI Gene ID: 4771), RB1 (UniProt Entry No. P06400, NCBI Gene ID: 5925), TP53 (UniProt Entry No. P04637, NCBI Gene ID: 7157), PLK1 (UniProt Entry No. P53350, NCBI Gene ID: 9606), KIF1-binding protein (UniProt Entry No. Q96EK5, NCBI Gene ID: 9606), and WT1 (UniProt Entry No. P19544, NCBI Gene ID: 4790)); lipoproteins (e.g., apolipoprotein B (ApoB100, UniProt Entry No. P04114, NCBI Gene ID: 338)); enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hernicellulases, integrases, inulinases, invertases, isomerases, kinases (e.g., PLK1 (UniProt Entry No. P53350, NCBI Gene ID: 9606)), lactases, ligases (e.g., ring finger- and WD repeat-containing protein 2 (RFWD2), also known as COP1), lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, ribulose-1,5-bisphosphate carboxylase oxygenases (RuBisCos), topoisomerases, transferases, such as hypoxanthine guanine phosphoribosyltransferase 1 (HPRT1), and xylanases).

The liver is one of the most important target tissues for nucleic acid therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by polynucleotide-based liver therapies. A number of diseases or conditions which affect or are affected by the liver are potentially treated through knockdown (inhibition) of gene expression in the liver. Exemplary liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury. Exemplary molecular targets for liver therapeutics (e.g., including therapeutics targeted to HCC in particular)—and optionally for therapeutics addressing other targets, diseases and/or disorders, including other cancers—include CSN5 (UniProt Entry No. Q92905, NCBI Gene ID: 10987), CDK6 (UniProt Entry No. Q00534, NCBI Gene ID: 1021), ITGB1 (UniProt Entry No. P05556, NCBI Gene ID: 3688), MYC (UniProt Entry No. P01106, NCBI Gene ID: 4609), TGF431 (UniProt Entry No. P01137, NCBI Gene ID: 7040), Cyclin D1 (UniProt Entry No. Q9H014, NCBI Gene ID: 595), hepcidin (UniProt Entry No. P81172, NCBI Gene ID: 57817), PCSK9 (UniProt Entry No. Q8NBP7, NCBI Gene ID: 255738), and transthyretin (TTR, UniProt Entry No. P02766, NCBI Gene ID: 7276), among others.

Particles and/or formulations of the methods of the invention optionally can be targeted to normal tissues (e.g., normal liver tissue), as well as to various models (e.g., orthotopic liver models, subcutaneous liver models, etc.).

One exemplary target for the particles of the processes of the invention is Apolipoprotein B (ApoB), which is found in various classes of lipoproteins: chylomicrons, very low density lipoproteins (VLDL), intermittent density lipoproteins (IDL), and low density lipoproteins (LDL). ApoB functions as a recognition signal for the cellular binding and internalization of LDL particles by the ApoB/E receptor. An accumulation or overabundance of apolipoprotein B-containing lipoproteins can lead to lipid-related disorders such as atherosclerosis. Formulated therapies that reduce ApoB can be useful for treating lipid-related disorders. One nucleic acid based therapy, in the form of antisense therapy, has been shown to reduce ApoB levels in mouse in vivo, and treatments subsequently reduced serum cholesterol and triglyceride levels (U.S. Publication No. 2003/0215943). These results demonstrated a moderate downregulation of ApoB and its use as a target in treating lipid-related disorders.

Another exemplary target for the particles of the processes of the invention is Protein C, which may be targeted, e.g., for the treatment of hemophilia.

Lipid-DsiRNA nanoparticles typically form spontaneously upon mixing lipids with DsiRNAs to form a complex. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. In further preparation of a particle for use, ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formulations of particles are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total DsiRNA concentration in the formulation, as well as the entrapped fraction, is estimated using a dye exclusion assay. A sample of the formulated DsiRNA can be incubated with an RNA-binding dye, such as Ribogreen (Molecular Probes) in the presence or absence of a formulation disrupting surfactant, e.g., 0.5% Triton-X100. The total DsiRNA in the formulation can be determined by the signal from the sample containing the surfactant, relative to a standard curve. The entrapped fraction is determined by subtracting the "free" DsiRNA content (as measured by the signal in the absence of surfactant) from the total DsiRNA content. Percent entrapped DsiRNA is typically >85%. For certain formulations, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Delivery of a Therapeutic Agent

The particles and/or formulations of the processes of the invention may be used to deliver a therapeutic agent (e.g., anionic agents, such as nucleic acids or RNAi agents) to cells. The agent delivered by the particles and/or formulations can be used for gene-silencing (e.g., in vitro or in vivo in a subject) or to treat or prophylactically treat a disease (e.g., cancer) in a subject.

Delivery of a therapeutic agent may be assessed by using any useful method. For example, delivery with a particle and/or formulations produced by the processes of the invention may be assessed by 1) knockdown of a target gene or 2) toxicity or tolerability, as compared to a control at an equivalent dose. These assessments can be determined with any useful combination of lipids in the particle and/or formulation, such as any cationic lipid described herein (e.g., DOTAP, DODMA, DLinDMA, and/or DLin-KC2-DMA), optionally in combination, e.g., with a compound of Table 1. In particular embodiments, an improvement of delivery of a therapeutic agent (e.g., anionic agent, such as an RNAi agent) is observed when using a process of the invention, where the improvement is more than 25% (e.g., more than a 2-fold, 5-fold, 10-fold, 100-fold, or 1000-fold improvement in delivery), as compared to a control.

Delivery of RNAi Agents

RNAi silencing can be used in a wide variety of cells, where HeLa S3, COST, 293, NIH/3T3, A549, HT-29, CHO-KI and MCF-7 cell lines are among those susceptible to some level of siRNA silencing. Furthermore, suppression in mammalian cells can occur at the RNA level with specificity for the targeted genes, where a strong correlation between RNA and protein suppression has been observed. Accordingly, the particles produced by the processes of the invention, and formulations thereof, may be used to deliver an RNAi agent to one or more cells (e.g., in vitro or in vivo). Exemplary RNAi agents include siRNA, shRNA, dsRNA, miRNA, and DsiRNA agents, as described herein.

In Vitro Target Knockdown

Delivery of a RNAi agent can be assessed by any useful method. For example, formulations including a therapeutic agent can be transfected in vitro in cell culture models (e.g., HeLa cells), where end point measurements include, but are not limited to, one or more of the following: (i) mRNA quantification using qPCR; (ii) protein quantification using Western blot; (iii) labeled cell internalization of the anionic agent and/or a cationic lipid of a particle made by the processes of the invention. Uptake or delivery may be assessed for both the extent and duration of the above-mentioned end points. Prior to delivery, the formulation may be diluted in cell culture media at room temperature for about 30 minutes, and the final concentration can be varied from 0 to 50 nM of the anionic agent or of one or more lipids or other particle and/or formulation components in dose-response experiments. For time-course experiments, an optimum concentration from the dose-experiment may be studied for various incubation times, e.g., 30 minutes to 7 days.

The functionality of anionic agent and lipid formulations may also be tested by differentially labeling the lipid compound and the therapeutic agent with fluorescent tags and performing fluorescent colocalization studies. The ability of the compounds of the invention to deliver anionic agents and/or an attached fluorescent label may be assessed both by measuring the total fluorescence inside the cell and by measuring fluorescence that is not stably associated with endosomal or lysosomal compartments (to function, therapeutic agents that trigger RNAi are required not only to reach inside the cell, but also to reach the cytoplasm of the cell). Performance of fluorescence localization and cellular trafficking studies has been described in the art (Lu, et al., *Mol. Pharm.* 6(3):763, 2009; McNaughton et al., *Proc. Natl. Acad. Sci. U.S.A.* 106(15):6111, 2009).

Delivery to Particular Target Cell Types and Target Tissues

The particles made by the processes of the invention can be used to deliver therapeutic agents (e.g., anionic agents) to various organs and tissues to treat various diseases. Exemplary targeted tissues or organs include, but are not limited to, liver, pancreas, lung, prostate, kidney, bone marrow, spleen, thymus, lymph node, brain, spinal cord, heart, skeletal muscle, skin, oral mucosa, esophagus, stomach, ileum, small intestine, colon, bladder, cervix, ovary, testis, mammary gland, adrenal gland, adipose tissue (white and/or brown), blood (e.g., hematopoietic cells, such as human hematopoietic progenitor cells, human hematopoietic stem cells, CD34+ cells, CD4+ cells), lymphocytes and other blood lineage cells.

Cancer Therapy

The particles produced by the processes of the invention can be used to deliver one or more therapeutic agents (e.g., RNAi agents) to a subject having cancer or at risk of developing a cancer (e.g., an increased risk of at least 10%, 20%, 30%, 40%, 50%, 60%, 70%, 80%, 90%, or 100%). Exemplary cancers include liver cancer (e.g., hepatocellular carcinoma, hepatoblastoma, cholangiocarcinoma, angiosarcoma, or hemangiosarcoma) or neuroblastoma. Exemplary neoplastic diseases and associated complications include, but are not limited to, carcinomas (e.g., lung, breast, pancreatic, colon, hepatocellular, renal, female genital tract, squamous cell, carcinoma in situ), lymphoma (e.g., histiocytic lymphoma, non-Hodgkin's lymphoma), MEN2 syndromes, neurofibromatosis (including Schwann cell neoplasia), myelodysplastic syndrome, leukemia, tumor angiogenesis, cancers of the thyroid, liver, bone, skin, brain, central nervous system, pancreas, lung (e.g., small cell lung cancer, non small cell lung cancer (NSCLC)), breast, colon, bladder, prostate, gastrointestinal tract, endometrium, fallopian tube, testes and ovary, gastrointestinal stromal tumors (GISTs), prostate tumors, mast cell tumors (including canine mast cell tumors), acute myeloid myelofibrosis, leukemia, acute lymphocytic leukemia, chronic myeloid leukemia, chronic lymphocytic leukemia, multiple myeloma, melanoma, mastocytosis, gliomas, glioblastoma, astrocytoma, neuroblastoma, sarcomas (e.g., sarcomas of neuroectodermal origin or leiomyosarcoma), metastasis of tumors to other tissues, and chemotherapy-induced hypoxia.

Administration and Dosage

The present invention also relates to processes for production of pharmaceutical compositions that contain a compound or a therapeutically effective amount of a composition, such as a formulation including a therapeutic agent (e.g., an RNAi agent). The composition can be formulated for use in a variety of drug delivery systems. One or more physiologically acceptable excipients or carriers can also be included in the composition for proper formulation. Suitable formulations for use in the present invention are found in Remington's Pharmaceutical Sciences, Mack Publishing Company, Philadelphia, Pa., 17th ed., 1985. For a brief review of methods for drug delivery, see, e.g., Langer, Science 249:1527-1533, 1990.

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a patient with a clinically determined predisposition or increased susceptibility to development of a tumor or cancer. Compositions of the invention can be administered to the patient (e.g., a human) in an amount sufficient to delay, reduce, or preferably prevent the onset of clinical disease or tumorigenesis. In therapeutic applications, compositions are administered to a patient (e.g., a human) already suffering from a cancer in an amount sufficient to cure or at least partially arrest the symptoms of the condition and its complications. An amount adequate to accomplish this purpose is defined as a "therapeutically effective dose," an amount of a compound sufficient to substantially improve some symptom associated with a disease or a medical condition. For example, in the treatment of cancer, an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the patient, but generally range from about 0.5 mg to about 3000 mg of the agent or agents per dose per patient. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. The agents of the invention are administered to a subject (e.g., a mammal, such as a human) in an effective amount, which is an amount that produces a desirable result in a treated subject (e.g., the slowing or remission of a cancer or neurodegenerative disorder). Such therapeutically effective amounts can be determined empirically by those of skill in the art.

The patient may also receive an agent in the range of about 0.1 to 3,000 mg per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) mg dose per week. A patient may also receive an agent of the composition in the range of 0.1 to 3,000 mg per dose once every two or three weeks.

The amount (dose) of formulation and agent (e.g., DsiRNA) that is to be administered can be determined empirically. In certain embodiments, effective knockdown of gene expression is observed using 0.0001-10 mg/kg animal weight of nucleic acid agent and 0.001-200 mg/kg animal weight delivery formulation. An exemplary amount in mice is 0.1-5 mg/kg nucleic acid agent and 0.7-100 mg/kg delivery formulation. Optionally, about 1-50 mg/kg delivery formulation is administered. The amount of agent (e.g., DsiRNA) is easily increased because it is typically not toxic in larger doses.

In certain embodiments, doses can be administered daily over a period of days, weeks, or longer (e.g., between one and 28 days or more), or only once, or at other intervals, depending upon, e.g., acute versus chronic indications, etc.

Single or multiple administrations of the compositions of the invention comprising an effective amount can be carried out with dose levels and pattern being selected by the treating physician. The dose and administration schedule can be determined and adjusted based on the severity of the disease or condition in the patient, which may be monitored throughout the course of treatment according to the methods commonly practiced by clinicians or those described herein.

The compounds and formulations of the present invention may be used in combination with either conventional methods of treatment or therapy or may be used separately from conventional methods of treatment or therapy. When the compounds and formulations of this invention are administered in combination therapies with other agents, they may be administered sequentially or concurrently to an individual. Alternatively, pharmaceutical compositions according to the present invention include a combination of a compound or formulation of the present invention in association with a pharmaceutically acceptable excipient, as described herein, and another therapeutic or prophylactic agent known in the art.

The formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

EXAMPLES

Example 1

Process for Production of Anionic Agent-Containing Particles (Process 2141)

HPRT1 & MYC DsiRNAs

Particles were prepared as described below with a cationic lipid (DODMA), a neutral lipid (DSPC), a PEG-lipid conjugate (PEG-DMPE and PEG-DMG), and cholesterol with an RNAi agent (DsiRNA for HPRT1 or MYC), having one of the following structures:

```
HPRT1:
                                        (SEQ ID NO: 1)
5'-GCCAGACUUUGUUGGAUUUGAAAtt (SEQ ID NO: 2)
3'-UUCGGUCUGAAACAACCUAAACUUUAA

MYC-622:
                                        (SEQ ID NO: 3)
5'-AGGAACUAUGACCUCGACUACGAct-3'

(SEQ ID NO: 4)
3'-UGUCCUUGAUACUGGAGCUGAUGCUGA-5'

MYC-1711:
                                        (SEQ ID NO: 5)
5'-AGCUUUUUUGCCCUGCGUGACCAga-3'

(SEQ ID NO: 6)
3'-CCUCGAAAAAACGGGACGCACUGGUCU-5'
``` where uppercase letters signify to RNA nucleotide, underlined uppercase letters signify a 2'-O-methyl-RNA nucleotide, and lowercase letters signify a DNA nucleotide. Note that while SEQ ID NOs: 2, 4, 6, and 8 are presented above in complementary 3'-5' orieintation, in the Sequence Listing provided with this application, they are presented in 5'-3' orientation as required and as shown in listing of Sequences below in Table 11).

Preparation of DsiRNA Strands: Oligonucleotide Synthesis and Purification

Individual RNA strands were synthesized and HPLC purified according to standard methods (Integrated DNA Technologies, Coralville, Iowa). For example, RNA oligonucleotides were synthesized using solid phase phosphoramidite chemistry, deprotected, and desalted on NAP-5 columns (Amersham Pharmacia Biotech, Piscataway, N.J.) using standard techniques (Damha and Olgivie, Methods Mol. Biol. 20:81, 1993; Wincott et al., Nucleic Acids Res. 23: 2677, 1995). The oligomers were purified using ion-exchange high performance liquid chromatography (IE-HPLC) on an Amersham Source 15Q column (1.0 cm×25 cm; Amersham Pharmacia Biotech, Piscataway, N.J.) using a 15 min. step-linear gradient. The gradient was from 90:10 Buffers A:B to 52:48 Buffers A:B, where Buffer A is 100 mM Tris pH 8.5 and Buffer B is 100 mM Tris pH 8.5, 1 M NaCl. Samples were monitored at 260 nm, and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 µm inner diameter and contained ssDNA 100R Gel (Beckman-Coulter). Typically, about 0.6 nmole of oligonucleotide was injected into a capillary, run in an electric field of 444 V/cm and detected by UV absorbance at 260 nm. Denaturing Tris-Borate-7 M-urea running buffer was purchased from Beckman-Coulter. Oligoribonucleotides were obtained that are at least 90% pure as assessed by CE for use in experiments described below. Compound identity was verified by matrix-assisted laser desorption ionization time-of-flight (MALDI-TOF) mass spectroscopy on a Voyager DETM Biospectometry Workstation (Applied Biosystems, Foster City, Calif.) following the manufacturer's recommended protocol. Relative molecular masses of all oligomers were obtained, often within 0.2% of expected molecular mass.

Preparation of DsiRNA Duplexes

Single-stranded RNA (ssRNA) oligomers were resuspended, e.g., at 100 µM concentration in duplex buffer consisting of 100 mM potassium acetate, 30 mM HEPES, pH 7.5. Complementary sense and antisense strands were mixed in equal molar amounts to yield a final solution of, e.g., 50 µM duplex. Samples were heated to 100° C. for 5 minutes in RNA buffer (IDT) and allowed to cool to room temperature before use. Double-stranded RNA (dsRNA) oligomers were stored at −20° C. Single-stranded RNA oligomers were stored lyophilized or in nuclease-free water at −80° C.

Preparation of Particles

DsiRNA-lipid complexes were initially produced by combining (a) 24 mg/mL of anti-HPRT1 DsiRNA dissolved in 12.5 mL of water with (b) 37.5 mL of a lipid suspension comprising the components of Table 5 in 60 mM HCl (pH=2.3).

TABLE 5

Composition of Aqueous Lipids Used to Form DsiRNA-Lipid Complexes

|  | DODMA | DMPE-PEG2000 |
| --- | --- | --- |
| MW (Da) | 620.90 | 2693.30 |
| mol % | 90.04 | 9.96 |
| wt % | 67.58 | 32.42 |
| Mol (mmol) | 2.14 | 0.24 |
| Wt (mg) | 1330.71 | 638.31 |

The above components of Table 5 were extruded through 100 nm membranes for 10-12 cycles, and were then assessed for particle size and polydispersity index (PDI), which were 80.76 nm and 0.058, respectively. After combining DsiRNA and the initial lipid suspension, 100 mL of water was added, resulting in a final pH of 2.8 for the 150 mL volume of DsiRNA-lipid complexes obtained (refer to FIG. 1). DsiRNA-lipid complexes were then deposited into a mixing vessel, and 100 mL of an additional solution of lipids (possessing total lipid content of 37 mg/mL) dissolved in 100% ethanol was then added to the aqueous DsiRNA-lipid complex suspension. The composition of this additional solution of lipids is shown in Table 6.

TABLE 6

Composition of EtOH-Dissolved Lipids Added to DsiRNA-Lipid Complexes

|  | DSPC | CHOL | L-30 of Table 1 | DSPE-PEG2k |
| --- | --- | --- | --- | --- |
| MW (Da) | 790.16 | 386.4 | 613.05 | 2805.50 |
| mol % | 19.38 | 46.44 | 30.32 | 3.87 |
| wt % | 24.43 | 28.63 | 29.65 | 17.30 |
| Mol (mmol) | 1.143 | 2.739 | 1.788 | 0.228 |
| Wt (mg) | 903.15 | 1058.35 | 1096.13 | 639.65 |

Upon completing the mixing of additional lipids with the DsiRNA-lipid complexes, 500 mL of water were added to the particles, which produced a further reduction in the ethanol concentration of the mixed suspension, to 14.3% ethanol (optionally, variable volumes of ethanol may be added at this stage, e.g., 180 mL of water to reduce the ethanol concentration to 25%, 1.75 L of water to reduce the ethanol concentration to 8%, 3.75 L of water to reduce the ethanol concentration to 4%, etc.). This mixed suspension was then subjected to tangential flow filtration (TFF), resulting in a concentrated volume of about 150 mL. This suspension was then diafiltrated with 600 mL PBS, and was then rinsed twice with 50 mL PBS, resulting in a total volume of 220 mL.

Particle size (93.11 nm), polydispersity index (PDI=0.106) and concentration were then measured. For concentration, DsiRNA-lipid complexes were measured as being 1.3 mg/mL, encapsulation efficiency was observed to be 95.44% and total volume was 220 mLs, meaning that an addition of 52.96 mL PBS was required to bring the final concentration of the sample to 1 mg/mL. Notably, the final ethanol concentration of this particle-containing sample was below 0.15%. The process demonstrated in Example 1 is referred to generally herein as "process 2141" and is distinguished in Example 2 from "process 2072" described below.

Example 2

Process 2072 Compared with Process 2141 of Example 1

A process similar to the above process but distinguished from the above process only in that the concentration of additional lipids in ethanol was reduced relative to the above-described process (termed the "2072 process") was initially examined for properties of particles so formed. Regarding the processes of this Example, the proportions and total amounts of lipids used during formulation of particles in the "2072 process", for which results are described in this Example, and the "2141 process", which is set forth in above Example 1, were the same. The only difference between the "2141 process" and the "2072 process" can be found in the concentration of lipids that were used in the additional lipids in ethanol solution component of the processes, which was elevated in the "2141 process" in a manner as described in the below Examples, relative to the "2072 process".

Particles produced by both the "2072 process" involving addition of DsiRNA-lipid complexes into additional lipids in ethanol, as well as by the "2141 process" involving addition of additional lipids in ethanol into DsiRNA-lipid complexes were assessed for their physical properties and compared. The top two panels of FIG. 2 demonstrate that reversal of the order of addition of DsiRNA-lipid complexes and additional lipids in ethanol (process 2141 as compared with process 2072) created a dramatic and surprising difference in both the average particle size and size distribution of particles obtained by the reverse process. Specifically, when a 100 mg batch (DsiRNA content=100 mg) of particles was made by a "2072 process" in which DsiRNA-lipid complexes were added to additional lipids in ethanol, the resultant particles possessed an average size of 152.6 nm, while the heterogeneity of this particle population was high, as reflected in an observed PDI value of 0.265 for this preparation. In contrast, when a larger, 300 mg batch (DsiRNA content=100 mg) of particles was made by a process that involved adding the additional lipids in ethanol into the DsiRNA-lipid complex suspension, (the "2141 process") average particle size was reduced to 98.85 and size distribution of the particle population was also found to be dramatically more homogeneous (PDI=0.127).

This result demonstrated that the implemented alteration of order-of-addition impacted particle size and homogeneity in a dramatic, advantageous and surprising manner. As demonstrated in the below Examples, lower average particle size and reduced heterogeneity of such particle populations were associated with both improved efficacy (of knockdown and phenotypic impact) and improved tolerability/reduced toxicity of particle populations when they were administered to a subject.

Example 3

Elevating Concentrations of Additional Lipids in Ethanol Improved Particle Properties The above-described process schematically exemplified in FIG. 1, which is also referred to herein as "2141", was not only distinguished from other tested processes in the order of addition of DsiRNA-lipid complexes and additional lipids in ethanol, but also was distinguished from other processes by the concentration of lipids and sterols that were solubilized in the additional lipids in ethanol solution. Specifically, in the "2072 process", cholesterol was added to solvent at a concentration of approximately 10-11 mg/ml in ethanol, which approached the solubility limit of cholesterol in ethanol. Further lipids were then added to this cholesterol-in-ethanol mixture to create the "additional lipids in ethanol" component, and there was a limit to the amount of total lipid that could be present in the "additional lipids in ethanol" solution of approximately 20 mg/ml total lipid. In contrast, in the "2141 process" of the invention, L-30 of Table 1, DSPC and DSPE-PEG2k were combined in 100 ml of ethanol in the amounts shown in Table 6 above. This ethanol solution was then added to cholesterol as a powder, at a cholesterol concentration of approximately 11 mg/ml, but with the distinction that the total lipid content of this "additional lipids in ethanol" solution achieved a total lipid content of 37 mg/ml in the absence of aggregation or other deleterious effect. (Indeed, additional batches of this "additional lipids in ethanol" solution were also successfully prepared that possessed approximately 21 mg/ml cholesterol (a level that dramatically exceeded the solubility of cholesterol alone in ethanol) and 74 mg/ml total lipid in ethanol.)

The impact of driving total lipid content of the "additional lipids in ethanol" solution of the current processes above the approximately 20 mg/ml or lower levels used for "2072" and similar processes, to approximately 34 mg/ml in the case of the "2141 process"/particles, was both unexpected and dramatic: particles prepared by the "2141 process" possessed improved size and polydispersity as compared to particles prepared by the "2072 process"; "2141" particles also demonstrated better target-specific knockdown than particles prepared by the "2072 process", exhibited improved efficacy at reducing tumor volume in a Hep3B mouse model of liver cancer, and were much better tolerated in mice than corresponding particles prepared by the "2072 process".

Figure 2:
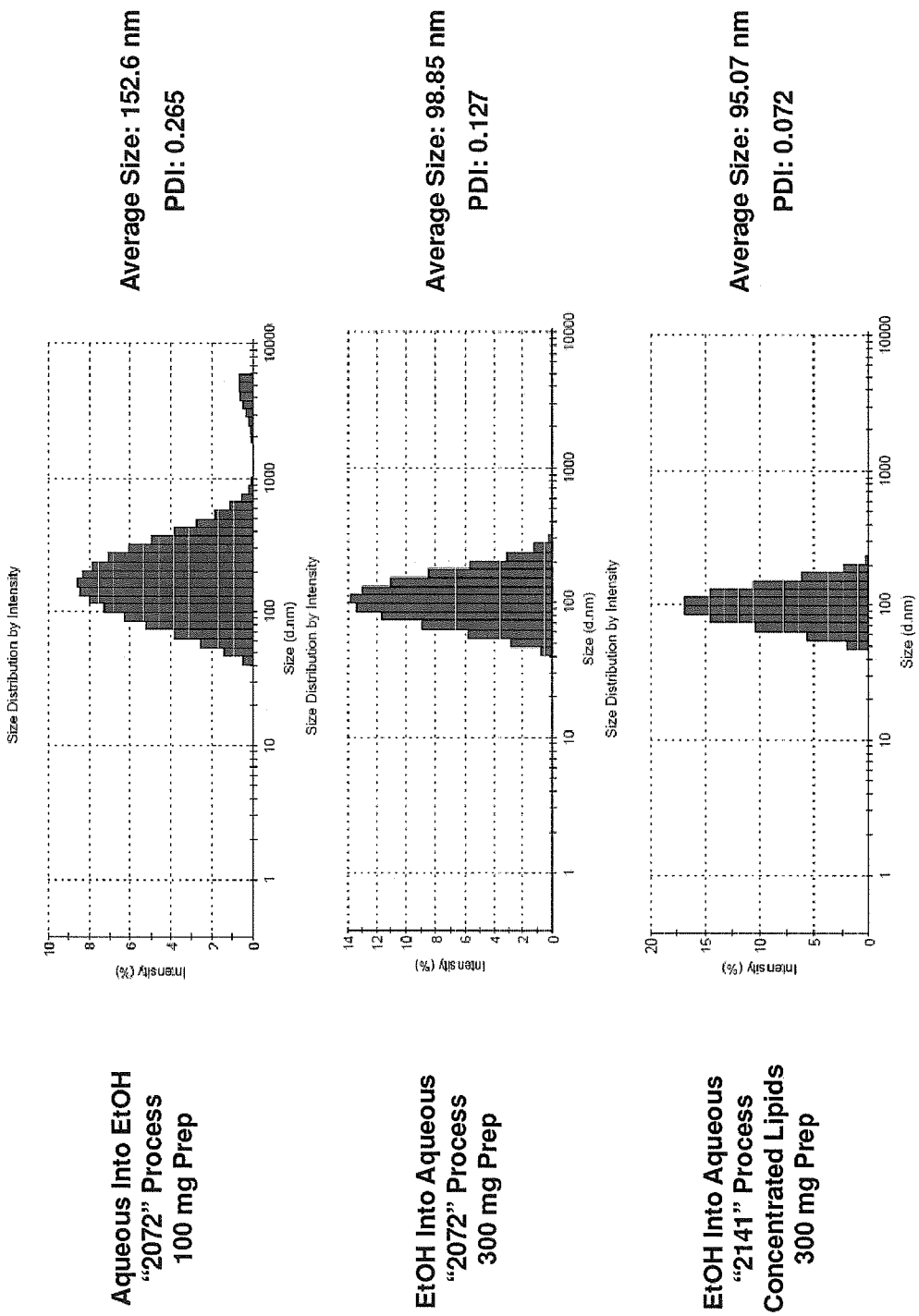
FIG. 2 shows sizing results for particles formulated by three distinct methods: particles formulated by a process that involved adding aqueous lipid-DsiRNA complexes into additional lipids dissolved in ethanol ("2072 process", variation 1, top panel); particles formulated by a process that involved adding additional lipids dissolved in ethanol into aqueous lipid-DsiRNA complexes ("2072 process", variation 2, middle panel); and particles formulated by a process that incorporated identical total amounts and proportions of components as "2072" but that featured a step that allowed for concentration of lipids within ethanol, specifically by dissolving a number of lipids in ethanol prior to dissolution of cholesterol in the lipid-containing ethanol solution—such process allowed for remarkable concentration of such lipids within such ethanol solution ("2141 process", lower panel).

The bottom two panels of FIG. 2 show the improved size and polydispersity values that were observed for a population of particles prepared using the "2141 process" (which featured an elevated concentration of additional lipids in ethanol during the formulation process) as compared to such particles prepared using the "2072 process" (which featured total concentrations of additional lipids in ethanol at or below 20 mg/ml during the formulation process). Specifically, the "2141 process" yielded particles that possessed an average size of 95.07 nm with observed PDI of 0.072, as compared to corresponding particles produced by the "2072 process", which exhibited an average size of 98.85 nm and observed PDI of 0.127. Thus, particles produced by the "2141 process" were observed to be slightly more compact and significantly more homogeneous than corresponding particles produced by the "2072 process", by this gross assessment of the physical properties of both particle populations.

Figure 3:
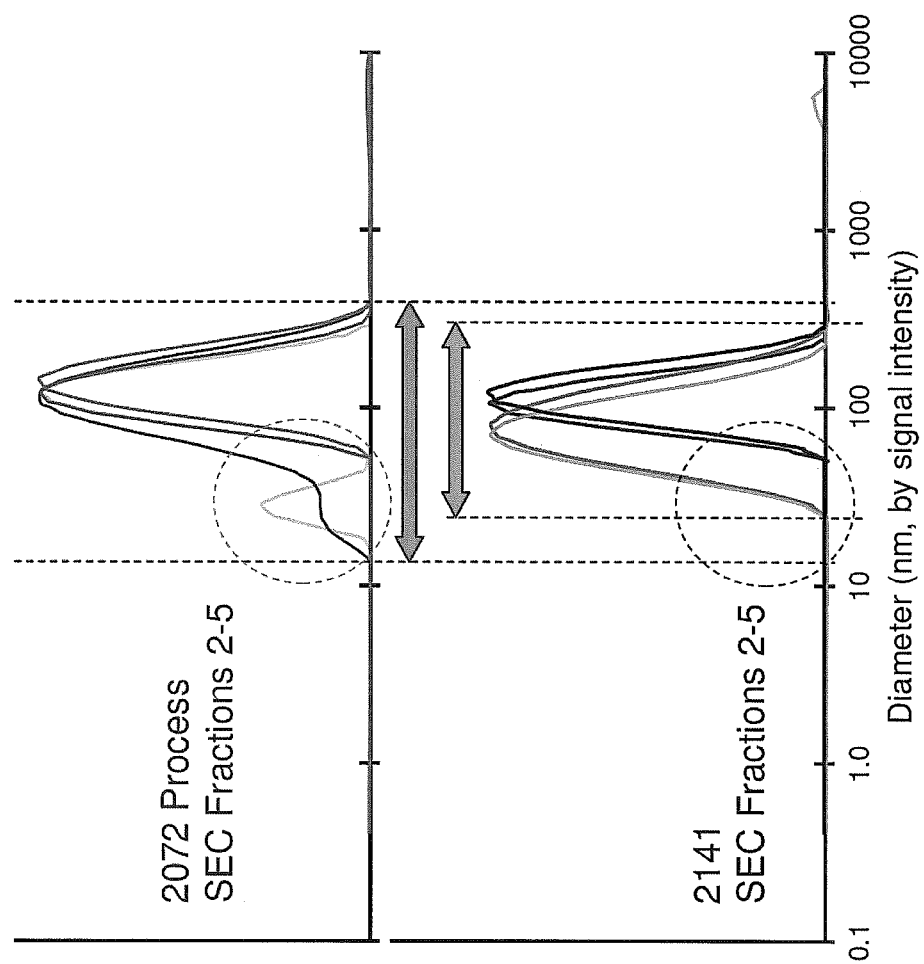
FIG. 3 shows the result of particle sizing experiments performed upon "2072" (top) and "2141" particle populations after initial performance of size-exclusion chromatography ("SEC") and selection of fractions 2-5.

Further evaluation of the physical characteristics of "2141"-produced and "2072"-produced particles revealed even more dramatic differences between the two particle populations. When both particle populations were subjected to size-exclusion chromatography ("SEC") and signal intensities were examined, the homogeneity of the "2141"-produced particles was especially striking. As shown in FIG. 3, SEC fractions 2-5 of a "2072"-produced particle population revealed significant heterogeneity of the particle population—specifically, the "2072" particle population of the top panel of FIG. 3 revealed a significant minor peak of lesser particle size than the main peak, which appeared to correspond to micelle debris; in contrast, the "2141"-produced particles of the bottom panel showed no such minor peak and sizing of "2141"-produced particles was more tightly clustered. Thus, particles made by the "2141 process" possessed a more consistent size and less micelle debris, as compared to particles produced by the "2072 process". This effect was particularly noteworthy because, as stated above, the lipid compositions of "2141"-produced and "2072"-produced particles were identical.

Figure 4:
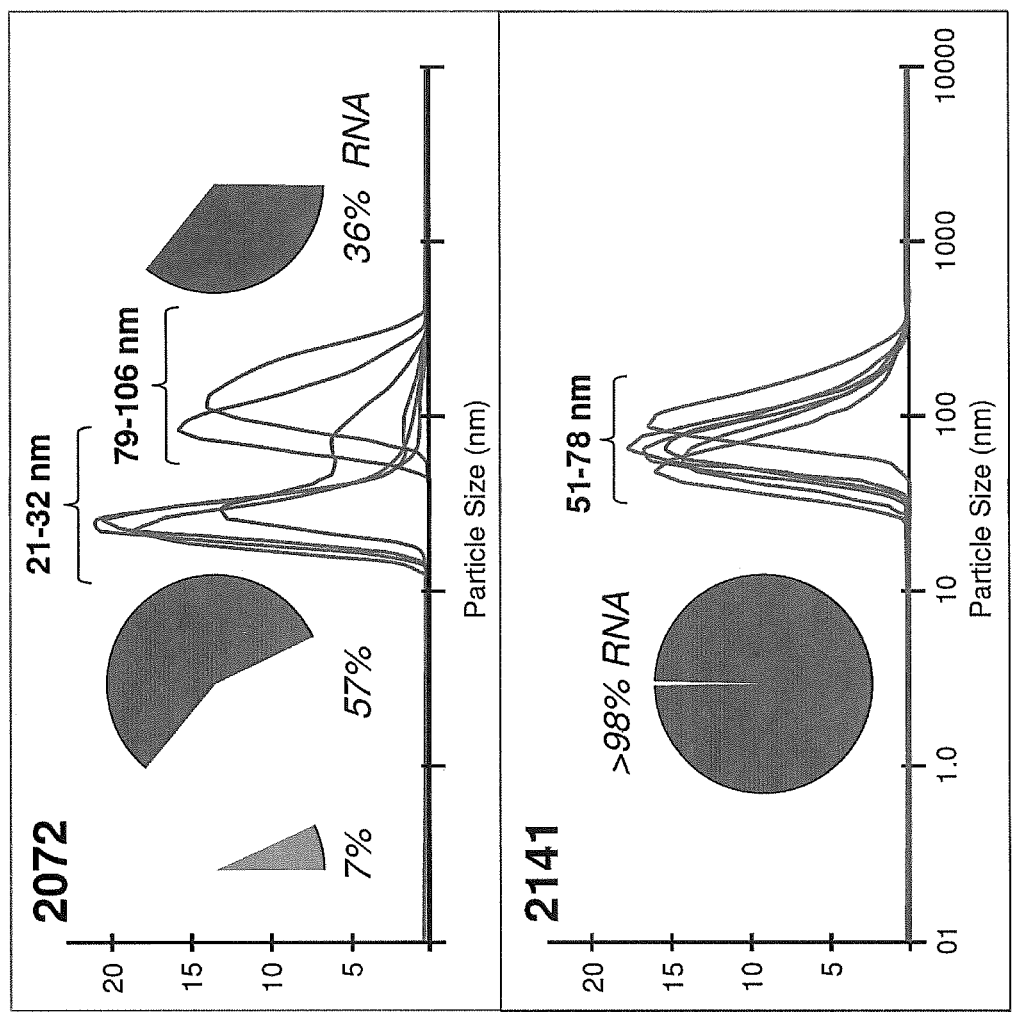
FIG. 4 shows percent volume particle size assay results for particles produced by the "2072" (top) and "2141" (bottom) processes.

Additional examination of "2141"-produced particles as compared to "2072"-produced particles further defined the relative homogeneity of the "2141"-produced particle population as compared to the heterogeneity of the "2072"-produced particle population. Percent volume analysis was performed using 1.0 ml of 1.0 mg/mL DsiRNA in LNP run on a Sepharose 4B column, 30 ml., and particles were measured by % volume, with RNA content for each fraction assessed by average particle size (Malvern). As shown in FIG. 4, when percent volume analysis was performed upon both "2072"- and "2141"-produced particles, "2072"-produced particles (FIG. 4, top panel) were observed to possess a majority fraction (57%) of 21-32 nm particles within the particle population, apparently corresponding to micelle debris, while only 36% of the "2072"-produced particle population corresponded to the 79-106 nm particles assessed to be the DsiRNA-containing particles. In contrast, "2141"-produced particles assessed by percent volume were remarkably homogeneous—greater than 98% of the particle population was identified in a 51-78 nm window that corresponded to DsiRNA-containing particles. Thus, the "2141 process" resulted in near-complete incorporation of DsiRNA payload into properly-sized particles, whereas the "2072 process" was observed under such stringent analyses to have accumulated a significant amount of micelle debris within the particle population.

Example 4

Figure 5:
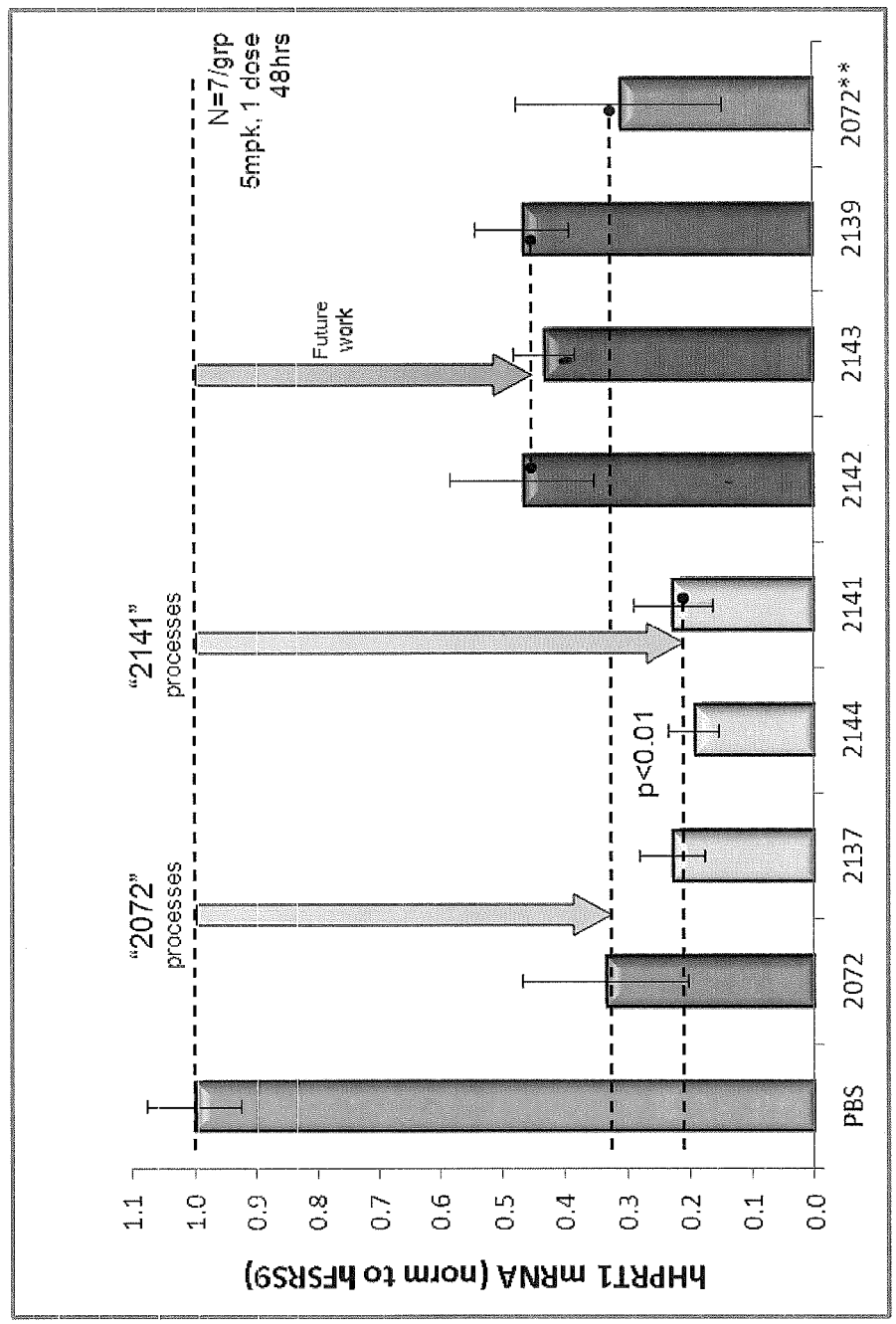
FIG. 5 shows in vivo target-specific knockdown results observed for particles harboring an HPRT1-targeting DsiRNA which were formulated by various indicated processes, including "2072" and "2141"-related processes "2141", "2137" and "2144". HPRT1 raw data was normalized to hSFRS9 levels and then plotted.

The "2141 Process" Produced Particles that Exhibited Enhanced Target-Specific Knockdown, Improved Phenotypic Activities, and that were Well-Tolerated The efficacy of "2141"-produced particles was assessed in vivo in a series of experiments. First, "2141"-formulated particles harboring an anti-HPRT1 payload DsiRNA as described above were examined for target-specific knockdown efficacy in mouse tumors (in such experiments, mice carrying Hep3B tumors were administered 5 mg/kg of particles ("2141" or others as indicated in FIG. 5), and liver tumor knockdown of HPRT1 was assessed at 48 hours post-administration, N=7/group). As shown in FIG. 5, particles made by the "2141 process" (which is also shared by "2137" and "2144" particles, with only proportions of component lipids varying between such these three groups) produced approximately 80% knockdown of HPRT1 in mouse tumors. This result was significantly better than that observed for particles made by the "2072 process", which resulted in approximately 70% knockdown of the targeted HPRT1 transcript in mouse tumors. Thus, the "2141 process", which is distinguished from the "2072 process" only in the elevated concentration of lipids present within the "additional lipids in ethanol" component of the process, produced a population of particles that was more effective at target-specific knockdown of a targeted transcript (here, HPRT1) in vivo. Without wishing to be bound by theory, at least part of this remarkable improvement was likely attributable to the dramatically improved homogeneity of particles obtained via the "2141 process".

Figure 6:
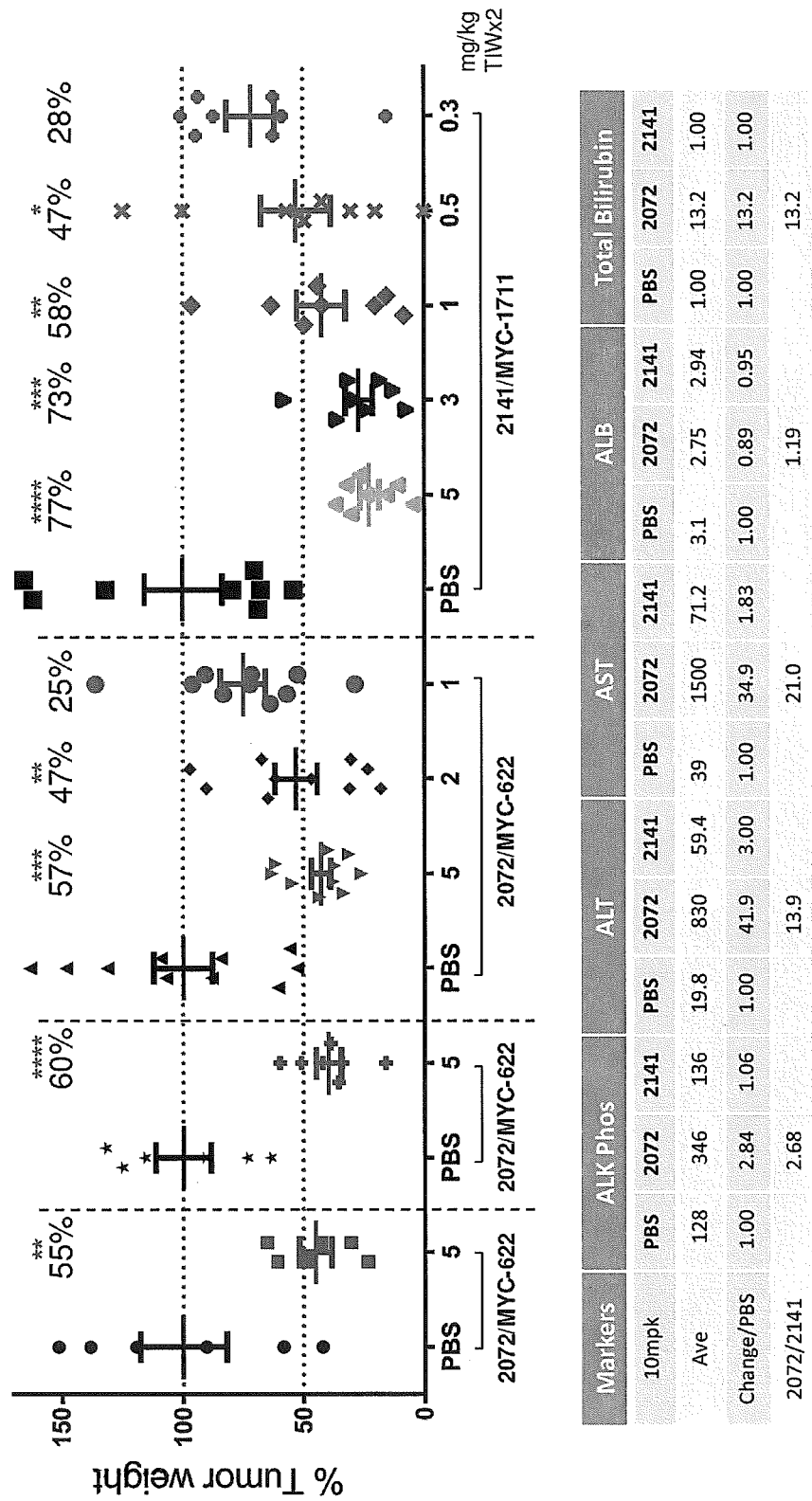
FIG. 6 demonstrates the in vivo efficacy and tolerability profiles of "2072"-produced particles and "2141"-produced particles, each harboring a MYC-targeting DsiRNA payload as indicated.

The in vivo phenotypic efficacy of "2141"-formulated particles as compared to "2072"-formulated particles was also examined. Within such experiments, two MYC-targeting DsiRNAs ("MYC-622" and "MYC-1711") were formulated using either the "2141 process" or the "2072 process". Particles containing these MYC-targeting DsiRNAs were then administered to mice harboring Hep3B tumors and efficacy was assessed (mice were dosed TIWx2 at concentrations indicated in FIG. 6, and tumor weights were assessed at 48 hours after administration of the final dose). In prior experiments, both MYC-622 and MYC-1711 payloads were observed to possess comparable efficacies (data not shown). As shown in FIG. 6, a MYC-1711 DsiRNA payload formulated in particles by the "2141 process" exhibited approximately 4-5-fold greater potency (efficacy scaled to level of dose) in reducing Hep3B tumor volume in vivo, as compared to "2072"-formulated particles harboring a MYC-622 DsiRNA. Specifically, "2141"-formulated particles harboring MYC-1711 payload administered at 3 mg/kg or 5 mg/kg exhibited respective reductions in tumor size of 73% and 77%, respectively. These levels of reduction were significantly greater than any observed for particles harboring MYC-targeting payload produced by the "2072 process", and even doses of less than 1 mg/kg of "2141"-formulated particles having anti-MYC payloads exhibited significant reductions in tumor size (approximately 28% reduction for 0.3 mg/kg and approximately 47% reduction for 0.5 mg/kg). Tolerability of the respective formulations was also assessed by examining the following toxicity markers: ALK Phos, ALT, AST, ALB and total bilirubin. As shown in the lower table of FIG. 6, particles produced by the "2072 process" raised levels of such toxicity markers to a much greater extent than was observed for particles produced by the "2141 process".

Figure 7:
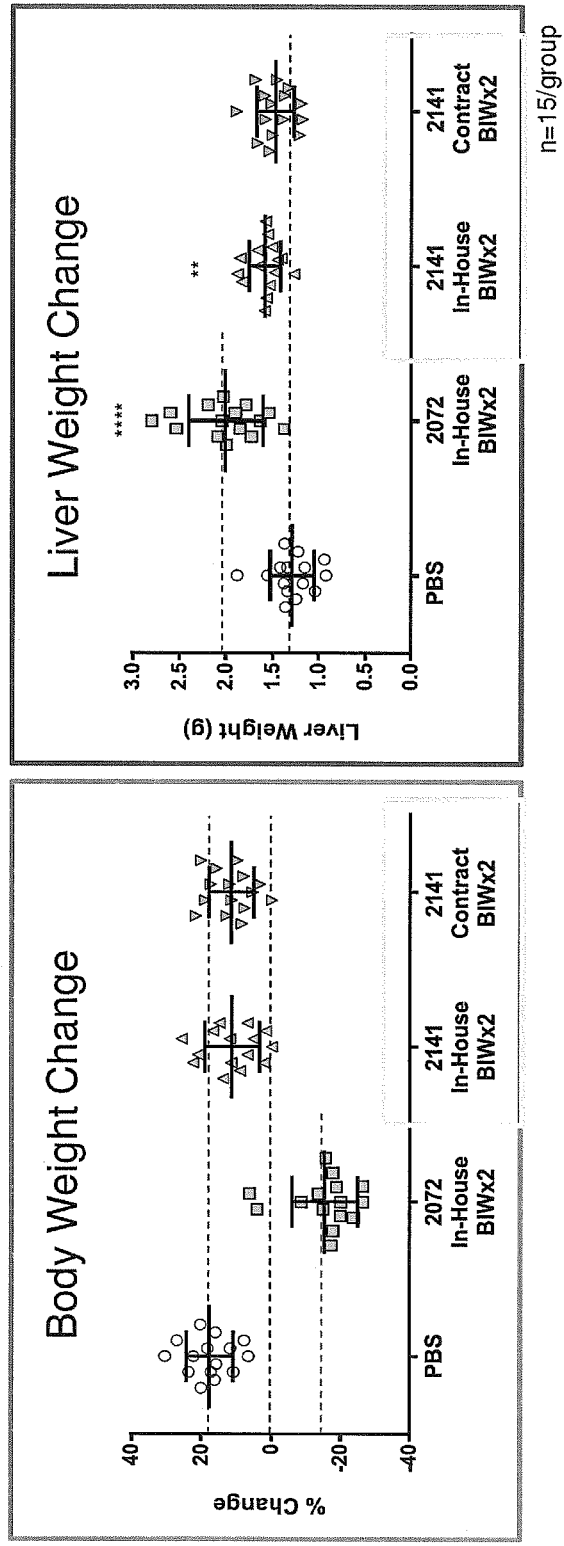
FIG. 7 demonstrates gross in vivo tolerabilities (body weights and liver weights) of "2072"-produced particles and "2141"-produced particles.

Additional assays were performed to assess the tolerability of particles produced by either the "2141 process" or the "2072 process", and all such assays underscored the enhanced tolerability/lack of toxicity of particles produced by the "2141 process". When a formulation is not well tolerated in a mouse, such a mouse will often show a loss of body weight following administration of such a formulation. Meanwhile, liver weight often increases for such mice. As shown in FIG. 7, gross tolerabilities of "2072"- and "2141"-produced particles were compared via evaluation of the impact upon body weight and liver weight of 10 mg/kg administration (BIWx2, four doses total, n=15/group) of such particles to mice. Remarkable differences between particles formulated by each of these processes were observed, with "2072"-formulated particles exhibiting a dramatic impact upon both body weight (administration of "2072"-formulated particles produced a reduction in body weight of almost 20%) and liver weight (an approximate 50% increase in liver weight was observed for mice administered the "2072"-formulated particles. In contrast, no significant impact upon body weight was observed for mice administered "2141"-formulated particles, and "2141"-formulated particles provoked only a very modest (approx. 10-20%) increase in liver weight, an effect that was also only observed in one of two "2141" preparations examined. Thus, "2141"-produced particles were remarkably well-tolerated, based upon gross indications of formulation tolerability, in vivo.

Figure 8:
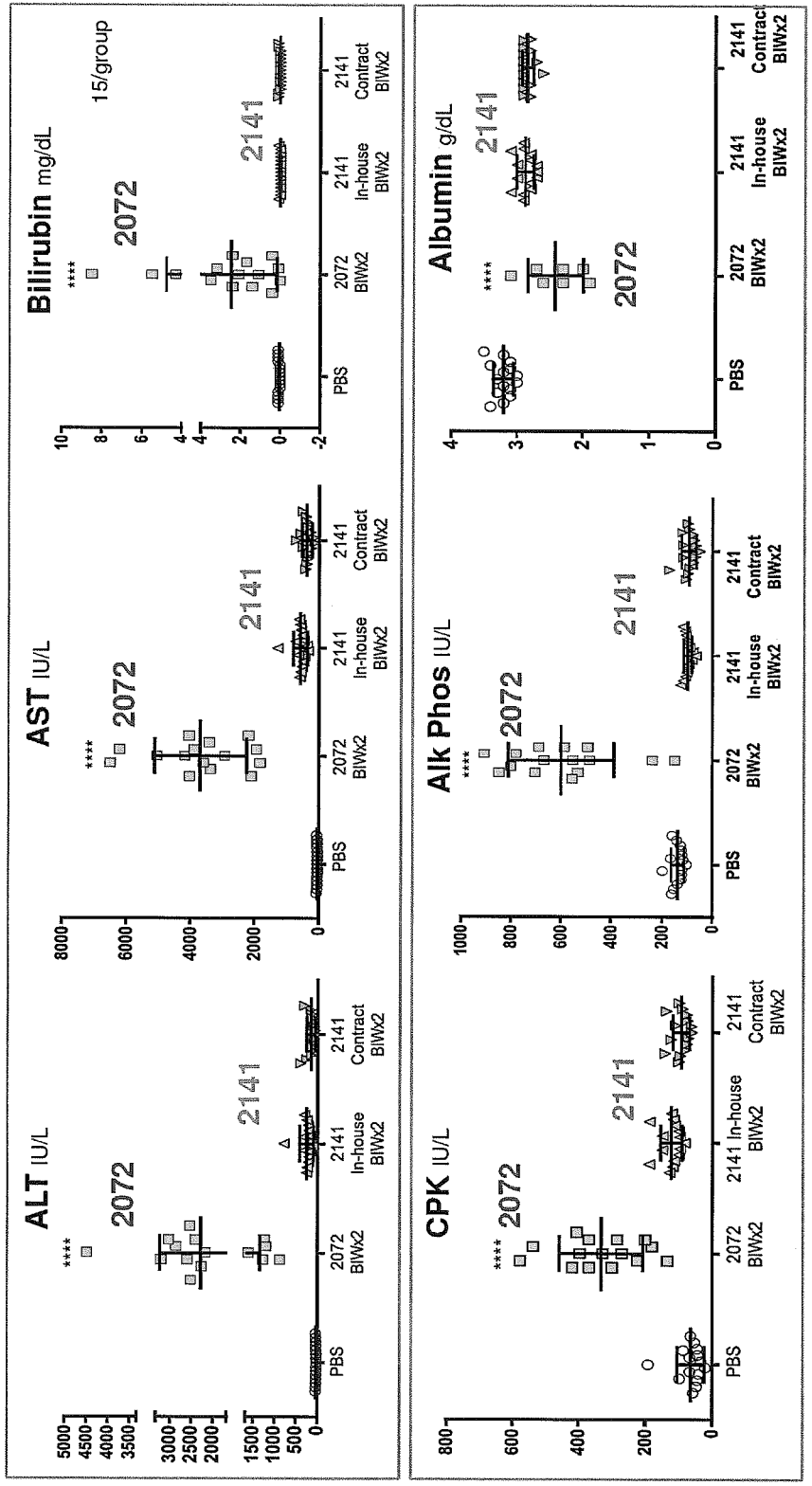
FIG. 8 shows the results of toxicity marker assessments for both "2072"-produced particles and "2141"-produced particles.

Such tolerability/toxicity results of the "2141"-formulated particles were reinforced by assessment of the following markers of toxicity in those mice administered the "2072"- and "2141"-formulated particles at 10 mg/kg administration (BIWx2, four doses total, n=15/group): ALT, AST, bilirubin, CPK, alkaline phosphatase, and albumin. As shown in FIG. 8, such elevated, repeated doses of "2072"-formulated particles provoked changes in each of these markers that were indicative of formulation toxicity: ALT, AST, bilirubin, CPK and alkaline phosphatase levels were all significantly elevated, while albumin levels were significantly reduced. In stark contrast, "2141"-formulated particles showed no such dramatic changes in the toxicity markers examined: none of the "2141"-formulated particles showed any significant change in such toxicity marker, as compared to parallel PBS-treated animals. Thus, the "2141 process" (which featured an elevated concentration of additional lipids in ethanol during the formulation process) produced particles that not only possessed improved physical characteristics (size, PDI, etc.), but also were more efficacious in vivo, as well as being better tolerated, than corresponding particles produced by methods that did not feature the use of elevated concentrations of additional lipids in ethanol during the formulation process.

Example 5

Processes and Formulations for Producing Anionic Agent-Containing Particles

Lipid compositions for use in the production of particles carrying anionic agents were formulated generally as described above for Examples 1 (the 2141 process) and according to the process shown in FIG. 1. The process includes preparing a first lipid suspension comprising core lipids including a cationic lipid such as DODMA, DL-048, DL-049, DL-033, and a modified lipid which prevents particle aggregation during lipid-anionic agent particle formulation, for example, a PEG-lipid conjugate such as DMPE-PEG2k, DMG-PEG2k, and DSPE-PEG2k. The core lipids are mixed in an acidic aqueous solution to form a lipid complex.

A second (additional) lipid solution is prepared in a solvent, for example, ethanol, preferably 100% ethanol. As shown Tables 7 and 8, the second lipid solution contains one or more lipid selected from the group consisting of a structural lipid, a sterol, a cationic lipid, and a modified lipid. Examples include DDPC, DSPC, MSPC, POPC, Lyso PC, POGP, Cholesterol, DL-033, DL-036, DMPD-PEG2k, DSPE-PEG2k, and DSG-PEG2k, and the like. Chemical abbreviations of compounds used in the formulations are defined below in Table 9.

Specific exemplary combinations of lipids for preparing the core first lipid composition and the second additional lipid compositions are listed in Tables 7 and 8, and were prepared as described above for Example 1and tested for specific properties. As described for Example 1, a preferred method for producing particles containing an anionic agent payload includes the steps of combining in an acidic aqueous solution, preferably an aqueous HCl solution, a modified lipid which prevents particle aggregation during lipid-anionic agent particle formation and a cationic lipid (for example, the core cationic lipids shown in Tables 7 and 8), in amount sufficient to form a complex. The lipid complex can then be combined with an anionic agent, such as a nucleic acid molecule, to form a complex-anionic agent, and combined with a neutral aqueous solution to form a complex-anionic agent aqueous suspension.

Additional lipids are combined to form an additional lipid solution or suspension, comprising one or more lipid selected from a structural lipid, a sterol, a cationic lipid, and a modified lipid. In a preferred embodiment, the additional lipids are combined in a solvent such as ethanol, preferably 100% ethanol, and preferably include one or more of the Envelope lipids shown in Tables 7 and 8. The solution or suspension of the additional Envelope lipids is preferably added to the complex-anionic agent to produce particles comprising the anionic agent.

Particles containing an antigentic agent were produced using the formulations described in Tables 7 and 8 and each of the formulations provided particles having the improved characteristics described for particles produced by the 2141 process as compared against particles made by the 2072 process described in Examples 1 and 2. The improved characteristics included homogenicity, uniformity, payload, and therapeutic efficacy.

As demonstrated in Table 10, the particles have improved characteristics over particles produced by the process of 2072 as measured by one or more of the following characteristics and/or markers: Average particle size, polydispersity index (PDI), percent payload, for example, nucleic acid in the particle and/or delivered to the target cell, disease markers alkaline phosphatase, CPK, ALT, AST, Albumin, total bilirubin, HPRT1, change in body weight or liver weight, for example, as measured in diagnostic assays representative of the payload and its target. See Table 10, below.

TABLE 7

EnCore LNP Formulation Compositions (% mol) - Tumor Centric
Tumor Centric
Encore LNP Formulation Compositions (% mol)

| | Lipid | 2141 | 2163 | 2311 | 2332 | 2376 |
|---|---|---|---|---|---|---|
| Core Lipids | DODMA | 25.9 | | | | |
| | DL-048 | | | 25.9 | | 25.9 |
| | DL-049 | | | | | |
| | DL-033 | | 25.2 | | 24.7 | |
| | DMPE-PEG2k | 2.9 | | 2.9 | | |
| | DMG-PEG2k | | | | | |
| | DSPE-PEG2k | | 2.8 | | 2.7 | 2.9 |
| | Total | 28.7 | 28.0 | 28.7 | 27.4 | 28.7 |
| Envelope Lipids | DPPC | | | | | |
| | DSPC | 13.8 | 13.4 | 13.8 | 13.2 | 13.8 |
| | MSPC | | | | | |
| | POPC | | | | | |
| | Lyso PC | | | | | |
| | POPG | | | | | |
| | CHOL | 33.1 | 32.2 | 33.1 | 31.6 | 33.1 |
| | DL-033 | | 21.0 | | | |
| | DL-036 | 21.6 | | 21.6 | 20.6 | 21.6 |
| | DMPE-PEG2k | | | | | |
| | DSPE-PEG2k | 2.8 | | 2.8 | | 2.8 |
| | DSG-PEG2k | | 5.3 | | 7.3 | |
| | Total | 71.3 | 72.0 | 71.3 | 72.6 | 71.3 |
| | Grand Total | 100.0 | 100.0 | 100.0 | 100.0 | 100.0 |
| | PC lipids (zwitterionic) | 13.8 | 13.4 | 13.8 | 13.2 | 13.8 |
| | PG lipids | 0.0 | 0.0 | 0.0 | 0.0 | 0.0 |
| | PO4-Group | 19.4 | 16.2 | 19.4 | 15.9 | 19.4 |
| | Asymmetric Lipids | 0.0 | 0.0 | 0.0 | 0.0 | 0.0 |
| | Ionizable (Positive) | 47.5 | 46.2 | 47.5 | 45.3 | 47.5 |
| | Ionizable (Negative) | N/A | N/A | N/A | N/A | N/A |
| | PEG Lipids | 5.6 | 8.1 | 5.6 | 10.0 | 5.6 |

TABLE 8

EnCore LNP Formulation Compositions - Liver Centric

Table 8. Liver Centic
EnCore #

| | Target | 2185/ 2325 | 2345 | 2357 | 2360 | 2361 | 2362 | 2363 | 2368 | 2372 | 2373 | 2386 | 2391 | 2408 | 2410 | 2411 | 2413 | 2414 | 2416 |
|---|---|---|---|---|---|---|---|---|---|---|---|---|---|---|---|---|---|---|---|
| Core | DODMA | | | | 24.7 | 27.6 | 31.2 | 35.8 | | | | | | | | | | | |
| | DL-048 | 26.6 | 25.3 | | | | | | 25.3 | 16.3 | 27.8 | 24.6 | 24.3 | 26.8 | 29.9 | 26.8 | 29.9 | 26.8 | 29.9 |
| | DL-049 | | | 25.3 | | | | | | | | | | | | | | | |
| | DL-033 | | | | | | | | | | | | | | | | | | |
| | DMPE-PEG2k | 2.9 | 2.8 | 2.8 | 2.7 | 3.0 | 3.4 | 4.0 | | | | | | 3.0 | 3.3 | 3.0 | 3.3 | 3.0 | 3.3 |
| | DMG-PEG2k | | | | | | | | 2.8 | 1.8 | 3.1 | 2.7 | 2.5 | | | | | | |
| | DSPE-PEG2k | | | | | | | | | | | | | | | | | | |
| | Total | 29.6 | 28.1 | 28.1 | 27.4 | 30.6 | 34.6 | 39.8 | 28.1 | 18.1 | 30.9 | 27.3 | 26.8 | 29.7 | 33.2 | 29.7 | 33.2 | 29.7 | 33.2 |
| ENV | DPPC | 14.2 | | | | | | | | | | | | | | | | | |
| | DSPC | | | | | | | | | | | | | | | | | | |
| | MSPC | | | | | | | | | | | | | | | 14.1 | 3.9 | | |
| | POPC | | | | | | | | | | | | | 14.1 | 3.9 | | | | |
| | Lyso PC | | | | | | | | | | | | | | | | | 14.1 | 3.9 |
| | POPG | | | | | | | | | | | 0.4 | 2.2 | | | | | | |

TABLE 8-continued

EnCore LNP Formulation Compositions - Liver Centric

Table 8. Liver Centic

| Target | 2185/2325 | 2345 | 2357 | 2360 | 2361 | 2362 | 2363 | 2368 | 2372 | 2373 | 2386 | 2391 | 2408 | 2410 | 2411 | 2413 | 2414 | 2416 |
|---|---|---|---|---|---|---|---|---|---|---|---|---|---|---|---|---|---|---|
| CHOL | 34.0 | 36.0 | 36.0 | 36.3 | 34.7 | 32.7 | 30.1 | 36.0 | 41.0 | 34.6 | 36.2 | 35.5 | 33.7 | 37.7 | 33.7 | 37.7 | 33.7 | 37.7 |
| DL-033 | | | | | | | | | | | | | | | | | | |
| DL-036 | 22.2 | 36.0 | 36.0 | 36.3 | 34.7 | 32.7 | 30.1 | 36.0 | 41.0 | 34.6 | 36.2 | 35.5 | 22.5 | 25.1 | 22.5 | 25.1 | 22.5 | 25.1 |
| DMPE-PEG2k | | | | | | | | | | | | | | | | | | |
| DSPE-PEG2k | | | | | | | | | | | | | | | | | | |
| DSG-PEG2k | | | | | | | | | | | | | | | | | | |
| Total | 70.4 | 71.9 | 71.9 | 72.6 | 69.4 | 65.4 | 60.2 | 71.9 | 81.9 | 69.1 | 72.7 | 73.2 | 70.3 | 66.8 | 70.3 | 66.8 | 70.3 | 66.8 |
| Grand Total | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |

TABLE 9

Chemical Names

| Abbreviation | Chemical name | CAS # |
|---|---|---|
| DPPC | 1,2-dipalmitoyl-sn-glycero-3-phosphocholine | 63-89-8 |
| DSPC | 1,2-distearoyl-sn-glycero-3-phosphocholine | 816-94-4 |
| MSPC | 1-myristoyl-2-stearoyl-sn-glycero-3-phosphocholine | 76343-22-1 |
| POPC | 1-palmitoyl-2-oleoyl-sn-glycero-3-phosphocholine | 26853-31-6 |
| Lyso PC | 1-palmitoyl-2-hydroxy-sn-glycero-3-phosphocholine | 17364-16-8 |
| POPG | 1-hexadecanoyl-2-(9Z-octadecenoyl)-sn-glycero-3-phospho-(1'-rac-glycerol) | 268550-95-4 |
| CHOL | cholesterol | 57-88-5 |
| DMPE-PEG2k | 1,2-dimyristoyl-sn-glycero-3-phosphoethanolamine-N-[methoxy(polyethylene glycol)-2000] | 474922-82-2 |
| DMG-PEG2k | 1,2-Dimyristoyl-sn-glycerol, methoxypolyethylene Glycol-2000 | |
| DSPE-PEG2k | 1,2-distearoyl-sn-glycero-3-phosphoethanolamine-N-[methoxy(polyethylene glycol)-2000] | 474922-77-5 |
| DSG-PEG2k | 1,2-Distearoyl-sn-glycerol, methoxypolyethylene Glycol-2000 | 308805-39-2 |
| DODMA | 1,2-dioleyloxy-N,N-dimethylaminopropane | 104162-47-2 |
| DL-048 | Dioleyl-N,N-DimethylGlycine | |
| DL-049 | Dioleyl-N,N-DimethylGlycine | |
| DL-033 | DiLin-N-Methylpiperazine | |
| DL-036 | DiLin-N,N-DimethylGlycine | |

TABLE 10

Improved Particle Characteristics and Efficacy

| Formulation | PSD (nm) | PDI | % RNA Encap | Table 10 Composition | | | | | Tumor $KD_{50}$ (mpk) | Liver $KD_{50}$ (μg/kg) | Note |
|---|---|---|---|---|---|---|---|---|---|---|---|
| 2141 | 100 ± 10 | ≤0.15 | ≥85% | DODMA | DMPE-PEG2k | DSPC | CHOL | DL-036 | DSPE-PEG2k | 0.5 to 1 in HCC | |
| 2163 | 90 ± 10 | ≤0.15 | ≥85% | DL-033 | DSPE-PEG2k | DSPC | CHOL | DL-033 | DSG-PEG2k | <0.5 in HCC | |
| 2311 | 100 ± 10 | ≤0.15 | ≥85% | DL-048 | DMPE-PEG2k | DSPC | CHOL | DL-036 | DSPE-PEG2k | 0.5 to 1 in HCC | |
| 2332 | 90 ± 10 | ≤0.15 | ≥85% | DL-033 | DSPE-PEG2k | DSPC | CHOL | DL-033 | DSG-PEG2k | to 5 in Prostate | | Very high PEG content |
| 2376 | 100 ± 10 | ≤0.15 | ≥85% | DL-048 | DSPE-PEG2k | DSPC | CHOL | DL-036 | DSPE-PEG2k | 0.5 to 1 in HCC | |
| 2185/2325 | 100 ± 10 | ≤0.15 | ≥85% | DL-048 | DMPE-PEG2k | DPPC | CHOL | DL-036 | N/A | N/A | 20 to 50 |
| 2345 | 105 ± 15 | ≤0.15 | ≥85% | DL-048 | DMPE-PEG2k | N/A | CHOL | DL-036 | N/A | N/A | 10 to 20 PC free |
| 2357 | 105 ± 15 | ≤0.15 | ≥85% | DL-049 | DMPE-PEG2k | N/A | CHOL | DL-036 | N/A | N/A | 10 to 20 PC free |
| 2360 | 105 ± 15 | ≤0.15 | ≥85% | DODMA | DMPE-PEG2k | N/A | CHOL | DL-036 | N/A | N/A | 10 to 20 PC free |
| 2368 | 105 ± 15 | ≤0.15 | ≥85% | DL-048 | DMG-PEG2k | N/A | CHOL | DL-036 | N/A | N/A | 10 to 20 $PO_4$ group free |
| 2386 | 105 ± 15 | ≤0.15 | ≥85% | DL-048 | DMG-PEG2k | POPG (0.5%) | CHOL | DL-036 | N/A | N/A | 10 to 20 PG containing |
| 2391 | 105 ± 15 | ≤0.15 | ≥85% | DL-048 | DMG-PEG2k | POPG (3%) | CHOL | DL-036 | N/A | N/A | 10 to 20 PG containing |
| 2408 | 100 ± 15 | ≤0.15 | ≥85% | DL-048 | DMPE-PEG2k | POPC (20%) | CHOL | DL-036 | N/A | N/A | 20 to 50 Asymmetric acyl chains |

TABLE 10-continued

Improved Particle Characteristics and Efficacy

| Formulation | PSD (nm) | PDI | % RNA Encap | Table 10 Composition | | | | | Tumor $KD_{50}$ (mpk) | Liver $KD_{50}$ (μg/kg) | Note |
|---|---|---|---|---|---|---|---|---|---|---|---|
| 2410 | 100 ± 15 | ≤0.15 | ≥85% | DL-048 | DMPE-PEG2k | POPG (5%) | CHOL | DL-036 | N/A | N/A | 20 to 50 Same as above |
| 2411 | 100 ± 15 | ≤0.15 | ≥85% | DL-048 | DMPE-PEG2k | MSPC (20%) | CHOL | DL-036 | N/A | N/A | 20 to 50 Same as above |
| 2413 | 100 ± 15 | ≤0.15 | ≥85% | DL-048 | DMPE-PEG2k | MSPC (5%) | CHOL | DL-036 | N/A | N/A | 20 to 50 Same as above |
| 2414 | 100 ± 15 | ≤0.15 | ≥85% | DL-048 | DMPE-PEG2k | Lyso PC (C16, 20%) | CHOL | DL-036 | N/A | N/A | 20 to 50 Same as above |
| 2416 | 100 ± 15 | ≤0.15 | ≥85% | DL-048 | DMPE-PEG2k | Lyso PC (C16, 5%) | CHOL | DL-036 | N/A | N/A | 20 to 50 Same as above |

Example 6

Liver Centric Formulations: HAO1 Knockdown

Additional lipid-nucleic acid formulations were prepared as described for example according to the 2041 process and tested for effective production of therapeutic particles, and to determine a minimum dose and frequency sufficient for HAO1 gene and protein knockdown. DsiRNA targeting HAO was formulated in EnCore lipid particles according to the specific formulations shown below in Table 11 and prepared as described for Example 1, the 2141 process. Formulations 2401 and 2373 contained the same combination of lipids and nucleic acid agent, but differed in that the 2401 process included in-line mixing of the envelope lipid solution or suspension with the complex-anionic agent aqueous suspension, whereas the 2373 process utilized batch mixing.

Particles were injected intraveneouly into female mice and animals were sacrificed 24 and 168 hours post dosing. Plasma and liver tissue samples were collected for analysis of hydroxyacid oxidase 1 (HAO1) gene and protein expression. The targeting DsiRNA was an RNAi agent (DsiRNA for MAO1), having the following sequences, respectively SEQ ID NO: 7 and 8. Note that while Antisense SEQ ID NO: 8 is shown below in 3'-5' orientation, in the Sequence Listing, all sequences are presented in 5'-3' orientation.

Sense:
(SEQ ID NO: 7)
5'-rAmUrAmUrUmUrUrCrCrCrArUrCmUrGmUrAmUrUrA
rUrUrUTT-3'

AntiSense:
(SEQ ID NO: 8)
3'-mAmAmAmArArUrArAmUrAmCrAmGrAmUrGrGrGrArA
rArAmUrAmUmUmG-5'*

In this study, the efficacy of particles produced with POPG as an envelope lipid was compared with DPPC. Particles contained varied amounts of POPG from 0.5% to 3%, while other components, including envelope lipids Cholesterol and DL-036 and Core lipids DL-048 and DMG-PEG2k were constant across all formulations. See Table 10 below.

Particles were prepared as disclosed above for Examples 1 and 5, using the specific formulations described in Table 11 below, and DsiRNA formed from SEQ ID NOs: 7 and 8, which was designed to interfere with the cellular target, MAO1.

Figure 9:
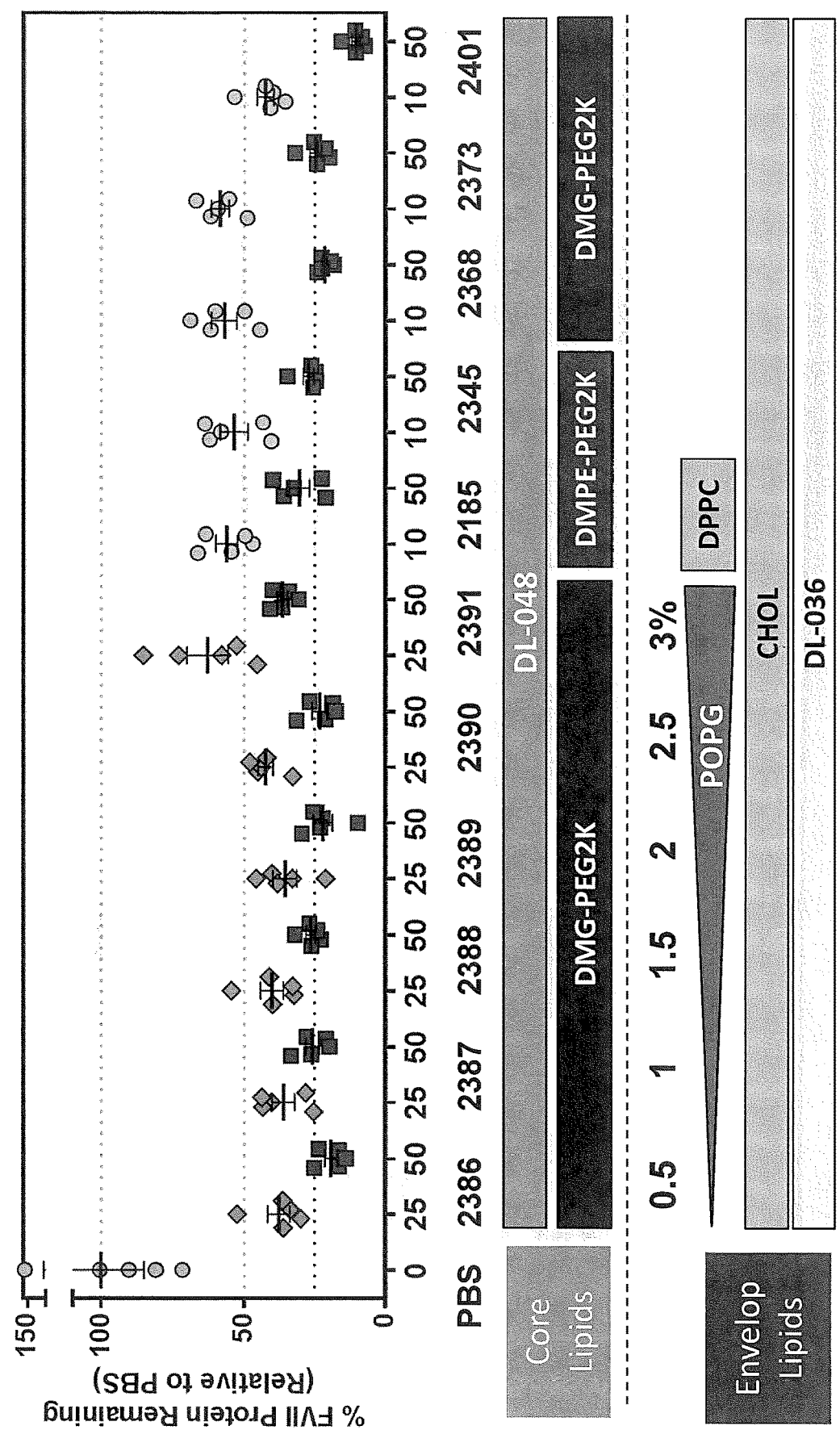
FIG. 9 shows results of efficacy testing for Example 6.

For this study, formulations containing murine FVII DsiRNA payload were intravenously injected into CB57-BL6 female mice at 10 ug/kg (circles), 25 ug/kg (diamonds), or 50 ug/kg (squares) as indicated in FIG. 9. Serum samples were collected 24 hour post dosing to access the reduction FVII protein using activity assay. PBS was included as negative control. Different EnCore formulations were labeled with individual 4 digit numbers as indicated in the Table 11 and FIG. 9. Different compositions of lipids were used for each formulation as shown on the bottom of the Figure.

The particles were tested for improved efficacy by analyzing presence of Factor VII in the mice receiving the interfereing therapeutic molecule via the lipid particles. The assay measured conversion of human factor X, a substrate of Factor VII, to Factor Xa, a reaction that then acted upon sXa-11, a chromogenic substrate, to produce color measured at 405 nm. The data are shown in Table 11 and FIG. 9.

TABLE 11

Formulations for Liver Centric Efficacy Screen

| | | | Liver Cenrtic EnCore # | | | | | | | | | |
|---|---|---|---|---|---|---|---|---|---|---|---|---|
| | Target | 2185/ 2325 | 2345 | 2368 | 2373 | 2386 | 2387 | 2388 | 2389 | 2390 | 2391 | 2401 |
| Core | DL-048 | 26.6 | 25.3 | 25.3 | 27.8 | 27.0 | 26.9 | 26.8 | 26.7 | 26.6 | 26.5 | 27.8 |
| | DMPE-PEG2k | 2.9 | 2.8 | | | | | | | | | |
| | DMG-PEG2k | | | 2.8 | 3.1 | 3.0 | 3.0 | 3.0 | 3.0 | 3.0 | 3.0 | 3.1 |
| | Total | 29.6 | 28.1 | 28.1 | 30.9 | 30.0 | 29.9 | 29.8 | 29.7 | 29.6 | 29.5 | 30.9 |
| ENV | DPPC | 14.2 | | | | | | | | | | |
| | POPG | | | | | 0.4 | 0.8 | 1.1 | 1.4 | 1.8 | 2.1 | |

TABLE 11-continued

Formulations for Liver Centric Efficacy Screen

| | Liver Cenrtic EnCore # | | | | | | | | | | |
|---|---|---|---|---|---|---|---|---|---|---|---|
| Target | 2185/ 2325 | 2345 | 2368 | 2373 | 2386 | 2387 | 2388 | 2389 | 2390 | 2391 | 2401 |
| CHOL | 34.0 | 36.0 | 36.0 | 34.6 | 34.8 | 34.7 | 34.5 | 34.4 | 34.3 | 34.2 | 34.6 |
| DL-036 | 22.2 | 36.0 | 36.0 | 34.6 | 34.8 | 34.7 | 34.5 | 34.4 | 34.3 | 34.2 | 34.6 |
| Total | 70.4 | 71.9 | 71.9 | 69.1 | 70.0 | 70.1 | 70.2 | 70.3 | 70.4 | 70.5 | 69.1 |
| Grand Total | 100.0 | 100.0 | 100.0 | 100.0 | 100.0 | 100.0 | 100.0 | 100.0 | 100.0 | 100.0 | 100.0 |

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

Listing of the Sequences disclosed herein:

| SEQ ID NO: | NA/ Protein | Species | Sequence 5'-3' * |
|---|---|---|---|
| 1 | NA | synthetic | GCCAGACUUUGUUGGAUUUG AAAtt |
| 2 | NA | synthetic | AAUUUCAAAUCCAACAAAGU CUGGCUU |
| 3 | NA | synthetic | AGGAACUAUGACCUCGACUA CGAct |
| 4 | NA | synthetic | UGUCCUUGAUACUGGAGCUG AUGCUGA |
| 5 | NA | synthetic | AGCUUUUUGCCCUGCGUGA CCAga |
| 6 | NA | synthetic | CCUCGAAAAACGGGACGCA CUGGUCU |
| 7 | NA | synthetic | rAmUrAmUrUmUrUrCrCrC rArUrCmUrGmUrAmUrUrA rUrUrUTT |
| 8 | NA | synthetic | GUmUmAmUrAmArArArGrG rGrUrAmGrAmCrAmUrAmA rUrArArmAmAmAm |

* where UPPERCASE letters signify to RNA nucleotide, underlined uppercase letters signify a 2'-O-methyl-RNA nucleotide, and lowercase letters signify a DNA nucleotide.

We claim:

1. A method of producing a particle comprising a first lipid or sterol, a second lipid or sterol and an anionic agent comprising:
   (a) combining said second lipid or sterol with an alcohol to form a second lipid or sterol solution in said alcohol, wherein said alcohol is free of said first lipid or sterol;
   (b) adding said second lipid or sterol solution in said alcohol of step (a) to said first lipid or sterol, thereby causing a concentration of said alcohol in said first lipid or sterol to increase from 0% to up to no more than 40% (v/v) as more of said second lipid or sterol solution in said alcohol of step (a) is added to said first lipid or sterol to form a solution of the second lipid or sterol and the first lipid or sterol, wherein the solubility of said first lipid or sterol in said alcohol in the presence of said second lipid or sterol is higher than the solubility of said first lipid or sterol in said alcohol in the absence of said second lipid or sterol; and
   (c) combining the solution of the second lipid or sterol and the first lipid or sterol of step (b) with a complex-anionic agent comprising (i) a modified lipid which prevents particle aggregation during lipid-anionic agent particle formation, (ii) a cationic lipid, in an amount sufficient for a complex to form, and (iii) an anionic agent,
   thereby producing a particle comprising a first lipid or sterol, a second lipid or sterol and an anionic agent.

2. The method of claim 1, wherein said solution of the second lipid or sterol and the first lipid or sterol comprises at least one lipid selected from the group consisting of a neutral lipid, a sterol, a cationic lipid and a modified lipid which prevents particle aggregation during lipid-anionic agent particle formation.

3. The method of claim 1, wherein said particle possesses a property selected from the group consisting of improved size and/or PDI, improved efficacy in a subject administered said particle and improved tolerability in a subject administered said particle, as compared to an appropriate control particle formed by an appropriate control process that comprises exposing said first lipid or sterol to said alcohol before said second lipid or sterol is exposed to said alcohol.

4. The method of claim 1, wherein said anionic agent is a nucleic acid.

5. The method of claim 4, wherein said nucleic acid is selected from the group consisting of an antisense oligonucleotide and a double-stranded nucleic acid.

6. The method of claim 5, wherein said double-stranded nucleic acid is selected from the group consisting of a small hairpin RNA (shRNA) and a siRNA.

7. The method of claim 6, wherein said double-stranded nucleic acid is a substrate for human Dicer.

8. The method of claim 1, wherein said first lipid or sterol is a sterol selected from the group consisting of cholesterol, cholestanone, cholestenone, coprostanol, 3β-[-(N—(N',N'-dimethylaminoethane)-carbamoyl]cholesterol (DC-cholesterol) and bis-guanidium-tren-cholesterol (BGTC).

9. The method of claim 1, wherein said alcohol is ethanol.

10. A method of producing a particle comprising a first lipid or sterol, a second lipid or sterol and an anionic agent comprising:
    (a) combining in an acidic aqueous solution (i) a modified lipid which prevents particle aggregation during lipid-anionic agent particle formation and (ii) a cationic lipid, in an amount sufficient for a complex to form;
    (b) combining the complex of step (a) with an anionic agent;
    (c) combining a neutral aqueous solution with the complex-anionic agent of step (b) to form a complex-anionic agent aqueous suspension;
    (d) combining said second lipid or sterol with an alcohol to form a second lipid or sterol solution in said alcohol, wherein said alcohol is free of said first lipid or sterol;
    (e) adding said second lipid or sterol solution in said alcohol to said first lipid or sterol, thereby causing a concentration of said alcohol in said first lipid or sterol to increase from 0% to up to no more than 40% (v/v) as more of said second lipid or sterol solution in said alcohol of step (d) is added to said first lipid or sterol to form a solution of the second lipid or sterol and the first lipid or sterol; and
    (f) combining the solution of the second lipid or sterol and the first lipid or sterol of step (e) with the complex-anionic agent aqueous solution of step (c),
    thereby producing a particle comprising a first lipid or sterol, a second lipid or sterol and an anionic agent.

11. The method of claim 10, wherein the solubility of said first lipid or sterol in said alcohol in the presence of said second lipid or sterol in step (e) is higher than the solubility of said first lipid or sterol in said alcohol in the absence of said second lipid or sterol.

12. The method of claim 10, wherein step (f) is performed by adding the solution of the second lipid or sterol and the first lipid or sterol of step (d) to the complex-anionic agent aqueous suspension of step (c) or in-line mixing of the solution of the second lipid or sterol and the first lipid or sterol of step (d) and the complex-anionic agent aqueous solution of step (c).

13. The method of claim 10, wherein said first lipid or sterol is a sterol selected from the group consisting of cholesterol, cholestanone, cholestenone, coprostanol, 3β-[-(N—(N',N'-dimethylaminoethane)-carbamoyl]cholesterol (DC-cholesterol) and bis-guanidium-tren-cholesterol (BGTC).

14. The method of claim 10, wherein said alcohol is ethanol.

15. The method of claim 10, wherein said acidic aqueous solution of step (a) comprises HCl.

16. The method of claim 10, wherein said modified lipid is a polyethylene glycol (PEG)-, PEG-ceramide, or ganglioside-modified lipid.

17. The method of claim 10, wherein the cationic lipid is one or more of DODMA, DOTMA, or a cationic lipid selected from the group consisting of L-1 to L-49:

L-1 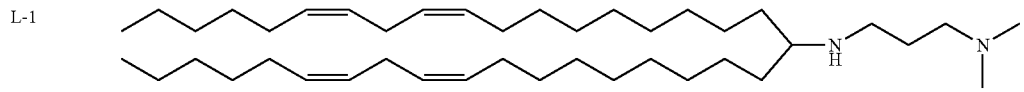

L-2 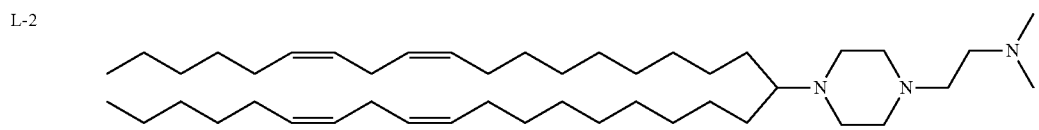

-continued
L-3
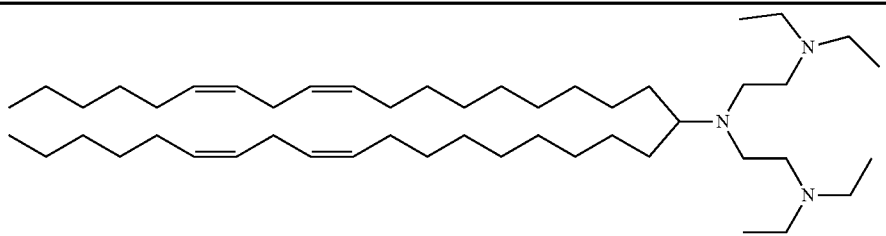
L-4
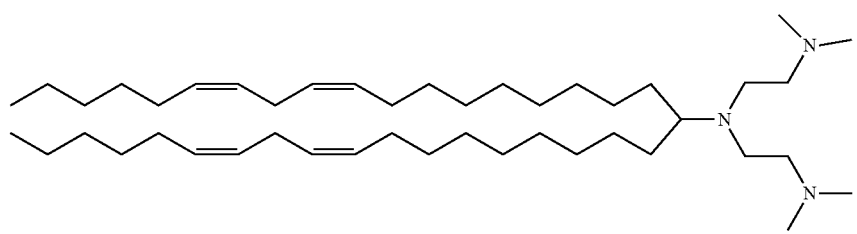 [SMILES: CCCCC/C=C\C/C=C\CCCCCCCCC(CCCCCCCC/C=C\C/C=C\CCCCC)N(CCN(C)C)CCN(C)C]
L-5
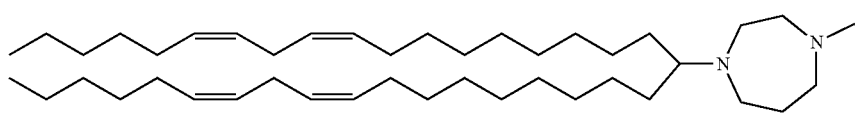
L-6
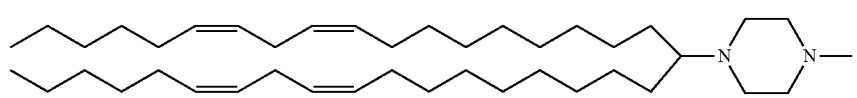
L-7
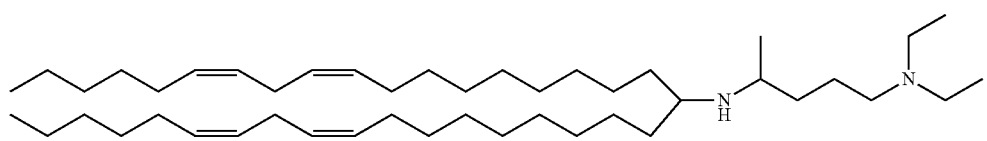 [SMILES: CCCCC/C=C\C/C=C\CCCCCCCCC(CCCCCCCC/C=C\C/C=C\CCCCC)NC(C)CCCN(CC)CC]
L-8
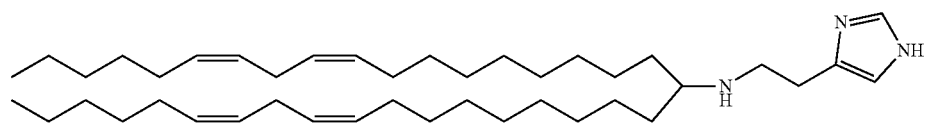
L-9
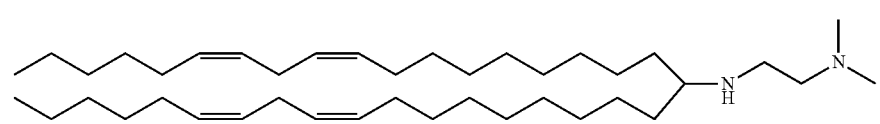 [SMILES: CCCCC/C=C\C/C=C\CCCCCCCCC(CCCCCCCC/C=C\C/C=C\CCCCC)NCCN(C)C]
L-10
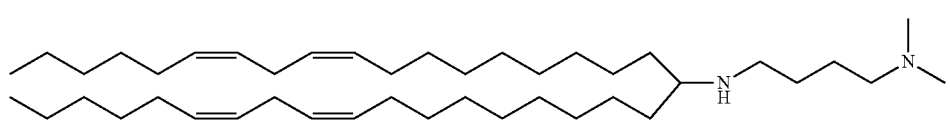
L-11
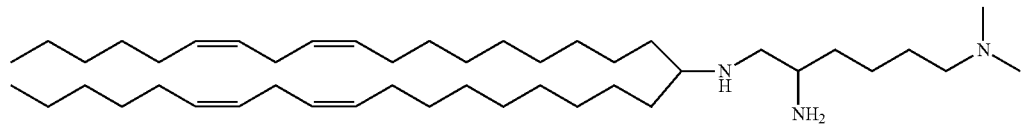
L-12
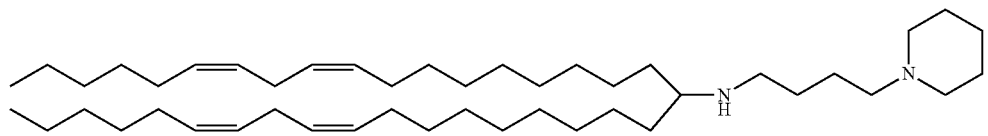
L-13
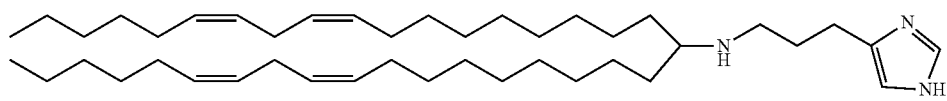

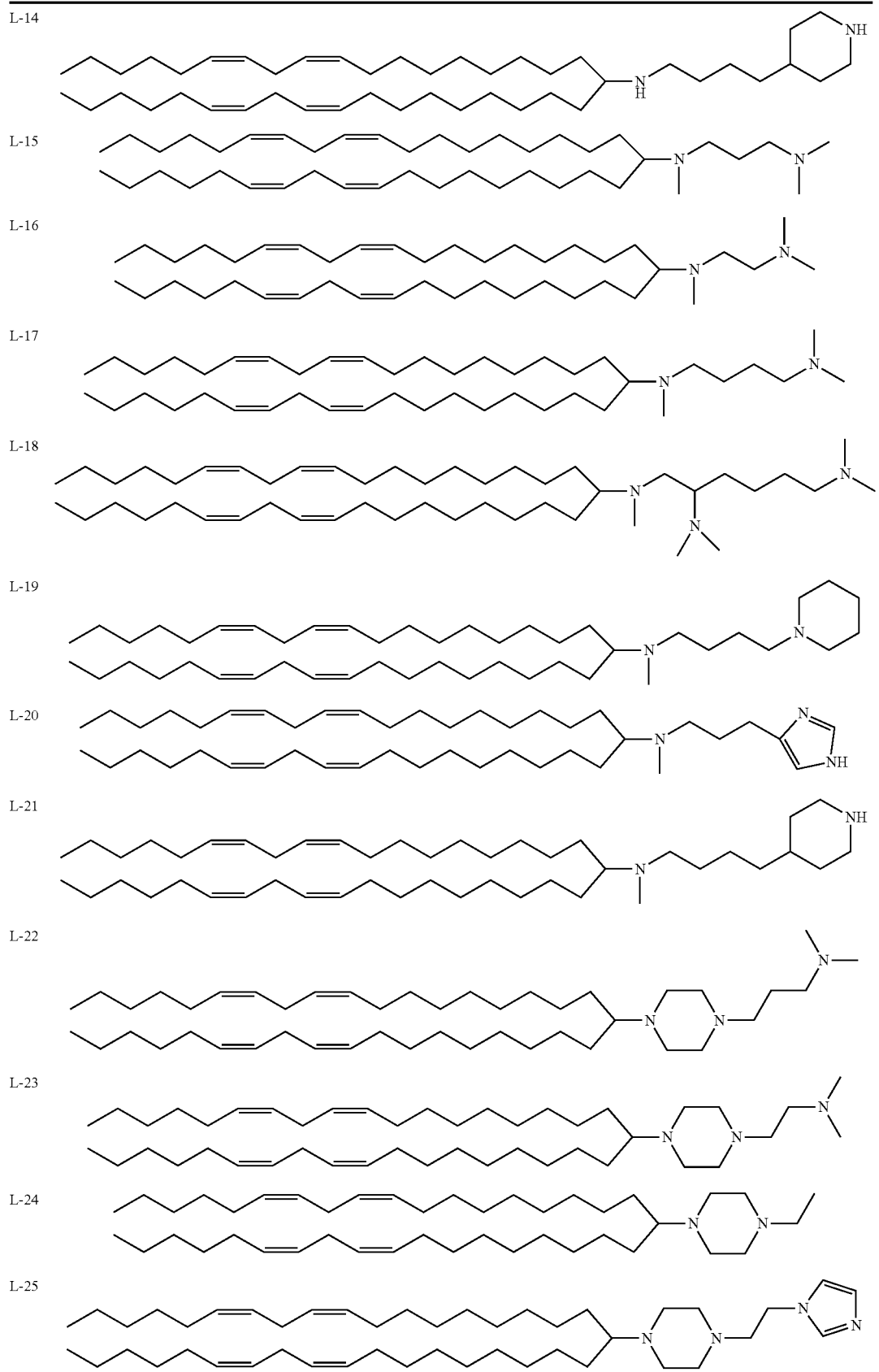

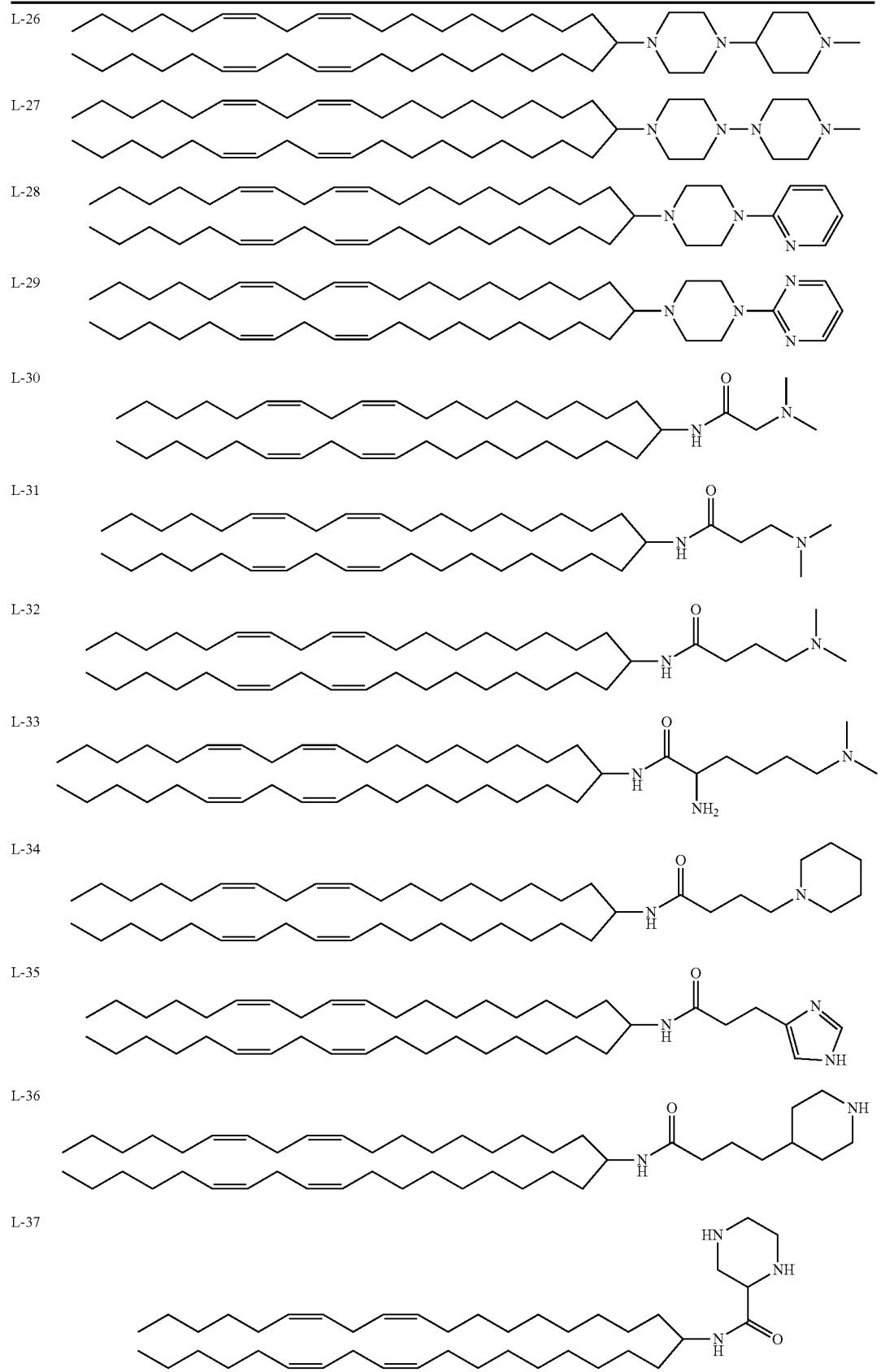

L-38
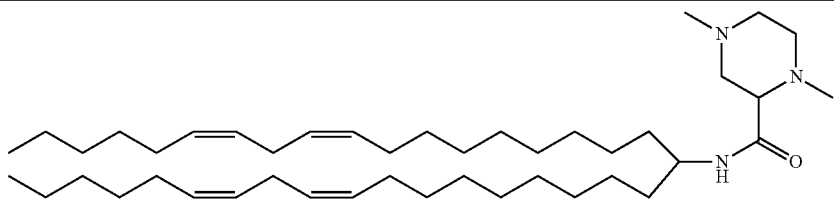
L-39
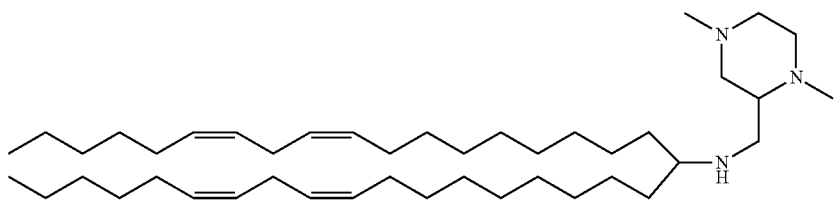 [SMILES: CCCCC/C=C\C/C=C\CCCCCCCCC(CCCCCCCC/C=C\C/C=C\CCCCC)NCC1CN(C)CCN1C]
L-40
L-41
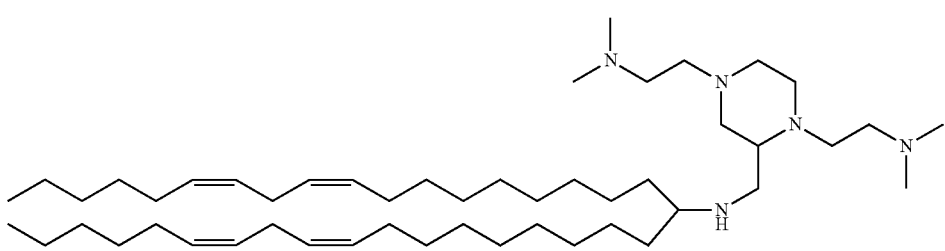 [SMILES: CCCCC/C=C\C/C=C\CCCCCCCCC(CCCCCCCC/C=C\C/C=C\CCCCC)NCC1CN(CCN(C)C)CCN1CCN(C)C]
L-42
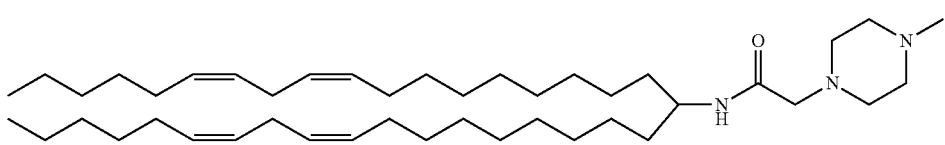 [SMILES: CCCCC/C=C\C/C=C\CCCCCCCCC(CCCCCCCC/C=C\C/C=C\CCCCC)NC(=O)CN1CCN(C)CC1]
L-43
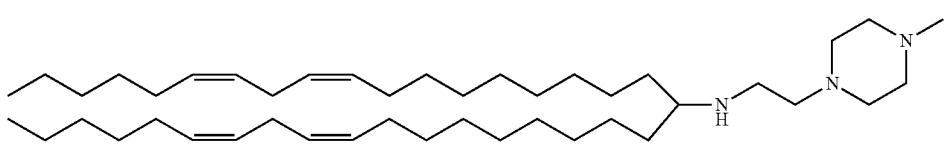
L-44
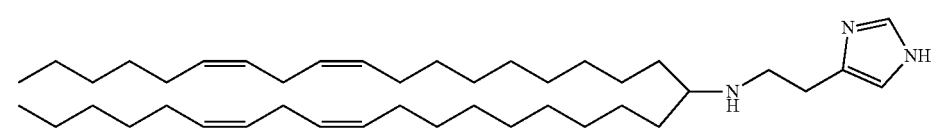 [SMILES: CCCCC/C=C\C/C=C\CCCCCCCCC(CCCCCCCC/C=C\C/C=C\CCCCC)NCCc1c[nH]cn1]
L-45
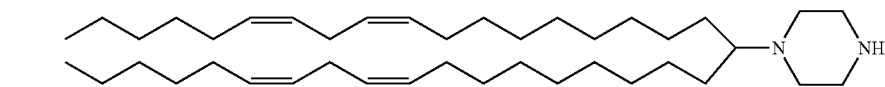
L-46
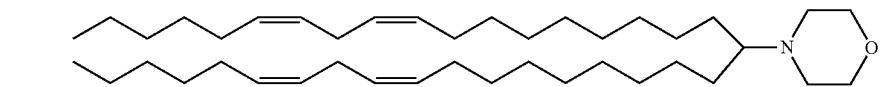
L-47
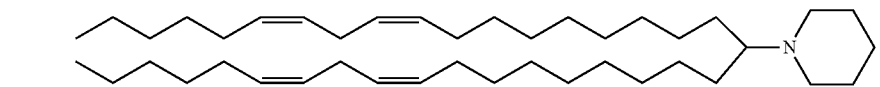

| | |
|---|---|
| L-48 | 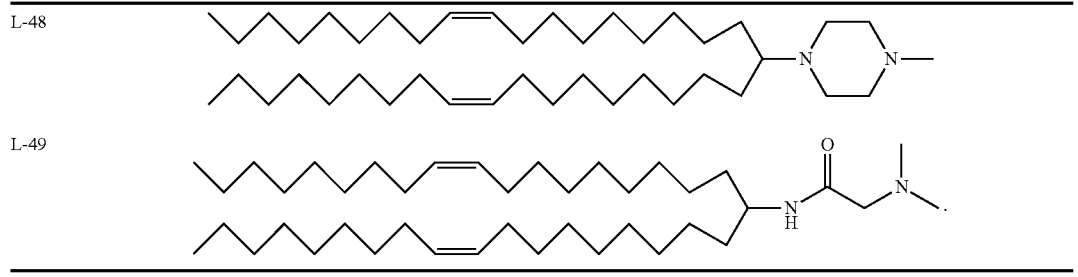 |
| L-49 | |

18. The method of claim 10, wherein the cationic lipid has the formula:

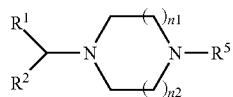

wherein each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; each n1 and n2 is, independently, an integer from 0 to 2; and $R^5$ is selected from the group consisting of H, optionally substituted $C_{1-6}$ alkyl, and optionally substituted heterocyclyl.

19. The method of claim 10, wherein the cationic lipid has the formula:

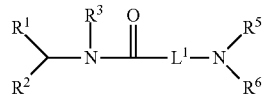

wherein each $R^1$ and $R^2$ is, independently, optionally substituted $C_{11-24}$ alkyl, optionally substituted $C_{11-24}$ alkenyl, optionally substituted $C_{11-24}$ alkynyl, optionally substituted $C_{11-24}$ heteroalkyl, optionally substituted $C_{11-24}$ heteroalkenyl, or optionally substituted $C_{11-24}$ heteroalkynyl; $R^3$ is H or optionally substituted $C_{1-6}$ alkyl; $L^1$ is optionally substituted $C_{1-6}$ alkylene; and each $R^5$ and $R^6$ is, independently, H or optionally substituted $C_{1-6}$ alkyl, or where $R^5$ and $R^6$ combine to form an optionally substituted $C_{3-7}$ heterocyclyl.

20. The method of claim 10, wherein the neutral aqueous solution of step (c) is water.

* * * * *